United States Patent [19]

Rivier

[11] Patent Number: 5,777,073

[45] Date of Patent: *Jul. 7, 1998

[54] CYCLIC CRF ANTAGONIST PEPTIDES

[75] Inventor: Jean E. F. Rivier, La Jolla, Calif.

[73] Assignee: The Salk Institute for Biological Studies, San Diego, Calif.

[*] Notice: The term of this patent shall not extend beyond the expiration date of Pat. No. 5,663,292.

[21] Appl. No.: 865,773

[22] Filed: May 30, 1997

Related U.S. Application Data

[63] Continuation-in-part of Ser. No. 556,578, Nov. 13, 1995, which is a continuation-in-part of Ser. No. 353,928, Dec. 12, 1994, Pat. No. 5,663,292.

[51] Int. Cl.$^6$ .......................... A61K 38/28; A61K 38/35; C04K 5/00; C04K 7/00
[52] U.S. Cl. .......................... 530/306; 530/314; 514/11; 514/12; 930/21; 930/70; 930/260; 930/270
[58] Field of Search .................................. 530/317, 306; 514/12, 11; 930/21, 70, 260, 270

[56] References Cited

U.S. PATENT DOCUMENTS

| | | | |
|---|---|---|---|
| 4,632,789 | 12/1986 | Seidah et al. | 530/306 |
| 5,064,939 | 11/1991 | Rivier et al. | 530/317 |
| 5,109,111 | 4/1992 | Rivier et al. | 530/306 |
| 5,245,009 | 9/1993 | Kornreich et al. | 530/306 |
| 5,278,146 | 1/1994 | Rivier et al. | 514/12 |
| 5,439,885 | 8/1995 | Kornreich et al. | 514/12 |
| 5,493,006 | 2/1996 | De Miranda et al. | 530/306 |

OTHER PUBLICATIONS

Gulyas et al., "Potent, structurally constrianed agonists and competitive of corticotropin-releasing factor", P.N.A.S., vol. 92, pp. 10575–10579 (Nov./95).

Miranda et al., Conformationally Restricted Competitive Antagonists of Human/Rat Corticotropin–Releasing Factor, *J. Med. Chem.*, vol. 37, pp. 1450–1459 (1994).

Rivier et al., Synthetic Competitive Antagonists of Corticotropin Releasing Factor: Effect on ACTH Secretion in the Rat, *Science*, vol. 224, pp. 889–891 (May/84).

Gilon, et al., "Backbone Cyclization", *Biopolymers*, vol. 31, pp. 745–750 (1991).

*Primary Examiner*—Robert J. Hill, Jr.
*Assistant Examiner*—Jennifer Harle
*Attorney, Agent, or Firm*—Fitch, Even, Tabin & Flannery

[57] ABSTRACT

Novel cyclic CRF antagonist peptides are created by shortening the N-terminus of a CRF family peptide by 8-11 residues and adding an acyl group. CML is preferably present in what would be the 27-position of the native CRF sequence, and D-Tyr may be incorporated at the N-terminus to facilitate labelling. The cyclizing bond is preferably created between the side chains of the residues in positions 30 and 33; but it may alternatively be created between the residues in either of positions 28 and 29 with those in positions 31 and 32 or with those in positions 32 and 33, respectively. The side chain of Lys in position 33 is preferably linked to the side chain of Glu in position 30 by a lactam bridge to form the cyclic peptide. Disclosed CRF antagonists include:

(cyclo 30-33) [Ac-Asp$^9$, D-Phe$^{12}$, Nle$^{21,38}$, CML$^{27,40}$, Glu$^{30}$, Lys$^{33}$]r/hCRF(9-41), (cyclo 30-33) [Ac-Asp$^9$, D-Phe$^{12}$, Nle$^{21,38}$, CML$^{27,37}$, Glu$^{30}$, Lys$^{33}$]r/hCRF(9-41), (cyclo 30-33) [Ac-Asp$^9$, D-Phe$^{12}$, CML$^{14,27}$, Nle$^{21,38}$, Glu$^{30}$, Lys$^{33}$]r/hCRF(9-41), (cyclo 30-33) [Ac-Asp$^9$, D-Phe$^{12}$, Nle$^{21,38}$, CML$^{27}$, Glu$^{30}$, Lys$^{33}$]r/hCRF(9-41), (cyclo 30-33) [Ac-Asp$^9$, D-Phe$^{12}$, CML$^{18,27}$, Nle$^{21,38}$, Glu$^{30}$, D-His$^{32}$, Lys$^{33}$]r/hCRF(9-41) and (cyclo 30-33) [Ac-Asp$^9$, D-Phe$^{12}$, CML$^{18,27}$, Nle$^{21,38}$, Glu$^{30}$, Lys$^{33}$]r/hCRF(9-41).

20 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ser Gln Glu Pro Pro Ile Ser Leu Asp Leu Thr Phe His Leu Leu Arg
 1               5                  10                  15

Glu Val Leu Glu Met Thr Lys Ala Asp Gln Leu Ala Gln Gln Ala His
             20                  25                  30

Ser Asn Arg Lys Leu Leu Asp Ile Ala
```

(2) INFORMATION FOR SEQ ID NO:2:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO:2:

Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
            20                  25                  30

Ser Asn Arg Lys Leu Met Glu Ile Ile
            35                  40

(2) INFORMATION FOR SEQ ID NO:3:

(i) SEQUENCE CHARACTERISTICS:
       (A) LENGTH: 40 amino acids
       (B) TYPE: amino acid
       (D) TOPOLOGY: linear (ii) MOLECULE TYPE: peptide (xi) SEQUENCE DESCRIPTION: SEQ ID NO:3:

Glu Gly Pro Pro Ile Ser Ile Asp Leu Ser Leu Glu Leu Leu Arg Lys
 1               5                  10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40

(2) INFORMATION FOR SEQ ID NO:4:

(i) SEQUENCE CHARACTERISTICS:
       (A) LENGTH: 41 amino acids
       (B) TYPE: amino acid
       (D) TOPOLOGY: unknown (ii) MOLECULE TYPE: peptide (xi) SEQUENCE DESCRIPTION: SEQ ID NO:4:

Ser Gln Glu Pro Pro Ile Ser Leu Asp Leu Thr Phe His Leu Leu Arg
 1               5                  10                  15

Glu Met Leu Glu Met Ala Lys Ala Glu Gln Glu Ala Glu Gln Ala Ala
            20                  25                  30

Leu Asn Arg Leu Leu Leu Glu Glu Ala
            35                  40

(2) INFORMATION FOR SEQ ID NO:5:

(i) SEQUENCE CHARACTERISTICS:
       (A) LENGTH: 41 amino acids
       (B) TYPE: amino acid
       (D) TOPOLOGY: unknown (ii) MOLECULE TYPE: peptide (xi) SEQUENCE DESCRIPTION: SEQ ID NO:5:

Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
                    20                  25                  30
Ser Asn Arg Lys Leu Met Glu Asn Phe
            35                  40

( 2 ) INFORMATION FOR SEQ ID NO:6:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

Ser Gln Glu Pro Pro Ile Ser Leu Asp Leu Thr Phe His Leu Leu Arg
 1                   5                  10                  15

Glu Val Leu Glu Met Thr Lys Ala Asp Gln Leu Ala Gln Gln Ala His
                    20                  25                  30

Asn Asn Arg Lys Leu Leu Asp Ile Ala
            35                  40

( 2 ) INFORMATION FOR SEQ ID NO:7:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Ser Glu Glu Pro Pro Ile Ser Leu Asp Leu Thr Phe His Leu Leu Arg
 1                   5                  10                  15

Glu Val Leu Glu Met Ala Arg Ala Glu Gln Leu Ala Gln Gln Ala His
                    20                  25                  30

Ser Asn Arg Lys Met Met Glu Ile Phe
            35                  40

( 2 ) INFORMATION FOR SEQ ID NO:8:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Asn Asp Asp Pro Pro Ile Ser Ile Asp Leu Thr Phe His Leu Leu Arg
 1                   5                  10                  15

Asn Met Ile Glu Met Ala Arg Asn Glu Asn Gln Arg Glu Gln Ala Gly
                    20                  25                  30

Leu Asn Arg Lys Tyr Leu Asp Glu Val
            35                  40

( 2 ) INFORMATION FOR SEQ ID NO:9:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Asn Asp Asp Pro Pro Ile Ser Ile Asp Leu Thr Phe His Leu Leu Arg
 1            5                  10                  15

Asn Met Ile Glu Met Ala Arg Ile Glu Asn Glu Arg Glu Gln Ala Gly
            20                  25                  30

Leu Asn Arg Lys Tyr Leu Asp Glu Val
         35              40
```

( 2 ) INFORMATION FOR SEQ ID NO:10:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
Ser Glu Glu Pro Pro Met Ser Ile Asp Leu Thr Phe His Met Leu Arg
 1            5                  10                  15

Asn Met Ile His Arg Ala Lys Met Glu Gly Glu Arg Glu Gln Ala Leu
            20                  25                  30

Ile Asn Arg Asn Leu Leu Asp Glu Val
         35              40
```

( 2 ) INFORMATION FOR SEQ ID NO:11:

( i ) SEQUENCE CHARACTERISTICS:
        ( A ) LENGTH: 41 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Ser Glu Asp Pro Pro Met Ser Ile Asp Leu Thr Phe His Met Leu Arg
 1            5                  10                  15

Asn Met Ile His Met Ala Lys Met Glu Gly Glu Arg Glu Gln Ala Gln
            20                  25                  30

Ile Asn Arg Asn Leu Leu Asp Glu Val
         35              40
```

CYCLIC CRF ANTAGONIST PEPTIDES

This application is a continuation-in-part of my earlier application Ser. No. 08/556,578, filed Nov. 13, 1995, allowed, which is a continuation-in-part of my earlier application Ser. No. 08/353,928 filed Dec. 12, 1994, now U.S. Pat. No. 5,663,292 issued Sep. 2, 1997 the disclosures of which are incorporated herein by reference.

This invention was made with Government support under grant number DK-26741 awarded by the National Institutes of Health. The Government has certain rights in this invention.

This invention is generally directed to peptides and to the pharmaceutical treatment of mammals using such peptides. More specifically, the invention relates to cyclic antagonists of the CRF hentetracontapeptides as well as to members of the larger family of CRF-like peptides, to pharmaceutical compositions containing such cyclic CRF antagonists, to methods of treatment of mammals using such cyclic CRF antagonists, and to methods of screening for new drugs using such peptides.

BACKGROUND OF THE INVENTION

Experimental and clinical observations have supported the concept that the hypothalamus plays a key role in the regulation of adenohypophysial corticotropic cells' secretory functions. Over 40 years ago it was demonstrated that factors present in the hypothalamus would increase the rate of ACTH secretion by the pituitary gland when incubated in vitro or maintained in an organ culture. However, a physiologic corticotropin releasing factor (CRF) was not characterized until ovine CRF (oCRF) (SEQ ID NO:1) was characterized in 1981. As disclosed in U.S. Pat. No. 4,415,558, the disclosure of which is incorporated herein by reference, oCRF was found to be a 41-residue amidated peptide. oCRF lowers blood pressure in mammals when injected peripherally and stimulates the secretion of ACTH and β-endorphin.

Rat CRF (rCRF) (SEQ ID NO:2) was later isolated, purified and characterized; it was found to be a homologous, amidated hentetracontapeptide as described in U.S. Pat. No. 4,489,163, the disclosure of which is incorporated herein by reference. The amino acid sequence of human CRF has now been determined to be the same as that of rCRF. rCRF and hCRF are used interchangeably, and the designation r/hCRF is frequently used with respect to this peptide hormone. These peptide hormones may be considered to form a part of a larger family of native CRF-like peptides and analogs which include the mammalian and fish CRFs, the urotensins and sauvagine (SEQ ID NO:3), as discussed in Vale et al., "Characterization of the Hypothalamic Peptide: Corticotropin Releasing Factor", *Proceedings of the Naito International Symposium on Natural and Biological Activity*, Tokyo, Japan, Nov. 5–7, 1985, and Lederis et al., "Neurohormones from Fish Tails, II: Actions of Urotensin I in Mammals and Fishes", *Recent Progress in Hormone Research*, Vol. 41, Academic Press, Inc. (1985).

Although originally isolated and characterized on the basis of its role in this hypothalamo-pituitary-adrenal (HPA) axis, CRF has been found to be distributed broadly throughout the central nervous system as well as in extraneural tissues, such as the adrenal glands, placenta and testes, where it may also act as a paracrine regulator or a neurotransmitter. Moreover, the likely involvement of CRF in affective disorders, such as anxiety, depression, alcoholism and anorexia nervosa, and in modulating reproduction and immune responses suggests that changes in CRF expression may have important physiological and pathophysiological consequences. For example, perturbations in the regulatory loops comprising the HPA axis often produce chronically elevated levels of circulating glucocorticoids; such patients display the physical hallmarks of Cushing's syndrome, including truncal obesity, muscle-wasting, and reduced fertility.

In addition to its role in mediating activation of the hypothalamic-pituitary-adrenal, CRF has also been shown to modulate autonomic and behavioral changes, some of which occur during the stress response. Many of these behavioral changes have been shown to occur independently of HPA activation in that they are not duplicated by dexamethasone treatment and are insensitive to hypophysectomy. In addition, direct infusion of CRF into the CNS mimics autonomic and behavioral responses to a variety of stressors. Because peripheral administration of CRF or a CRF antagonist fails to affect certain of these changes, it appears that CRF exhibits a direct brain action with respect to such functions, which include appetite suppression, increased arousal and learning ability. However, CRF antagonists given peripherally block endogenous CRF-mediated increases in ACTH secretion, and when delivered into the cerebral ventricles can mitigate stress-induced changes in autonomic activity and behavior.

As a result of the extensive anatomical distribution and multiple biological actions of CRF, this regulatory peptide is believed to be involved in the regulation of numerous biological processes. CRF has also been implicated in the regulation of inflammatory responses. Although it has been observed that CRF plays a pro-inflammatory role in certain animal models, CRF appears to suppress inflammation in others by reducing injury-induced increases in vascular permeability.

A CRF analog having a high alpha-helical forming potential was developed in about early 1984. It is a 41-residue amidated peptide commonly referred to as AHC (alpha-helical CRF) (SEQ ID NO:4) and is described in U.S. Pat. No. 4,594,329, the disclosure of which is incorporated herein by reference; it is considered to now be a member of the overall family of CRF-like peptides. Other CRF analogs containing D-isomers of α-amino acids were developed, such as those shown in U.S. Pat. No. 5,278,146. Synthetic r/hCRF, oCRF and AHC all stimulate ACTH and β-endorphin-like activities (β-END-Li) in vitro and in vivo and substantially lower blood pressure when injected peripherally. Antagonists of these three peptides and of sauvagine and urotensin are disclosed in U.S. Pat. No. 4,605,642, issued Aug. 12, 1986, the disclosure of which is incorporated herein by reference. Cyclic CRF antagonists exhibiting biopotency were earlier developed as disclosed in U.S. Pat. No. 5,245,009 (Sep. 14, 1993) and in U.S. Pat. No. 5,493,006, issued Feb. 20, 1996.

Since the foregoing discoveries, the search for improved CRF antagonists has continued.

SUMMARY OF THE INVENTION

CRF antagonist peptides have now been discovered which exhibit longer lasting and increased biological activity in comparison to known CRF antagonists, and many of them exhibit substantially no residual CRF agonist activity. Moreover, they exhibit high solubility in neutral aqueous solutions, e.g. at physiological pH, and high receptor affinity.

It is shown that any of the members of the family of CRF-like peptides can be modified to create highly biopotent CRF antagonists that bind strongly to the known CRF receptors (CRF-R) without significantly activating same and thus block the action of CRF at its receptors. They exhibit an affinity for CRF-R higher than that exhibited by oCRF, i.e. by an amount outside of the range of experimental error. These modifications include N-terminally shortening the native or other molecule so that it has a length of 30 to 33 residues, e.g. r/hCRF(9-41), r/hCRF(10-41), r/hCRF(11-41) and r/hCRF(12-41), and incorporating a cyclizing bond, preferably a lactam, which joins the side chains of the residues that are located in the positions of the 8th and 11th residues from the C-terminal residue, e.g. (cyclo 30-33) [Glu$^{30}$, Lys$^{33}$]r/hCRF(12-41). The latter cyclizing modification unexpectedly very substantially increases the biopotency of the comparable linear peptide, which is true generally regardless of what residue is present as the 9th residue from the C-terminal residue, i.e. in the 32-position in CRF, so there is wide latitude with respect to such residue. However, it has further been found that D-isomer α-amino acids are also well-tolerated at this position, and the optional incorporation of a D-isomer, preferably of a basic and/or aromatic amino acid, as this residue, e.g. (cyclo 30-33) [Glu$^{30}$, D-His$^{32}$, Lys$^{33}$]-r/hCRF(12-41), may frequently still further improve biopotency of the analog. As a result of continuing study, it has been found that the combination of this cyclizing bond plus the acylation of the N-terminus creates a molecule of long-acting duration and that such effect may be greatest in a peptide of 33 residues in length, e.g. (cyclo 30-33) [Ac-Ser$^9$, Glu$^{30}$, Lys$^{33}$]-r/hCRF(9-41). The family of CRF-like peptides is considered to encompass those peptides which bind to the CRF receptors and have at least about 45% amino acid structural homology with ovine CRF, the first mammalian CRF isolated and characterized. The CRF-like family includes, but is not limited to, the following known peptides: ovine CRF (SEQ ID NO:1), rat/human CRF (SEQ ID NO:2), porcine CRF (SEQ ID NO:5), bovine CRF (SEQ ID NO:6), fish CRFs (SEQ ID NO:7),5 α-helical CRF(AHC) (SEQ ID NO:4), carp urotensin (SEQ ID NO:8), sucker urotensin (SEQ ID NO:9), maggy sole urotensin (SEQ ID NO:10), flounder urotensin (SEQ ID NO:11) and sauvagine (SEQ ID NO:3).

Basically, this preferred class of CRF antagonist peptides may be identified by the following general formula: A-D-Xaa-B-Xaa$_c$-Xaa$_a$-Xaa$_b$-Xaa$_c$-C-NH$_2$ wherein A is Asp-Leu-Thr or Asp-Leu-Ser; D-Xaa is D-Phe, D-2Nal or D-Leu; B is a sequence of 17 amino acid residues that is found between Phe in the 12-position and Gln in position-30 of r/hCRF or the corresponding sequence of another peptide of the CRF family; Xaa$_c$ represent a pair of amino acid residues, the side chains of which are linked in a cyclizing bond; Xaa$_a$ is a natural α-amino acid residue other than Cys; Xaa$_b$ is a residue of either (a) a D-isomer amino acid from the group consisting of D-isomers of natural α-amino acids other than Cys and unnatural aromatic α-amino acids, or (b) a natural L-isomer α-amino acid other than Cys; and C is a sequence of the last 8 amino acid residues of the C-terminal portion of a peptide of the CRF family. The N-terminus of the peptide is N-acylated. Additional substitutions such as are presently well known in the field of CRF agonists may also be made in these modified cyclic peptides, e.g. the substitution of Met by Nle or Leu. Moreover, the N-terminus may be shortened by deleting Asp or Asp-Leu or all of A (i.e. des A) to provide equivalent peptides.

As indicated above, these peptides have a cyclizing bond between the residues in what would be the 30- and 33-positions in mammalian CRF and may optionally have a second such bond between the residues in the 20- and 23-positions. Either or both of these bonds may be a disulfide linkage between two Cys residues, but they are preferably each an amide bond (or lactam bridge) between side chain carboxyl and amino groups. Most preferably, there is a lactam bridge between a side chain carboxyl group on the residue in the 30-position, preferably Glu, and a side chain amino group on the 33-position residue, preferably Lys or Orn. Although the naturally occurring residues of the CRF-like family may be present in the position which corresponds to the 32-position of CRF, i.e. His, Gly, Leu, Gln and Ala, it appears that any α-amino acid is tolerated here. Preferably however, a basic and/or aromatic D-isomer residue or an equivalent is present in the 32-position in the region between the residues joined by this lactam bridge, e.g. D-His, D-Arg, D-Tyr, imBzlD-His, D-Nal D-Pal, D-Trp, D-Dpr(Nic), D-Aph, D-Agl(Nic), D-Orn, D-Dbu, D-Dpr, D-Orn(Nic) or a comparable D-isomer. However, a wide variety of other residues such as D-Ala, D-Glu, D-Asn, Aib, Asn, Pal, Nal, Phe and Tyr may be present. When the second cyclizing bond option is incorporated, a lactam bridge between Glu in the 20-position and Lys in the 23-position is most preferred. A D-isomer may also be optionally included in the 22-position.

As described herein, the lactam linkage between the side chains of the residues in the 30- and 33-positions is preferred; however, biopotency is also increased, but to a somewhat lessor degree, by alternative cyclizing linkages in this same region of the molecule. For example, the side chain of Glu$^{28}$ or Glu$^{29}$ can be linked respectively to Lys$^{31}$ or Lys$^{32}$, or instead respectively to Lys$^{32}$ or Lys$^{33}$ (creating a one-residue longer span). These somewhat less biopotent alternatives are considered to be equivalents to the 30-33 cyclizing linkage.

These peptides also have the preferred inclusion of D-Phe, D-2Nal or D-Leu or an equivalent D-isomer, e.g., D-Cpa, D-Tyr, D-Trp or D-3Pal, in the 12-position, and they have norleucine substituted for any naturally occurring Met, e.g., in the 21 and 38 positions of r/h CRF. If it is desired to label the peptide as by adding a radioactive isotope or a fluorescent dye as is well known in this art, D-Tyr, Tyr or an acyl group having a hydroxy aryl moiety (e.g. desNH$_2$-Tyr) may be added at the N-terminus; Ac-D-Tyr or Ac-Tyr may also be used. When the N-terminus is to be radioiodinated, it may be preferable to substitute Asn, D-Asn or D-Ala for His$^{32}$ or D-His$^{32}$ and Arg for Lys$^{36}$ as they are generally considered to be structural equivalents which may be more stable. Other optional substitutions may also be made throughout the molecule as previously taught, and these are considered to be functional equivalents of the specific peptides described hereinafter. Of particular interest are those analogs wherein the Leu residue in the 27-position is substituted with a methyl group on its α-carbon atom, i.e., CML. CML may optionally be present in the 10-, 14-, 15-, 17-, 18-, 24-, 36-, 37-, 38-, 40- and/or and/or 41-positions, and analogs including CML$^{27}$ and at least one more such CML residue are preferred. CML may be substituted in the 19- position and the 21-position to provide equivalent analogs. In addition, C$^\alpha$MeAla(CMA), which is α-aminoisobutyric acid (Aib), may be optionally inserted at positions 22, 24, 28, 29, 31, 32, 34, 39, 40 and 41. Such substitutions, both alone and in combination with various of the aforementioned substitutions, are considered to enhance biopotency and/or to increase duration of action. For example, the combination of CML$^{27}$ with one or more of CML$^{14}$, CML$^{18}$, CML$^{37}$, and CML$^{40}$ and/or with one or more of Aib$^{22}$, Aib$^{24}$, Aib$^{28}$ and Aib$^{31}$ together with the 30-33 sidechain bridge provides long duration of bioactivity.

As earlier indicated, these improved CRF antagonists are created by shortening the N-terminus of a native CRF-like peptide or analog thereof and incorporating the desired substitutions. Preferably, a sequence of 8 or 9 residues beginning at the N-terminus of the native molecule is deleted; however, 10 or 11 may be deleted. For example, when a mammalian CRF is shortened, the resultant molecule may be accordingly referred to as CRF(9-41), CRF(10-41), CRF(11-41) or CRF(12-41), and the longer analogs CRF(9-41) and CRF(10-41) with an acylated N-terminus are preferred for peptides that will exhibit long duration of biopotency.

Pharmaceutical compositions in accordance with the invention include such CRF antagonists or nontoxic addition salts thereof that are dispersed in a pharmaceutically acceptable liquid or solid carrier. Some such formulations are facilitated because of high solubility at physiological pH; however, formulations in aqueous solutions of mannitol or corn oil may be preferred for subcutaneous (s.c.) administration. The administration of such peptides or pharmaceutically acceptable addition salts thereof to mammals, particularly humans, in accordance with the invention may be carried out for the regulation of secretion of ACTH, β-endorphin, β-lipotropin, corticosterone and other products of the pro-opiomelanocortin (POMC) gene and/or for affecting mood, behavioral and gastrointestinal functions and autonomic nervous system activities. For example, these CRF antagonists may be administered to reduce high ACTH levels, and thereby treat stress-related illnesses, such as stress-induced depression and anxiety, to raise blood pressure when injected iv, to decrease blood flow to the gastrointestinal tract, i.e. particularly to treat patients suffering from irritable bowel syndrome and gastrointestinal diseases, and also to treat inflammatory disorders; immune suppression; human immunodeficiency virus (HIV) infections; Alzheimer's disease; anorexia nervosa; hemorrhagic stress; drug and alcohol withdrawal symptoms; drug addiction, and fertility problems. Because of these broad effects, it may be desirable to administer these peptides with hormonal replacement therapy as discussed hereinafter.

The peptides also provide the basis for valuable methods for drug screening in order to detect even more potent molecules that will bind to and/or activate CRF receptors as a result of their high affinity for CRF receptors.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine, Orn=L-ornithine, Nle=L-norleucine, Nva=L-norvaline, Agl=aminoglycine, Dbu=L-2,4-diaminobutyric acid, Dpr=L-2,3-diaminopropionic acid, Hly=L-homolysine and Har=L-homoarginine. In addition the following abbreviations are used: CML=$C^\alpha CH_3$-L-leucine; Aib=$C^\alpha CH_3$-alanine or 2-aminoisobutyric acid; Nal=L-β-(1- or 2-naphthyl)alanine; Pal=L-β-(2-, 3- or 4-pyridyl)alanine; Cpa=L-(2-, 3-, or 4-chloro) phenylalanine; Aph=L-(2-, 3- or 4-amino) phenylalanine; Amp=(2-, 3- or 4-aminomethyl) phenylalanine; Nic=3-carboxypyridine (or nicotinic acid); Pn=propionyl; iPn=isopropionyl; butyryl=Bt; valeryl=Vl; Vac=vinylacetyl; Nph=naphthoyl; and Flu=fluorenoyl.

Generally, the CRF antagonists include a D-isomer in the 12-position (which can be the N-terminus although the peptide is preferably extended), may include a D-isomer in the 32-position, and have the following formula, or are equivalent nontoxic salts thereof: (cyclo 30-33)Y-D-Phe-$R_{13}$-$R_{14}$-$R_{15}$-Arg-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$-$R_{38}$-$R_{39}$-$R_{40}$-$R_{41}$-$NH_2$ wherein Y is H or an acyl group having up to 15 carbon atoms, preferably up to 12 carbon atoms, and more preferably 1 to 7 carbon atoms, e.g. Ac, For, Acr or Bz; $R_{13}$ is His, Tyr or Glu; $R_{14}$ is CML or Leu; $R_{15}$ is Leu or CML; $R_{17}$ is Glu, CML, Asn or Lys; $R_{18}$ is Val, CML, Nle or Met; $R_{19}$ is Leu, CML or Ile; $R_{20}$ is Glu, D-Glu, Cys or His; $R_{21}$ is Nle or Met; $R_{22}$ is Ala, D-Ala, Aib, Thr, D-Thr, Glu or D-Glu; $R_{23}$ is Arg, Cys, Orn or Lys; $R_{24}$ is Ala, Aib or CML; $R_{25}$ is Glu or Asp; $R_{26}$ is Gln, Asn or Lys; $R_{27}$ is Leu or CML; $R_{28}$ is Ala or Aib; $R_{29}$ is Gln, Aib or Glu; $R_{30}$ is Glu or Cys; $R_{31}$ is Ala or Aib; $R_{32}$ is His, D-His, Aib or a D- or L-isomer of any α-amino acid other than Cys; $R_{33}$ is Lys, Orn or Cys; $R_{34}$ is Asn or Aib; $R_{36}$ is Lys, Orn, Arg, Har, CML or Leu; $R_{37}$ is CML, Leu or Tyr; $R_{38}$ is Nle, CML or Met; $R_{39}$ is Glu, Aib or Asp; $R_{40}$ is Ile, CML, Aib, Thr, Asn, Glu, Ala, Val, Leu, Nle, Phe, Nva, Gly or Gln; and $R_{41}$ is Ala, Aib, Ile, Gly, Val, Leu, CML, Nle, Phe, Nva or Gln; wherein a single amino acid, such as Thr, a dipeptide, such as Leu-Thr, or a tripeptide such as Asp-Leu-Thr, may be optionally included at the N-terminus; and wherein D-Phe$^{12}$ may be substituted by another D-amino acid, such as D-Leu, D-Tyr, D-Cpa, D-Nal, D-Trp or D-Pal, or by Phe or Tyr; provided that when $R_{30}$ is Glu, $R_{33}$ is Lys or Orn and when $R_{30}$ is Cys, $R_{33}$ is Cys; and provided further that a second cyclizing bond may exist between $R_{20}$ and $R_{23}$. As an alternative to such optional acylation at the N-terminus, a sulfonamide may be formed, or a sugar or a lipid can be added to modulate hydrophilicity and therefore duration of action and solubility. As earlier indicated, there is wide latitude for selection of the residue in position-32, and examples of suitable additional residues for $R_{32}$ include the D- and L-isomers of Asn, Trp, Arg, Nal, imBzlHis, Tyr, Ala, Leu, Val, Ser, Thr, Cpa, Pal, Lys, Phe and Gln, as well as Aib, Gly, D-Dpr(Nic), D-Aph, D-Agl(Nic), D-Orn, D-Dbu, D-Dpr, or D-Orn(Nic). If a second cyclizing bond is present, preferably both bonds are not Cys-Cys.

Still another group of preferred CRF antagonists has the following formula (including nontoxic salts thereof): (cyclo 30-33)Y-$R_{12}$-$R_{13}$-$R_{14}$-$R_{15}$-Arg-$R_{17}$-$R_{18}$-$R_{19}$-$R_{20}$-Nle-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein Y is Ac or hydrogen; $R_{12}$ is D-Phe, D-Leu, D-2Nal or D-Tyr; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{19}$ is Leu or CML; $R_{20}$ is Glu or Cys; $R_{22}$ is Ala, D-Ala, Aib, Thr, Asp or Glu; $R_{23}$ is Arg, Cys, Orn or Lys; $R_{24}$ is Ala or Aib; $R_{25}$ is Asp or Glu; $R_{26}$ is Gln, Asn or Lys; $R_{27}$ is Leu or CML; $R_{28}$ is Ala or Aib; $R_{29}$ is Gln, Aib or Glu; $R_{30}$ is Glu or Cys; $R_{31}$ is Ala or Aib; $R_{32}$ is His, D-His, Aib, D-Arg, D-2Nal, D-3Pal, D-Trp, imBzlD-His, Gly, Tyr, D-Tyr, Leu, D-Leu, Ala or D-Ala; $R_{33}$ is Lys, Orn or Cys; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Asn or Gln; and $R_{41}$ is Ala, Aib, Ile, CML, Val or Phe; and wherein Thr, Leu-Thr or Asp-Leu-Thr may be optionally included at the N-terminus; provided that when $R_{30}$ is Glu, $R_{33}$ is Lys or Orn and when $R_{30}$ is Cys, $R_{33}$ is Cys; and provided further that a second cyclizing bond may exist between $R_{20}$ and $R_{23}$.

Another preferred group of CRF antagonists has the following formula (including nontoxic salts thereof): (cyclo 30-33)Y-$R_{12}$-His-Leu-Leu-Arg-Glu-$R_{18}$-$R_{19}$-$R_{20}$-$R_{21}$-$R_{22}$-

$R_{23}$-$R_{24}$-$R_{25}$-Gln-$R_{27}$-$R_{28}$-Gln-$R_{30}$-$R_{31}$-$R_{32}$-$R_{33}$-$R_{34}$-Arg-Lys-Leu-Nle-$R_{39}$-Ile-$R_{41}$-NH$_2$ wherein Y is Ac or H; $R_{12}$ is D-Phe, D-Leu, D-2Nal or D-Tyr; $R_{18}$ is Val, CML or Nle; $R_{19}$ is CML, Leu or Ile; $R_{20}$ is Glu, D-Glu or Cys; $R_{21}$ is Nle or Met; $R_{22}$ is Ala, D-Ala, Aib or Thr; $R_{23}$ is Arg, Cys, Orn or Lys; $R_{24}$ is Ala or Aib; $R_{25}$ is Asp or Glu; $R_{27}$ is Leu or CML; $R_{28}$ is Ala or Aib; $R_{30}$ is Glu or Cys; $R_{31}$ is Ala or Aib; $R_{32}$ is D-His, imBzlD-His, D-Arg, D-2Nal, or a D-isomer of another basic and/or aromatic α-amino acid; $R_{33}$ is Lys, Orn or Cys; $R_{34}$ is Aib or Asn; $R_{39}$ is Glu or Asp; and $R_{41}$ is Ala, Aib, CML or Ile; and wherein Thr, Leu-Thr or Asp-Leu-Thr may be optionally included at the N-terminus; provided however that a second cyclizing bond may exist between $R_{20}$ and $R_{23}$. When it is desired that the peptide very closely resemble r/hCRF, all or a majority of the following selections are incorporated: $R_{18}$ is Val, $R_{22}$ is Ala, $R_{23}$ is Arg, $R_{24}$ is Ala, $R_{25}$ is Glu, $R_{28}$ is Ala, $R_{39}$ is Glu, and $R_{41}$ is Ile.

A more preferred group of antagonists is based upon the sequences of r/hCRF and oCRF and because of the syntheses that have been carried out over the last decade, it has uniformly been shown that any of the residues in the corresponding position in ovine CRF can be substituted into the amino acid sequence of r/hCRF without significantly altering its biopotency. This group has the following formula (including nontoxic salts thereof): (cyclo 30-33)Y-D-Phe-His-Leu-Leu-Arg-Glu-$R_{18}$-Leu-$R_{20}$-Nle-$R_{22}$-$R_{23}$-Ala-$R_{25}$-Gln-Leu-Ala-$R_{29}$-$R_{30}$-Ala-$R_{32}$-$R_{33}$-$R_{34}$-Arg-$R_{36}$-Leu-Nle-$R_{39}$-$R_{40}$-$R_{41}$-NH$_2$ wherein Y is Ac, H, Ac-Thr or H-Thr; $R_{18}$ is Val or Nle; $R_{20}$ is Glu, D-Glu, or Cys; $R_{22}$ is Ala, D-Ala or Thr; $R_{23}$ is Arg, Cys, Orn or Lys; $R_{25}$ is Asp or Glu; $R_{29}$ is Gln or Glu; $R_{30}$ is Glu or Cys; $R_{32}$ is His, D-His, D-Arg, imBzlD-His, D-Nal, D-Glu, D-Ala, D-Trp, D-Pal, D-Dpr (Nic), D-Aph, D-Agl(Nic), D-Orn, D-Dbu, D-Dpr or D-Orn (Nic); $R_{33}$ is Lys, Cys or Orn; $R_{34}$ is Asn or Aib; $R_{36}$ is Lys or Leu; $R_{39}$ is Glu or Asp; $R_{40}$ is Ile or Glu; and $R_{41}$ is Ile, Aib or Ala; and wherein Leu or Asp-Leu may be optionally coupled to Thr at the N-terminus; provided that when $R_{30}$ is Cys, $R_{33}$ is Cys; and when $R_{30}$ is Glu, $R_{33}$ is Orn or Lys; and provided further that D-Tyr or D-Leu or Phe may be substituted for D-Phe at the N-terminus and that a second cyclizing bond may exist between $R_{20}$ and $R_{23}$.

A particularly preferred group of CRF antagonists has the formula (including nontoxic salts thereof): (cyclo 30-33)Y-$R_{12}$-His-Leu-Leu-Arg-Glu-Val-Leu-Glu-Nle-Ala-$R_{23}$-Ala-Glu-Gln-Leu-Ala-Gln-$R_{30}$-Ala-His-$R_{33}$-Asn-Arg-Lys-Leu-Nle-Glu-Ile-Ile-NH$_2$ wherein Y is Ac, H, Ac-Thr or H-Thr; $R_{12}$ is D-Phe, D-Leu, D-2Nal, D-Trp or D-Tyr; $R_{23}$ is Arg or Lys; $R_{30}$ is Cys or Glu; $R_{33}$ is Cys, Lys or Orn; wherein Leu or Asp-Leu may be optionally included at the N-terminus, and wherein His$^{32}$ may optionally be, and preferably is, substituted by D-His, imBzlD-His, D-Arg, D-Tyr, D-Nal, D-Pal, D-Asn, D-Lys, D-Dpr(Nic), D-Aph, D-Phe, D-Cpa, D-Agl(Nic), D-Orn, D-Dbu, D-Dpr or D-Orn(Nic); provided that when $R_{30}$ is Cys, $R_{33}$ is Cys and when $R_{30}$ is Glu, $R_{33}$ is Lys or Orn; and that a second cyclizing bond may exist between Glu$^{20}$ and $R_{23}$. Specific analogs of this group which are considered to be particularly biopotent from the standpoint of reducing high ACTH levels and raising blood pressure are:

cyclo(30-33) [D-Phe$^{12}$, Nle$^{21,38}$, Glu$^{30}$, Lys$^{33}$]r/hCRF(12-41);

cyclo(30-33) [D-Phe$^{12}$, Nle$^{21,38}$, Glu$^{30}$, Orn$^{33}$]r/hCRF(12-41);

cyclo(30-33) [D-Tyr$^{12}$, Nle$^{21,38}$, Glu$^{30}$, Lys$^{33}$]r/hCRF(12-41);

cyclo(30-33) [D-Phe$^{12}$, Nle$^{21,38}$, Glu$^{30}$, D-His$^{32}$, Lys$^{33}$]r/hCRF(12-41);

cyclo(30-33) [D-Phe$^{12}$, Nle$^{21,38}$, Glu$^{30}$, D-2Nal$^{32}$, Orn$^{33}$]r/hCRF(12-41);

cyclo(30-33) [D-Phe$^{12}$, Nle$^{21,38}$, Glu$^{30}$, imBzlD-His$^{32}$, Lys$^{33}$]r/hCRF(12-41).

When D-Tyr$^{12}$ is present, the peptide can be conveniently radiolabelled using $^{125}$I, or Tyr or D-Tyr may be coupled to $R_{12}$ at the N-terminus.

Another particularly preferred group of CRF antagonists has the formula (including nontoxic salts thereof): (cyclo 30-33)Y-$R_{12}$-His-$R_{14}$-$R_{15}$-Arg-$R_{17}$-Val-$R_{19}$-Glu-Nle-Ala-$R_{23}$-Ala-Glu-Gln-$R_{27}$-Ala-Gln-$R_{30}$-Ala-$R_{32}$-$R_{33}$-Asn-Arg-Lys-$R_{37}$-Nle-Glu-Ile-Ile-NH$_2$ wherein Y is Ac, H, Ac-Thr or H-Thr; $R_{12}$ is D-Phe, D-Leu, D-2Nal, D-Trp or D-Tyr; $R_{14}$, $R_{15}$, $R_{19}$, $R_{27}$ and $R_{37}$ are independently Leu or CML; $R_{17}$ is Glu or CML; $R_{23}$ is Arg or Lys; $R_{30}$ is Glu or Cys; $R_{32}$ is D-His, imBzlD-His, D-Arg, D-Asn, D-Tyr, D-Pal, D-Nal or another basic and/or aromatic D-isomer α-amino acid; $R_{33}$ is Lys, Orn or Cys; wherein Leu or Asp-Leu may be optionally coupled to Thr at the N-terminus, and wherein at least one of $R_{14}$, $R_{15}$, $R_{17}$, $R_{19}$, $R_{27}$ and $R_{37}$ is CML; provided that when $R_{30}$ is Cys, $R_{33}$ is Cys and when $R_{30}$ is Glu, $R_{33}$ is Lys or Orn. Specific analogs of this group which are considered to be particularly biopotent from the standpoint of reducing high ACTH levels and raising blood pressure are:

cyclo(30-33) [D-Phe$^{12}$, Nle$^{21,38}$, CML$^{27}$, Glu$^{30}$, D-His$^{32}$, Lys$^{33}$]r/hCRF(12-41);

cyclo(30-33) [D-Phe$^{12}$, CML$^{15}$, Nle$^{21,38}$, Glu$^{30}$, imBzlD-His$^{32}$, Lys$^{33}$]r/hCRF(12-41);

cyclo(30-33) [D-Phe$^{12}$, CML$^{15}$, Nle$^{21,38}$, Glu$^{30}$, D-His$^{32}$, Lys$^{33}$]r/hCRF(12-41);

cyclo(30-33) [D-Phe$^{12}$, CML$^{14}$, Nle$^{21,38}$, Glu$^{30}$, D-His$^{32}$, Lys$^{33}$]r/hCRF(12-41);

cyclo(30-33) [D-Phe$^{12}$, Nle$^{21,38}$, Glu$^{30}$, D-His$^{32}$, Lys$^{33}$, CML$^{37}$]r/hCRF(12-41);

cyclo(30-33) [D-Phe$^{12}$, CML$^{17}$, Nle$^{21,38}$, Glu$^{30}$, D-His$^{32}$, Lys$^{33}$]r/hCRF(12-41); and cyclo(30-33) [D-Phe$^{12}$, CML$^{19}$, Nle$^{21,38}$, Glu$^{30}$, D-His$^{32}$, Lys$^{33}$]r/hCRF(12-41).

Another group of preferred CRF antagonists include a D-isomer in the 12-position and may include a D-isomer in the 32-position; they have the following formula, or are equivalent nontoxic salts thereof: (cyclo 30-33)Y-$R_9$-$R_{10}$-$R_{11}$-D-Phe-$R_{13}$-$R_{14}$-$R_{15}$-Arg-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$-$R_{38}$-$R_{39}$-$R_{40}$-$R_{41}$-NH$_2$ wherein Y is an acyl group having up to 15 carbon atoms, e.g. Nph or Flu, preferably 1 to 7 carbon atoms, e.g. Ac, For, Acr Pn, iPn, Bt, Vl, Vac or Bz; $R_9$ is Asp, Tyr or D-Tyr; $R_{10}$ is Leu or CML; $R_{11}$ is Thr or Ser; $R_{13}$ is His, Tyr or Glu; $R_{14}$ is CML or Leu; $R_{15}$ is Leu or CML; $R_{17}$ is Glu, CML, Asn or Lys; $R_{18}$ is Val, Nle, CML or Met; $R_{19}$ is Leu or Ile; $R_{20}$ is Glu, D-Glu, Cys or His; $R_{21}$ is Nle or Met; $R_{22}$ is Ala, D-Ala, Aib, Thr, D-Thr, Glu or D-Glu; $R_{23}$ is Arg, Cys, Orn or Lys; $R_{24}$ is Ala, Aib or CML; $R_{25}$ is Glu or Asp; $R_{26}$ is Gln, Asn or Lys; $R_{27}$ is Leu or CML; $R_{28}$ is Ala, Lys, Aib or Arg; $R_{29}$ is Gln, Aib or Glu; $R_{30}$ is Glu or Cys; $R_{31}$ is Aib or an L-isomer of an α-amino acid other than Cys; $R_{32}$ is Aib or a D- or L-isomer of an α-amino acid other than Cys; $R_{33}$ is Lys, Orn or Cys; $R_{34}$ is Asn or Aib; $R_{36}$ is Lys, Orn, Arg, Har, CML or Leu; $R_{37}$ is CML, Leu or Tyr; $R_{38}$ is Nle, Met or CML; $R_{39}$ is Glu, Aib or Asp; $R_{40}$ is CML, Ile, Aib, Thr, Asn, Glu, Ala, Val, Leu, Nle, Phe, Nva, Gly or Gln; and $R_{41}$ is Ala, Aib, Ile, Gly, Val, Leu, CML, Nle, Phe, Nva or Gln; wherein D-Phe$^{12}$ may be substituted by another D-amino acid, such as D-Leu, D-Tyr, D-Trp, D-Cpa, D-Trp, D-Nal or D-Pal, or by Phe or Tyr; provided that when $R_{30}$ is Glu, $R_{33}$ is Lys or Orn and when $R_{30}$ is Cys, $R_{33}$ is Cys; and provided further that a second cyclizing bond may exist between $R_{20}$ and $R_{23}$. As an alternative to such acylation at the N-terminus, a sulfonamide may be formed, or a sugar or a lipid can be added to modulate hydrophilicity and therefore duration of action and solubility.

Still another group of preferred CRF antagonists has the following formula (including nontoxic salts thereof): (cyclo 30-33)Y-Asp-Leu-Thr-$R_{12}$-$R_{13}$-$R_{14}$-$R_{15}$-Arg-$R_{17}$-$R_{18}$-Leu-$R_{20}$-Nle-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein Y is an acyl group having not more than 7 carbon atoms; $R_{12}$ is D-Phe, D-Leu, D-2Nal or D-Tyr; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{20}$ is Glu or D-Glu; $R_{22}$ is Ala, D-Ala, Aib, Thr, Asp or Glu; $R_{23}$ is Arg or Lys; $R_{24}$ is Ala, Aib or CML; $R_{25}$ is Asp or Glu; $R_{26}$ is Gln, Asn or Lys; $R_{27}$ is Leu or CML; $R_{28}$ is Ala or Aib; $R_{29}$ is Gln, Aib or Glu; $R_{30}$ is Glu or Cys; $R_{31}$ is Ala or Aib; $R_{32}$ is His, D-His, Aib, D-Arg, D-2Nal, D-3Pal, D-Trp, imBzlD-His, Gly, Tyr, D-Tyr, Leu, D-Leu, Ala or D-Ala; $R_{33}$ is Lys, Orn or Cys; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Asn or Gln; and $R_{41}$ is Ala, Aib, Ile, CML, Val or Phe; and provided that when $R_{30}$ is Glu, $R_{33}$ is Lys or Orn and when $R_{30}$ is Cys, $R_{33}$ is Cys.

Another preferred group of CRF antagonists has the following formula (including nontoxic salts thereof): (cyclo 30-33)Y-Asp-Leu-Thr-$R_{12}$-His-$R_{14}$-Leu-Arg-Glu-$R_{18}$-$R_{19}$-$R_{20}$-$R_{21}$-$R_{22}$-$R_{23}$-$R_{24}$-$R_{25}$-Gln-$R_{27}$-$R_{28}$-Gln-$R_{30}$-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein Y is an acyl group having not more than 7 carbon atoms; $R_{12}$ is D-Phe or D-2Nal; $R_{14}$ is Leu or CML; $R_{18}$ is Val, CML or Nle; $R_{19}$ is Leu or Ile; $R_{20}$ is Glu or D-Glu; $R_{21}$ is Nle or Met; $R_{22}$ is Ala, D-Ala, Aib or Thr; $R_{23}$ is Arg or Lys; $R_{24}$ is Ala or Aib; $R_{25}$ is Asp or Glu; $R_{27}$ is Leu or CML; $R_{28}$ is Ala or Aib; $R_{30}$ is Glu or Cys; $R_{31}$ is Ala or Aib; $R_{32}$ is D-His, imBzlD-His, D-Arg, D-2Nal, or a D-isomer of another basic and/or aromatic α-amino acid; $R_{33}$ is Lys, Orn or Cys; $R_{34}$ is Aib or Asn; $R_{36}$ is Lys or CML; $R_{37}$ is Leu or CML; $R_{39}$ is Glu or Asp; $R_{40}$ is Ile, CML or Aib; and $R_{41}$ is Ala, Aib, CML or Ile. When it is desired that the peptide very closely resemble r/hCRF, all or a majority of the following selections are incorporated: $R_{18}$ is Val, $R_{22}$ is Ala, $R_{23}$ is Arg, $R_{24}$ is Ala, $R_{25}$ is Glu, $R_{28}$ is Ala, $R_{39}$ is Glu, and $R_{41}$ is Ile.

Yet another preferred group of antagonists has the following formula (including nontoxic salts thereof): (cyclo 30-33)Y-Asp-Leu-Thr-D-Phe-His-$R_{14}$-Leu-Arg-Glu-$R_{18}$-Leu-$R_{20}$-Nle-$R_{22}$-$R_{23}$-$R_{24}$-$R_{25}$-Gln-$R_{27}$-$R_{28}$-$R_{29}$-$R_{30}$-$R_{31}$-$R_{32}$-$R_{33}$-$R_{34}$-Arg-$R_{36}$-$R_{37}$-Nle-$R_{39}$-$R_{40}$-$R_{41}$-$NH_2$ wherein Y is Ac, Acr or For; $R_{14}$ is Leu or CML; $R_{18}$ is Val, CML or Nle; $R_{20}$ is Glu or D-Glu; $R_{22}$ is Ala, Aib, D-Ala or Thr; $R_{23}$ is Arg or Lys; $R_{24}$ is Ala or Aib; $R_{25}$ is Asp or Glu; $R_{27}$ is Leu or CML; $R_{28}$ is Ala or Aib; $R_{29}$ is Gln or Glu; $R_{30}$ is Glu or Cys; $R_{31}$ is Ala or Aib; $R_{32}$ is His, D-His, D-Arg, imBzlD-His, D-Nal, D-Glu, D-Ala, D-Pal, D-Trp, D-Dpr(Nic), D-Aph, D-Agl(Nic), D-Orn, D-Dbu, D-Dpr or D-Orn(Nic); $R_{33}$ is Lys, Cys or Orn; $R_{34}$ is Asn or Aib; $R_{36}$ is Lys, CML or Leu; $R_{37}$ is Leu or CML; $R_{39}$ is Glu or Asp; $R_{40}$ is Ile, CML, Aib or Glu; and $R_{41}$ is Ile, Aib, CML or Ala; provided that when $R_{30}$ is Cys, $R_{33}$ is Cys; and when $R_{30}$ is Glu, $R_{33}$ is Orn or Lys; and provided further that D-2Nal or D-Leu or Phe may be substituted for D-Phe.

A particularly preferred group of CRF antagonists has the formula (including nontoxic salts thereof): (cyclo 30-33)Y-$R_9$-Leu-Thr-$R_{12}$-His-Leu-Leu-Arg-Glu-Val-Leu-Glu-Nle-Ala-$R_{23}$-Ala-Glu-Gln-$R_{27}$-Ala-Gln-$R_{30}$-Ala-His-$R_{33}$-Asn-Arg-Lys-Leu-Nle-Glu-Ile-Ile-$NH_2$ wherein Y is Ac or Acr; $R_{12}$ is Asp, Tyr or D-Tyr; $R_{12}$ is D-Phe or D-2Nal; $R_{23}$ is Arg or Lys; $R_{27}$ is Leu or CML; $R_{30}$ is Cys or Glu; $R_{33}$ is Cys, Lys or Orn; and wherein $His^{32}$ may optionally be, and preferably is, substituted by D-His, imBzlD-His, D-Arg, D-Tyr, D-Nal, D-Pal, D-Trp, D-Asn, D-Lys, D-Dpr(Nic), D-Aph, D-Phe, D-Cpa, D-Agl(Nic), D-Orn, D-Dbu, D-Dpr or D-Orn(Nic); provided that when $R_{30}$ is Cys, $R_{33}$ is Cys and when $R_{30}$ is Glu, $R_{33}$ is Lys or Orn. Specific analogs of this group which are considered to be particularly biopotent from the standpoint of reducing high ACTH levels and raising blood pressure are:

cyclo(30-33) [Ac-$Asp^9$, D-$Phe^{12}$, $Nle^{21,38}$, $Glu^{30}$, $Lys^{33}$]r/hCRF(9-41);

cyclo(30-33) [Ac-$Asp^9$, D-$Phe^{12}$, $Nle^{21,38}$, $Glu^{30}$, $Orn^{33}$]r/hCRF(9-41);

cyclo(30-33) [Ac-D-$Tyr^9$, D-$Phe^{12}$, $Nle^{21,38}$, $Glu^{30}$, $Lys^{33}$] r/hCRF(9-41);

cyclo(30-33) [Ac-$Asp^9$, D-$Phe^{12}$, $Nle^{21,38}$, $Glu^{30}$, D-$His^{32}$, $Lys^{33}$]r/hCRF(9-41);

cyclo(30-33) [Ac-$Asp^9$, D-$Phe^{12}$, $Nle^{21,38}$, $Glu^{30}$, D-$2Nal^{32}$, $Orn^{33}$]r/hCRF(9-41); and cyclo(30-33) [Ac-$Asp^9$, D-$Phe^{12}$, $Nle^{21,38}$, $Glu^{30}$, imBzlD-$His^{32}$, $Lys^{33}$]r/hCRF(9-41).

When D-Tyr is present at the N-terminus, the peptide can be conveniently radiolabelled using $^{125}I$.

Another particularly preferred group of CRF antagonists has the formula (including nontoxic salts thereof): (cyclo 30-33)Y-Asp-$R_{10}$-Thr-$R_{12}$-His-$R_{14}$-$R_{15}$-Arg-$R_{17}$-$R_{18}$-Leu-Glu-$R_{21}$-Ala-$R_{23}$-$R_{24}$-Glu-Gln-$R_{27}$-Ala-Gln-$R_{30}$-Ala-$R_{32}$-$R_{33}$-Asn-Arg-$R_{36}$-$R_{37}$-$R_{38}$-Glu-$R_{40}$-$R_{41}$-$NH_2$ wherein Y is Ac, For or Acr; $R_{10}$ is Leu or CML; $R_{12}$ is D-Phe or D-2Nal; $R_{14}$, $R_{15}$, $R_{27}$ and $R_{37}$ are independently Leu or CML; $R_{17}$ is Glu or CML; $R_{18}$ is Val or CML; $R_{21}$ and $R_{38}$ are independently Met, Nle or CML; $R_{23}$ is Arg or Lys; $R_{24}$ is Ala or CML; $R_{30}$ is Glu or Cys; $R_{32}$ is His, D-His, imBzlD-His, D-Arg, D-Asn, D-Tyr, D-Pal, D-Nal, D-Trp or another basic and/or aromatic D-isomer α-amino acid; $R_{33}$ is Lys, Orn or Cys; $R_{36}$ is Lys or CML; and $R_{40}$ and $R_{41}$ are independently Ile or CML; and wherein at least one of $R_{14}$, $R_{18}$, $R_{27}$, $R_{36}$, $R_{37}$, $R_{40}$ and $R_{41}$ is CML; provided that when $R_{30}$ is Cys, $R_{33}$ is Cys and when $R_{30}$ is Glu, $R_{33}$ is Lys or Orn, and that a second cyclizing bond may exist between $Glu^{20}$ and $R_{23}$.

An additional particularly preferred group of CRF antagonists has the formula (including nontoxic salts thereof): (cyclo 30-33)Y-Asp-$R_{10}$-Thr-$R_{12}$-His-$R_{14}$-$R_{15}$-Arg-$R_{17}$-$R_{18}$-Leu-Glu-$R_{21}$-Ala-Arg-$R_{24}$-Glu-Gln-CML-Ala-Gln-Glu-Ala-$R_{32}$-$R_{33}$-Asn-Arg-$R_{36}$-$R_{37}$-$R_{38}$-Glu-$R_{40}$-$R_{41}$-$NH_2$ wherein Y is Ac, For or Acr; $R_{10}$ is Leu or CML; $R_{12}$ is D-Phe or D-2Nal; $R_{14}$, $R_{15}$, and $R_{37}$ are independently Leu or CML; $R_{17}$ is Glu or CML; $R_{18}$ is Val or CML; $R_{21}$ is Met or Nle; $R_{24}$ is Ala or CML; $R_{32}$ is His, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{36}$ is Lys or CML; $R_{38}$ is Met, Nle or CML; and $R_{40}$ and $R_{41}$ are independently Ile or CML; and wherein at least one of $R_{14}$, $R_{18}$, $R_{37}$ and $R_{40}$ is CML. Specific analogs of this group which are considered to be particularly biopotent from the standpoint of reducing high ACTH levels and raising blood pressure are:

cyclo(30-33) [Ac-$Asp^9$, D-$Phe^{12}$, $CML^{14,27}$, $Nle^{21,38}$, $Glu^{30}$, D-$His^{32}$, $Lys^{33}$]r/hCRF(9-41);

cyclo(30-33) [Ac-$Asp^9$, D-$Phe^{12}$, $CML^{18,27}$, $Nle^{21,38}$, $Glu^{30}$, D-$His^{32}$, $Lys^{33}$]r/hCRF(9-41);

cyclo(30-33) [Ac-$Asp^9$, D-$Phe^{12}$, $Nle^{21,38}$, $CML^{27,36,37}$, $Glu^{30}$, $Lys^{33}$]r/hCRF(9-41);

cyclo(30-33) [Ac-Asp$^9$, D-Phe$^{12}$, Nle$^{21,38}$, CML$^{27,40}$, Glu$^{30}$, Lys$^{33}$]r/hCRF(9-41);

cyclo(30-33) [Ac-Asp$^9$, D-Phe$^{12}$, Nle$^{21,38}$, CML$^{27,37}$, Glu$^{30}$, Lys$^{33}$]r/hCRF(9-41);

cyclo(30-33) [Ac-Asp$^9$, D-Phe$^{12}$, CML$^{14,27,40}$, Nle$^{21,38}$, Glu$^{30}$, Lys$^{33}$]r/hCRF(9-41);

cyclo(30-33) [Ac-Asp$^9$, D-Phe$^{12}$, Nle$^{21,38}$, CML$^{27,37,41}$, Glu$^{30}$, Lys$^{33}$]r/hCRF(9-41);

cyclo(30-33) [Ac-Asp$^9$, D-Phe$^{12}$, Nle$^{21,38}$, CML$^{14,27,37,40}$, Glu$^{30}$, Lys$^{33}$]r/hCRF(9-41);

cyclo(30-33) [Ac-Asp$^9$, D-2Nal$^{12}$, CML$^{14,27,37,40}$, Nle$^{21,38}$, Glu$^{30}$, Lys$^{33}$]r/hCRF(9-41); and cyclo(30-33) [Ac-Asp$^9$, D-Phe$^{12}$, Nle$^{21,38}$, CML$^{27,37,40}$, Glu$^{30}$, Lys$^{33}$]r/hCRF(9-41).

Yet another particularly preferred group of CRF antagonists has the formula (including nontoxic salts thereof): (cyclo 30-33)Y-Asp-R$_{10}$-Thr-R$_{12}$-His-R$_{14}$-R$_{15}$-Arg-R$_{17}$-R$_{18}$-Leu-Glu-R$_{21}$-R$_{22}$-R$_{23}$-R$_{24}$-Glu-Gln-CML-R$_{28}$-R$_{29}$-Glu-R$_{31}$-R$_{32}$-R$_{33}$-R$_{34}$-Arg-R$_{36}$-R$_{37}$-R$_{38}$-R$_{39}$-R$_{40}$-R$_{41}$-NH$_2$ wherein Y is an acyl group having up to 15 carbon atoms; R$_{10}$, R$_{14}$, R$_{15}$, and R$_{37}$ are independently Leu or CML; R$_{12}$ is D-Phe or D-2Nal; R$_{17}$ is Glu or CML; R$_{18}$ is Val or CML; R$_{21}$ is Met or Nle; R$_{22}$, R$_{28}$ and R$_{31}$ are independently either Ala or Aib; R$_{23}$ is Arg or Lys; R$_{24}$ is Ala, Aib or CML; R$_{29}$ is Gln or Aib; R$_{32}$ is His, Aib, D-His, imBzlD-His, D-Arg, D-Asn, D-Tyr, D-Pal, D-Nal, D-Trp or another basic and/or aromatic D-isomer α-amino acid; R$_{33}$ is Lys or Orn; R$_{34}$ is Asn or Aib; R$_{36}$ is Lys or CML; R$_{38}$ is Met, Nle or CML; R$_{39}$ is Glu or Aib; and R$_{40}$ is Ile, CML or Aib; R$_{41}$ is Leu, CML or Aib; and wherein at least one of R$_{22}$, R$_{24}$, R$_{28}$, and R$_{31}$ is Aib; provided that a second cyclizing bond may exist between Glu$^{20}$ and R$_{23}$. Specific analogs of this group which are considered to be particularly biopotent from the standpoint of reducing high ACTH levels and raising blood pressure are:

cyclo(30-33) [Ac-Asp$^9$, D-Phe$^{12}$, Nle$^{21,38}$, Aib$^{24}$, CML$^{27,40}$, Glu$^{30}$, Lys$^{33}$]r/hCRF(9-41);

cyclo(30-33) [Ac-Asp$^9$, D-Phe$^{12}$, Nle$^{21,38}$, Aib$^{22}$, CML$^{27,40}$, Glu$^{30}$, Lys$^{33}$]r/hCRF(9-41);

cyclo(30-33) [Ac-Asp$^9$, D-Phe$^{12}$, Nle$^{21,38}$, CML$^{27}$, Aib$^{28}$, Glu$^{30}$, Lys$^{33}$]r/hCRF(9-41);

cyclo(30-33) [Ac-Asp$^9$, D-Phe$^{12}$, Nle$^{21,38}$, CML$^{27,40}$, Aib$^{28}$, Glu$^{30}$, Lys$^{33}$]r/hCRF(9-41);

cyclo(30-33) [Ac-Asp$^9$, D-Phe$^{12}$, Nle$^{21,38}$, CML$^{27,37}$, Aib$^{28,31}$, Glu$^{30}$, Lys$^{33}$]r/hCRF(9-41);

cyclo(30-33) [Ac-Asp$^9$, D-Phe$^{12}$, Nle$^{21,38}$, CML$^{27}$, Glu$^{30}$, Aib$^{31}$, Lys$^{33}$]r/hCRF(9-41); and cyclo(30-33) [Ac-Asp$^9$, D-Phe$^{12}$, CML$^{14,27}$, Nle$^{21,38}$, Glu$^{30}$, Aib$^{31}$, Lys$^{33}$]r/hCRF(9-41).

The peptides are synthesized by a suitable method, such as by exclusively solid-phase techniques, by partial solid-phase techniques, by fragment condensation or by classical solution addition.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

For example, chemical synthesis of a peptide analog from one preferred group may include the initial formation of an intermediate of the following amino acid sequence: X$^1$-Asp(X$^5$)-Leu-Thr(X$^2$)-D-Phe-R$_{13}$(X$^7$ or X$^5$)-Leu-Leu-Arg(X$^3$)-R$_{17}$(X$^5$)-R$_{18}$-Leu-R$_{20}$ (X$^5$ or X$^8$)-Nle-R$_{22}$(X$^2$ or X$^5$)-R$_{23}$ (X$^3$, X$^6$ or X$^8$)-R$_{24}$-R$_{25}$(X$^5$)-R$_{26}$(X$^4$ or X$^6$)-CML-R$_{28}$-R$_{29}$ (X$^4$ or X$^5$)-R$_{30}$ (X$^5$ or X$^8$)-R$_{31}$-R$_{32}$(X$^3$ or X$^7$)-R$_{33}$(X$^6$ or X$^8$)-R$_{34}$(X$^4$)-Arg(X$^3$)-R$_{36}$(X$^3$ or X$^6$)-R$_{37}$(X$^7$)-Nle-R$_{39}$ (X$^5$)-R$_{40}$(X$^2$, X$^4$ or X$^5$)-R$_{41}$(X$^4$)-X$^9$ wherein: the R-groups are as hereinbefore defined.

X$^1$ is either hydrogen or an alpha-amino protecting group. The alpha-amino protecting groups contemplated by X$^1$ are those known to be useful in the art in the step-wise synthesis of polypeptides. Among the classes of alpha-amino protecting groups covered by X$^1$ are (1) acyl-type protecting groups, such as formyl(For), acrylyl(Acr), benzoyl(Bz) and acetyl(Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl methyloxycarbonyl (Fmoc), cyclopentyloxy-carbonyl, adamantyloxycarbonyl, and cyclohexyloxy-carbonyl; and (5) thiourethan-type protecting groups, such as phenylthiocarbonyl. The two preferred alpha-amino protecting groups are BOC and Fmoc.

X$^2$ is a protecting group for the hydroxyl group of Thr or Ser and is preferably selected from the class consisting of acetyl(Ac), benzoyl(Bz), tert-butyl, triphenylmethyl(trityl), tetrahydropyranyl, benzyl ether(Bzl) and 2,6-dichlorobenzyl (DCB). The most preferred protecting group is Bzl. X$^2$ can be hydrogen, which means there is no protecting group on the hydroxyl group.

X$^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

X$^4$ is hydrogen or a protecting group, preferably xanthyl (Xan), for the amido group of Asn or Gln. Asn or Gln is often coupled without side chain protection in the presence of hydroxybenzotriazole (HOBt).

X$^5$ is hydrogen or an ester-forming protecting group for the β- or γ-carboxyl group of Asp or Glu, preferably selected from the esters of cyclohexyl (OChx) benzyl (OBzl), 2,6-dichlorobenzyl, methyl, ethyl and t-butyl (Ot-Bu). OChx is preferred for a BOC strategy.

X$^6$ is hydrogen or a protecting group for the side chain amino substituent of Lys or Orn. Illustrative of suitable side chain amino-protecting groups are Z, 2-chlorobenzyloxycarbonyl(2Cl—Z), Tos, t-amyloxycarbonyl(Aoc), BOC and aromatic or aliphatic urethan-type protecting groups as specified hereinbefore. 2Cl—Z is preferred for a BOC strategy.

When His is present, X$^7$ is hydrogen or a protecting group for the imidazole nitrogen such as Tos or 2,4-dinitrophenyl (DNP), and when Tyr is present, X$^7$ is hydrogen or a protecting group for the hydroxyl group such as DCB. When Met is present, the sulfur may be protected, if desired, with oxygen.

X$^8$ is a protecting group for the sulfhydryl group of Cys, preferably p-methoxybenzyl(MeOBzl), p-methylbenzyl, acetamidomethyl, trityl or Bzl; or a suitable protecting group for an amino side chain which is removable without simultaneously removing the protecting group $X^6$, e.g. a base-labile group such as Fmoc; or a suitable labile protecting group for a carboxyl side chain which is removable without simultaneously removing the protecting group $X^5$, e.g., a base-labile group such as OFm (fluorenylmethyl ester). Alternatively it may be a direct bond between the residues in the 30- and 33-positions, or the residues in the 20- and 23-positions, e.g. when the cyclic form results from a carba or dicarba bond which is considered to be equivalent to a Cys-Cys bond.

The selection of a side chain amino protecting group is not critical except that it should be one which is not removed during deprotection of the alpha-amino groups during the synthesis. Hence, the alpha-amino protecting group and the side chain amino protecting group cannot be the same.

$X^9$ is $NH_2$, a protecting group, such as an ester, or an anchoring bond used in solid phase synthesis for linking to a solid resin support, preferably one of the following: —NH-benzhydrylamine (BHA) resin support and —NH-paramethylbenzhydrylamine(MBHA) resin support. Cleavage from a BHA or MBHA resin directly gives the CRF analog amide. By employing a methyl-derivative of such a resin, a methyl-substituted amide can be created, which is considered to be the equivalent of the unsubstituted amide.

In the amino acid sequence for the intermediate, at least one of $X^1$, $X^2$, $X^3$, $X^4$, $X^5$, $X^6$, $X^7$ and $X^8$ is a protecting group or $X^9$ includes resin support. The particular amino acid chosen for each R-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

For the acylated N-terminus, an acyl group having 15 carbon atoms or less is present, preferably 12 or less, as represented by Y; acetyl(Ac), formyl(For), acrylyl(Acr) and benzoyl(Bz) are the preferred acyl groups although to facilitate labeling, an acylating agent containing a hydroxy aryl moiety, such as 4-hydroxy-phenylpropionic acid (desNH$_2$-Tyr) or 4-hydroxy-phenylacetic acid, may be used. Also, Y may alternatively be a suitable sugar or lipid, which are equivalents that may be used to adjust hydrophilicity.

Thus, in one aspect, there is also provided a process for the manufacture of compounds comprising (a) forming a peptide intermediate, as defined hereinbefore, having at least one protective group wherein: $X^1$, $X^2$, $X^3$, $X^4$, $X^5$, $X^6$, $X^7$ and $X^8$ are each either hydrogen or a protective group, and $X^9$ is either a protective group or an anchoring bond to resin support or $NH_2$, (b) forming a cyclizing bond, particularly if one has not already been formed, (c) removing $X^1$ and acylating the N-terminus, (d) splitting off the remaining protective groups and any anchoring bond from said peptide intermediate, (e) optionally forming a cyclizing bond at this time, and (f) if desired, converting a resulting peptide into a nontoxic addition salt thereof.

The peptides of the invention may be synthesized by classical peptide solution synthesis, and such synthesis is preferred for large quantities. To obtain limited quantities, e.g. less than 1 kg, it may be preferable to prepare them using solid phase synthesis, such as that described by Merrifield, *J. Am. Chem. Soc.*, 85, p 2149 (1964), which facilitates the CRF antagonist peptides being prepared in a straightforward manner and then quickly tested to determine biological activity. This facilitates the ready preparation and evaluation of various CRF antagonist peptides. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for an antagonist based upon human CRF can be prepared by attaching alpha-amino-protected Ile to an MBHA resin.

Ile protected by BOC is coupled to the BHA resin using methylene chloride and/or dimethylformamide (DMF) and/or N-methyl pyrrolidone (NMP). Following the coupling of BOC-Ile to the resin support, the alpha-amino protecting group is removed, as by using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used, as described in Schroder & Lubke, "The Peptides", Vol. 1, 72–75 (Academic Press 1965) and in the well known Barany-Merrifield text.

After removal of the alpha-amino protecting group of Ile, the remaining alpha-amino- and side chain-protected amino acids are coupled stepwise in the desired order to obtain an intermediate compound such as defined hereinbefore. As an alternative to adding each amino acid separately in the synthesis, some of them may be coupled to one another prior to addition to the solid phase reactor.

Activating or coupling reagents for use in the solid phase synthesis of the peptides are well known in the peptide art. Examples of such reagents are suitable carbodiimides, such as N,N'-diisopropyl carbodiimide,(DICI) N,N'-dicyclohexyl carbodiimide(DCC) and N-ethyl-N'-(3-dimethylaminopropyl) carbodiimide. Other activating reagents and their use in peptide coupling are described by Schroder & Lubke, supra, in Chapter III and by Kapoor, *J. Phar. Sci.*, 59, pp 1–27 (1970). P-nitrophenyl ester(ONp) can also be used to activate the carboxyl end of Asn or Gln for coupling. For example, BOC-Asn(ONp) can be coupled overnight using one equivalent of HOBt in a 50% mixture of DMF and methylene chloride.

Each protected amino acid or amino acid sequence is introduced into the solid phase reactor in about a threefold excess, and the coupling is carried out in a medium of dimethylformamide(DMF):CH$_2$Cl$_2$ (1:1) or in CH$_2$Cl$_2$ alone at room temperature. Alternatively, coupling may be carried out at elevated temperature up to about 70° C. in NMP or in a mixture of toluene:DMSO (70:30). In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., *Biopolymers*, 17, pp.1927–1938, (1978).

After the desired amino acid sequence has been completed, the intermediate peptide is removed from the resin support unless it is desired to form the cyclizing bond while attached to the resin, as described hereinafter.

Removal is effected by treatment with a reagent, such as liquid hydrogen fluoride(HF), which not only cleaves the peptide from the resin but also cleaves all remaining side chain protecting groups $X^2$, $X^3$, $X^4$, $X^5$, $X^6$ and $X^7$ and the alpha-amino protecting group $X^1$, if still present (unless it is an acyl group which is intended to be present in the final peptide), to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate potential S-alkylation.

The cyclizing step for the CRF peptide analog depends, of course, upon the type of linkage which is desired between the residues in the 30- and 33-positions (and similarly for those in the 20- and 23-positions when a bi-cyclic molecule is being formed). When residues of L-Cys are included in both the 30- and 33-positions, it is often more convenient to carry out the cyclizing step following the cleavage from the resin and the removal of all of the protecting groups from the peptide. The cyclic form of the peptide is obtained by oxidization using a ferricyanide solution, preferably as described in Rivier et al., *Biopolymers*, Vol. 17, 1927–38, (1978), or by air oxidation, or in accordance with other known procedures.

To effect an amide cyclizing linkage (lactam bridge), cyclization may be carried out while the partially protected peptide remains attached to the resin as disclosed in U.S. Pat. Nos. 5,064,939 and 5,043,322, the disclosures of which are incorporated herein by reference. Such a procedure effectively creates an amide cyclizing bond between the two desired side chains while other residues, such as Asp, Glu and/or Lys, in the peptide intermediate retain their side-chain protection.

When cyclizing via an amide bond between a side-chain carboxyl group of the 30-position residue and a side-chain amino group of the 33-position residue, or vice-versa which is considered to be an equivalent linkage, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 5,043,322. Preferably cyclization is accomplished by using a base-labile protecting group, e.g., OFm, for the carboxyl side-chain of the residue to be involved in the amide-bond bridge and using Fmoc as a protecting group for the amino side chain on the other residue that is to be involved. The α-amino protecting group on the residue at the N-terminus of the intermediate and all of the other side-chain protecting groups remain in place while the two base-labile groups are removed using piperidine or the like. Following such selective removal, a reaction to accomplish cyclization is carried out by treating with BOP which effects substantially complete generation of the amide bond. If 2 lactam bridges are to be incorporated in the molecule, the 30-33 bridge is preferably effected at a point in the synthesis prior to adding the 23-position residue, or a synthesis protocol such as taught in U.S. Pat. No. 5,064,939 is employed. Following cyclization, the peptide is completely deprotected and cleaved from the resin using a reagent, such as HF. Optionally, a BOC-protecting group is first removed from the N-terminus using TFA, particularly if the N-terminus is to be acylated.

Alternatively, cyclizations of peptides by creating such amide linkages can also be effected using teachings of U.S. Pat. Nos. 4,115,554(Sep. 19, 1978); 4,133,805(Jan. 9, 1979); 4,140,767(Feb. 20, 1979); 4,161,521(Jul. 17, 1979); 4,191,754(Mar. 4, 1980); 4,238,481(Dec. 9, 1980); 4,244,947(Jan. 13, 1981); and 4,261,885(Apr. 14, 1981).

A straightforward in vitro assay can be carried out using rat anterior pituitary cells in monolayer culture to determine what CRF-activity a candidate peptide will exhibit; the procedure which is used is that generally set forth in *Endocrinology*, 91, 562 (1972). The assay will show whether a candidate peptide will exhibit some activity as a CRF agonist and stimulate ACTH secretion by activating CRF receptors on such cells; in this manner its intrinsic CRF activity is measured via the use of high doses. Essentially the same in vitro assay is employed to determine whether the candidate will exhibit strong CRF antagonistic properties when administered together with a challenge dose of CRF, usually either oCRF or r/hCRF.

A candidate CRF antagonist peptide is also readily evaluated in a binding assay using a known CRF receptor, such as that described in Perrin, M., et al., *Endocrinology*, 118, 1171–1179 (1986). The details of binding assays are discussed later in this specification and may be carried out with human CRF-R. Radioligands such as (cyclo 30-33) $[I^{125}$-D-Tyr$^{12}$, Glu$^{30}$, Lys$^{33}$, Nle$^{21,38}$]-r/hCRF(12-41) and its analog having D-His$^{32}$, have high affinity for human CRF-R. For example, the first-named compound has a $K_D$ of 2.0 nanomolar (1.4–2.9) for binding to hCRF-RA1, which is essentially equal to that of the comparable D-Phe$^{12}$ analog. One such representative binding assay utilizing CRF-R receptor is described in Chen, et al., *P.N.A.S.*, 90, 8967–8971 (October 1993). Because certain of these cyclic peptides, particularly those having a D-amino acid residue in position 32, exhibit such high binding affinity for all known CRF receptors, they are especially valuable for use in screening assays. Such assays are advantageously used to screen for potential CRF-like ligands, in peptide or other form, using such a labelled cyclic CRF antagonist with high affinity.

The following Example I sets forth a preferred method for synthesizing CRF antagonists by the solid-phase technique.

EXAMPLE I

The synthesis of the (cyclo 30-33) [D-Phe$^{12}$, Nle$^{21,38}$, Glu$^{30}$, Lys$^{33}$]-r/hCRF(12-41) having the amino acid sequence: (cyclo 30-33)H-D-Phe-His-Leu-Leu-Arg-Glu-Val-Leu-Glu-Nle-Ala-Arg-Ala-Glu-Gln-Leu-Ala-Gln-Glu-Ala-His-Lys-Asn-Arg-Lys-Leu-Nle-Glu-Ile-Ile-NH$_2$ is conducted in a stepwise manner on about 3 grams of a MBHA hydrochloride resin, such as available from Bachem, Inc., having a substitution range of about 0.43 to 0.46 mequiv/gm resin. The synthesis is performed on an automatic Beckman 990B peptide synthesizer using a suitable program, preferably as follows:

| STEP | REAGENTS AND OPERATIONS | MIX TIMES (MIN). |
| --- | --- | --- |
| 1 | CH$_2$Cl$_2$ wash-80 ml. (2 times) | 1 |
| 2 | Methanol(MeOH) wash-30 ml. (2 times) | 1 |
| 3 | CH$_2$Cl$_2$ wash-80 ml. (3 times) | 1 |
| 4 | 50 percent TFA plus 5 percent 1,2-ethane-dithiol in CH$_2$Cl$_2$-70 ml. (2 times) | 12 |
| 5 | Isopropanol wash-80 ml. (2 times) | 1 |
| 6 | TEA 12.5 percent in CH$_2$Cl$_2$-70 ml. (2 times) | 1 |
| 7 | MeOH wash-40 ml. (2 times) | 1 |
| 8 | CH$_2$Cl$_2$ wash-80 ml. (3 times) | 1 |
| 9 | Boc-amino acid (3–5 mmolar excess) in 30 ml. of either DMF or CH$_2$Cl$_2$, depending upon the solubility of the particular protected amino acid, (1 time) plus DCC (3–5 mmolar excess) in CH$_2$Cl$_2$ | 30–300 |

Coupling of BOC-Ile results in the substitution of about 0.35 mmol. Ile per gram of resin.

After deprotection and neutralization, the peptide chain is built step-by-step on the resin. Generally, one to two mmol.

of BOC-protected amino acid in methylene chloride is used per gram of resin (e.g. a 2–5 fold excess depending on substitution of the resin), plus one equivalent of 2 molar DCC in methylene chloride, for two hours. When BOC-Arg (Tos) is being coupled, a mixture of 50% DMF and methylene chloride is used. Bzl is used as the hydroxyl side-chain protecting group for Ser. BOC-Asn(Xan) or BOC-Gln(Xan) is coupled in the presence of one equivalent of DCC and two equivalents of HOBt in a 50% mixture of DMF and methylene chloride. Either 2Cl—Z or Fmoc is used as the protecting group for the Lys side chain depending upon whether it is to be part of a lactam bridge. Tos is used to protect the guanidino group of Arg and the imidazole group of His, and the side chain carboxyl group of Glu is protected by OChx or OFm depending upon whether it is to take part in the cyclizing reaction. At the end of the synthesis, the following composition is obtained: BOC-D-Phe-His(Tos)-Leu-Leu-Arg(Tos)-Glu(OChx)-Val-Leu-Glu(OChx)-Nle-Ala-Arg(Tos)-Ala-Glu(OChx)-Gln(Xan)-Leu-Ala-Gln(Xan)-Glu(OFm)-Ala-His(Tos)-Lys (Fmoc)-Asn(Xan)-Arg (Tos)-Lys(2Cl-Z)-Leu-Nle-Glu (OChx)-Ile-Ile-MBHA resin support.

Next cyclization (lactamization) of residues 30 and 33 is performed by the method referred to hereinbefore and described more fully as follows. After washes with dichloromethane(DCM) (2×) and dimethylformamide (DMF) (2×), the OFmc/Fmoc groups of Glu$^{30}$ and Lys$^{33}$, respectively, are removed by 20% piperidine in DMF (1×1 min. and 2×10 min.), followed by washing with DMF (2×), Et$_3$N in CH$_2$Cl$_2$(1×) methanol(MeOH) (2×) and DCM (2×). The peptide-resin is cyclized by reaction at room temperature with threefold excess of benzotriazol-1-yl-oxy-tris (dimethylamino)phosphonium hexafluorophosphate(BOP) in presence of excess diisoproplyethylamine(DIEA) in dimethylformamide(DMF) for four hours. Other suitable reagents are well known in the art and may alternatively be used. After washing, the cyclization may be repeated if desired to assure completion. The reaction is followed by Kaiser ninhydrin test (E. Kaiser et al., "Color test for detection of free terminal amino groups in the solid-phase synthesis of peptides", *Anal Biochem* (1970) 34:595–98).

After removal of the N$^\alpha$-BOC protecting group, the fully protected peptide-resin is dried. About 2 grams is cleaved by anhydrous HF (20 mL) in the presence of anisole (0.6 mL) at 0° C. for 90 min. The crude peptide is precipitated and washed with anhydrous diethyl ether (450 mL in 3 portions), filtered, extracted from the resin with 380 mL (r portions) of 0.1% TFA in CH$_3$CN/H$_2$O (60:40) and lyophilized to give the crude product.

The crude lyophilized peptide is purified by preparative reverse-phase HPLC (RP-RHPLC) on a system composed of a Waters Associates (Milford, Mass.) Prep LC 3000 System, a Waters Associate 600E System Controller, a Shimadzu SPD-6A UV Spectrophotometric variable-wavelength detector (detection was 230 nm), Waters 1000 PrepPak Module, and a Fisher (Lexington, Mass.) Recordall Series 5000 strip chart recorder (chart speed 0.25 cm/min.). Final peptide purification is carried out in two or three steps using buffers of TEAP pH 2.25, and 0.1% TFA and/or TEAP pH 6.5 and 0.1% TFA.

The crude peptide (about 0.3–1.5 gm) is first dissolved in 400 mL buffer A: triethylammonium phosphate (TEAP) (pH 2.25) (1:4 v/v), loaded on a preparative reversed phase HPLC cartridge (5×30 cm) packed in the laboratory using Waters polyethylene sleeves and frits and Vydac C$_{18}$ silica gel (The Separations Group, Hesperia, Calif.; 300 Å pore size, 15 to 20-μm particle size). The peptide is eluted using buffer B: 60% CH$_3$CN in buffer A with a gradient from 30 to 60% B. Buffers A (triethlyammonium phosphate (TEAP), pH 2.25) and B (CH$_3$CN in A) are pumped at a flow rate of 95 mL/min for 90 minutes. Fractions containing a total of 50–100 mL are screened under isocratic conditions (61% B, retention time about 2.84 min.), and fractions containing the compound are identified and pooled.

In the second step, the pooled fractions are diluted with 160 mL of H$_2$O and eluted by using as buffer A: 0.1% TFA/H$_2$O and B: 0.1% TFA in CH$_3$CN/H$_2$O (60:40), with a gradient from 40 to 70% B in 90 minutes (retention time about 67 min.). Fractions containing a total of 30–50 mL are screened, and fractions containing the compound are pooled and lyophilized to yield the final product peptide. It has a purity of about 98%.

Specific optical rotation at the Sodium D line of the peptide synthesized and purified in this manner is measured on a Perkin Elmer Model 241 Polarimeter as $[\alpha]_D^{22}$=−62.4°±1.0 (c=1 in 1% acetic acid) (without correction for the presence of H$_2$O and TFA). Purity is confirmed by capillary zone electrophoresis (CZE), and identity is confirmed by mass spectroscopy (MS).

The synthesis is repeated without the cyclization step to produce the comparable linear peptide.

In vitro biopotency of the product peptide can be measured as follows. Rat anterior pituitary glands from male Sprague-Dawley rats are dissociated by collagenase and plated (0.16×10$^6$ cells/well in 48-well plates) in medium containing 2% fetal bovine serum (FBS). Three days after plating, the cells are washed three times with fresh medium containing 0.1% bovine serum albumin (BSA) and incubated for 1 hour. Following the 1 hour preincubation, the cells are washed once more, and the test peptides are applied in the presence of 1 nM oCRF. At the end of a 3 hour incubation period the media are collected and the level of ACTH is determined by radioimmunoassay (Diagnostic Products Corporation). The cyclic peptide product of the above described synthesis exhibits biopotency about 33 times greater (12–82, confidence range) than that of the present "Standard" peptide, i.e. [D-Phe$^{12}$, Nle$^{21,38}$]r/hCRF (12-41). The comparable linear peptide is synthesized and found to exhibit a biopotency less than 10% of that of the Standard (0.01–0.16); this constitutes a difference of about 300 times in in vitro potency.

Administration of the peptide inhibits the secretion of ACTH and β-endorphin-like immuno-activities (β-END-LI) and exhibits especially long duration of inhibition. The in vivo assays which are employed to test these CRF antagonists use adrenalectomized (ADX) rats. Adult male Sprague Dawley rats (230–250 g) are adrenalectomized via a lombar approach under halothane anesthesia. Their diet is supplemented with 0.9% NaCl in the drinking water and with oranges. Two days prior to the experiments, the animals are equipped with jugular cannulae, as described in C. Rivier, et al., *Endocrinology*, 110, 272–278 (1982). On the morning of the experiments, the i.v. cannulae are connected to a line filled with heparinized saline, and the rats are placed in individual buckets and left undisturbed for 2 hours. For the experiment, a first blood sample of 0.3 mL is withdrawn, the test solution is injected (in an 0.2–0.5 mL volume), and subsequent blood samples are obtained at about 15, 45, 90 and 120 minutes. The blood samples are centrifuged, and the separated plasma are kept frozen (−20° C.) until assayed for ACTH values. Plasma ACTH levels are measured as described in C. Rivier, et al. *J. Neuroscience*, 14, 1985 (1994).

As a result of in vivo testing at a level of 1 mg/kg of body weight, it is shown that, at 15 minutes time, the cyclic CRF antagonist is more effective than the standard CRF antagonist in reducing ACTH levels in the serum. At 45 minutes following injection, the cyclic compound depresses the ACTH levels even further than at the 15 minute level, while the effect of the standard CRF antagonist has run its course and levels are substantially the same as in the control animals. At 90 minutes, the ACTH levels remain at about this low level for those rats treated with the cyclic compound, well below the level of the control rats and those treated with the standard CRF antagonist. At 120 minutes following injection, the level of ACTH is essentially back to normal. When tested at levels of 0.3 mg/kg of body weight, the results are essentially the same for 15 and 45 minutes; however, at 90 minutes, there is still some improvement over the rats treated with the standard CRF antagonist but it is not as significant as shown when injected at a level of 1 milligram per kg of body weight.

One further series of tests is carried out where rats are injected with the standard CRF antagonist at a level of 3 mg/kg and 2 sets of other rats are injected with the cyclic CRF antagonists at levels of 0.1 mg/kg and 0.03 mg/kg. The results are essentially the same as in the previous two tests at 15 and 45 minutes, with even the 0.03 mg/kg injection showing a significant improvement over the 3 mg/kg injection of the standard CRF antagonist. At 90 minutes, there is still some marginal improvement over the rats injected with the 3 mg/kg of the standard; however, the ACTH levels essentially return to about the levels at the beginning of the test upon the passage of 90 minutes. Tests show that, even when used at a level 1/100 of the amount of the standard CRF antagonist, the cyclic compound still performs substantially better over a 45-minute time span. Collectively, these data show that the cyclic peptide is more than 10 times more potent after intravenous (i.v.) administration in vivo than the laboratory Standard which was one of the best reported in about 1994.

EXAMPLE I A

The synthesis of Example I is repeated using a triple batch and extending the N-terminus instead of terminating the synthesis at D-Phe. Three additional residues are sequentially added, i.e. Thr, Leu and then Asp; after each addition, 1/3 of the original amount of resin is removed. Following cleavage, the following three peptides are produced:
(cyclo 30-33) [D-Phe$^{12}$, Nle$^{21,38}$, Glu$^{30}$, Lys$^{33}$]-r/hCRF(11-41);
(cyclo 30-33) [D-Phe$^{12}$, Nle$^{21,38}$, Glu$^{30}$, Lys$^{33}$]-r/hCRF(10-41); and
(cyclo 30-33) [D-Phe$^{12}$, Nle$^{21,38}$, Glu$^{30}$, Lys$^{33}$]-r/hCRF(9-41).

Specific optical rotation at the Sodium D line is measured for each peptide, as previously described. The results are as follows:

$[\alpha]_D^{22}=-47.6°\pm1.0$ for the CRF(11-41) analog;
$[\alpha]_D^{22}=-38.5°\pm1.0$ for the CRF(10-41) analog; and
$[\alpha]_D^{22}=-35.3°\pm1.0$ for the CRF(9-41) analog, with all three results being for c=1 in 10% acetic acid, without correction for the presence of H$_2$O and TFA. Each peptide has a purity of at least about 95%, as confirmed by capillary zone electrophoresis, and its identity is confirmed by MS. The biopotency of each peptide is measured in vitro, as previously described, compared to the laboratory standard peptide, i.e. [D-Phe$^{12}$, Nle$^{21,38}$]r/hCRF(12-41). The results are set forth below:

the r/hCRF(11-41) analog=40.3 times the Standard (27.78–72.16);
the r/hCRF(10-41) analog=31.6 times the Standard (13.53–65.20); and
the r/hCRF(9-41) analog=33.8 times (12.52–77.05) the Standard.

EXAMPLE I B

The syntheses of Examples I and IA are repeated, each time acetylating the N-terminus using acetic anhydride to produce the following four peptides:
(cyclo 30-33) [Ac-D-Phe$^{12}$, Nle$^{21,38}$, Glu$^{30}$, Lys$^{33}$]-r/hCRF(12-41);
(cyclo 30-33) [Ac-Thr$^{11}$, D-Phe$^{12}$, Nle$^{21,38}$, Glu$^{30}$, Lys$^{33}$]-r/hCRF(11-41);
(cyclo 30-33) [Ac-Leu$^{10}$, D-Phe$^{12}$, Nle$^{21,38}$, Glu$^{30}$, Lys$^{33}$]-r/hCRF(10-41); and
(cyclo 30-33) [Ac-Asp$^9$, D-Phe$^{12}$, Nle$^{21,38}$, Glu$^{30}$, Lys$^{33}$]-r/hCRF(9-41).

Specific optical rotation at the Sodium D line is measured for each peptide, as previously described. The results are as follows:

$[\alpha]_D^{20}=-39.3°\pm1.0$ for the CRF(12-41) analog;
$[\alpha]_D^{20}=-30.8°\pm1.0$ for the CRF(11-41) analog;
$[\alpha]_D^{20}=-29.9°\pm1.0$ for the CRF(10-41) analog; and
$[\alpha]_D^{20}=-31.1°\pm1.0$ for the CRF(9-41) analog, with all four results being for c=1 in 10% acetic acid, without correction for the presence of H$_2$O and TFA. Each peptide has a purity of at least about 95%, as confirmed by capillary zone electrophoresis, and its identity is confirmed by MS. Administration of each peptide inhibits the secretion of ACTH and β-END-LI, with the CRF(11-41) analog exhibiting an in vitro biopotency about 64 times (32.8–128.6) that of the Standard. The CRF(10-41) analog exhibits a biopotency of about 34 times (12.5–77), and the CRF(12-41) analog exhibits a biopotency of 36.5 times (19.23–67.16) that of the Standard. The (9-41) analog surprisingly exhibits a biopotency about 172 times (67.9–522.5) the Standard and more than twice (1.09–3.65) that of Peptide No. I (Astressin).

EXAMPLE I C

The synthesis of Example I is repeated, substituting D-Tyr for D-Phe, to produce the following peptide: (cyclo 30-33) [D-Tyr$^{12}$, Nle$^{21,38}$, Glu$^{30}$, Lys$^{33}$]-r/hCRF(12-41).

Specific optical rotation at the Sodium D line of the peptide is measured, as previously described, as $[\alpha]_D^{22}=-61.4°\pm1.0$ (c=0.5 in 10% acetic acid, without correction for the presence of H$_2$O and TFA). It has a purity of about 98%, further confirmed by CZE. The peptide's biopotency, determined as previously described, is about 5.6 times (3.4–9.4) that of the laboratory Standard, i.e. [D-Phe$^{12}$, Nle$^{21,38}$]rCRF (12-41). A portion of the peptidoresin is acetylated at its N-terminus prior to cleavage to produce the cyclic peptide (cyclo 30-31) [Ac-D-Tyr$^{12}$, Nle$^{21,38}$, Glu$^{30}$, Lys$^{33}$]-r/hCRF (12-41). Both of these cyclic peptides are readily labelled with $^{125}$I and found to be useful in receptor binding assays.

EXAMPLE II

The synthesis of (cyclo 30-33) [D-Phe$^{12}$, Nle$^{21,38}$, Glu$^{30}$, Orn$^{33}$]-r/hCRF(12-41) having the amino acid sequence: (cyclo 30-33)H-D-Phe-His-Leu-Leu-Arg-Glu-Val-Leu-Glu-Nle-Ala-Arg-Ala-Glu-Gln-Leu-Ala-Gln-Glu-Ala-His-Orn-Asn-Arg-Lys-Leu-Nle-Glu-Ile-Ile-NH$_2$ is conducted as described in Example I above, except that residue 33 is Orn instead of Lys. Administration of the peptide inhibits the secretion of ACTH and β-END-LI.

EXAMPLE II A

The synthesis of Example II is repeated, substituting D-Tyr for D-Phe, to produce the following peptide: (cyclo 30-33) [D-Tyr$^{12}$, Nle$^{21,38}$, Glu$^{30}$, Orn$^{33}$]-r/hCRF(12-41), having the amino acid sequence: (cyclo 30-33)H-D-Tyr-His-Leu-Leu-Arg-Glu-Val-Leu-Glu-Nle-Ala-Arg-Ala-Glu-Gln-Leu-Ala-Gln-Glu-Ala-His-Orn-Asn-Arg-Lys-Leu-Nle-Glu-Ile-Ile-NH$_2$.

Administration of the peptide inhibits the secretion of ACTH and β-END-LI. A portion of the peptide is then iodinated with $^{125}$I to provide a ligand for use in competitive drug screening assays.

EXAMPLE II B

The general synthesis of Example I is used to produce the following peptide: (cyclo 30-33) [D-Tyr$^{12}$, Nle$^{21,38}$, Glu$^{30}$, Asn$^{32}$, Lys$^{33}$, Arg$^{36}$]-r/hCRF (12-41), having the amino acid sequence: (cyclo 30-33)H-D-Tyr-His-Leu-Leu-Arg-Glu-Val-Leu-Glu-Nle-Ala-Arg-Ala-Glu-Gln-Leu-Ala-Gln-Glu-Ala-Asn-Lys-Asn-Arg-Arg-Leu-Nle-Glu-Ile-Ile-NH$_2$.

Specific optical rotation at the Sodium D line of the peptide is measured, as previously described, as $[\alpha]_D^{22}=$ 47.0°±1.0 (c=1 in 1% acetic acid, without correction for the presence of H$_2$O and TFA). It has a purity of about 98%, further confirmed by CZE, and its identity is confirmed by MS. The peptide's biopotency, determined as previously described, is about 79 times that of the standard peptide, [D-Phe$^{12}$, Nle$^{21,38}$]rCRF(12-41). The peptide is readily radioiodinated and is useful in drug screening assays.

EXAMPLE II C

The general synthesis as set forth in Example I is used to produce the following peptide: (cyclo 30-33) [D-Tyr$^{12}$, Glu$^{13}$, Lys$^{17,33}$, Nle$^{21,38}$, Glu$^{30}$, Asn$^{32}$, Arg$^{36}$]-r/hCRF(12-41), having the amino acid sequence: (cyclo 30-33)H-D-Tyr-Glu-Leu-Leu-Arg-Lys-Val-Leu-Glu-Nle-Ala-Arg-Ala-Glu-Gln-Leu-Ala-Gln-Glu-Ala-Asn-Lys-Asn-Arg-Arg-Leu-Nle-Glu-Ile-Ile-NH$_2$ (Peptide II C).

Specific optical rotation at the Sodium D line of the peptide is measured, as previously described, as $[\alpha]_D^{22}=$ 47.0°±1.0 (c=1 in 1% acetic acid, without correction for the presence of H$_2$O and TFA). It has a purity of about 98%, further confirmed by capillary zone electrophoresis. The peptide's biopotency, determined as previously described, is about 49 times that of the Standard. The peptide is readily radioiodinated and is useful in drug screening assays.

EXAMPLE II D

The general synthesis of Example I is used to produce the following peptide: (cyclo 30-33) [D-Tyr$^{12}$, Nle$^{21,38}$, Glu$^{30}$, Asn$^{32}$, Lys$^{33}$]-r/hCRF(12-41), having the amino acid sequence: (cyclo 30-33)H-D-Tyr-His-Leu-Leu-Arg-Glu-Val-Leu-Glu-Nle-Ala-Arg-Ala-Glu-Gln-Leu-Ala-Gln-Glu-Ala-Asn-Lys-Asn-Arg-Lys-Leu-Nle-Glu-Ile-Ile-NH$_2$.

Administration of the peptide inhibits the secretion of ACTH and B-END-LI to about the same extent as Peptide II C. The peptide is readily radioiodinated and is useful in drug screening assays.

EXAMPLE III

The peptide (cyclo 30-33) [D-Phe$^{12}$, Nle$^{21,38}$, Cys$^{30,33}$]r/hCRF(12-41) having the amino acid sequence: H-D-Phe-His-Leu-Leu-Arg-Glu-Val-Leu-Glu-Nle-Ala-Arg-Ala-Glu-Gln-Leu-Ala-Gln-Cys-Ala-His-Cys-Asn-Arg-Lys-Leu-Nle-Glu-Ile-Ile-NH$_2$ is synthesized.

The synthesis protocol previously described herein is employed to produce the fully protected peptide-resin which is cleaved by HF. After precipitation and washing with diethyl ether (480 mL in 3 portions), the peptide is extracted with water (200 mL) and 5.0% AcOH (100 mL). The resulting solution is poured into 4.0 L of degassed water and the pH adjusted to 6.8–7.0 with NH$_4$OH. As the mixture becomes cloudy, CH$_3$CN (300 mL) is added to avoid precipitation. The mixture is then stirred at 4° C. under air atmosphere, and after 48 h, cyclization is complete (Ellman test). The pH is adjusted to 5.0 with AcOh, and the resulting solution is loaded on a Bio-Rex-70 column (120 mL). The column is washed with 0.5% AcOH (200 mL), and the peptide elutes with 50% AcOH. Fractions are collected, and those containing ninhydrin-positive material are diluted and lyophilized (80 mg).

Purification is performed in three steps. First the peptide is dissolved in buffer A (TEAP pH 2.25, 300 mL) and eluted by using as buffer B: 60% CH$_3$CN in A, with a gradient from 30 to 60% B in 60 minutes. Fractions are screened under isocratic conditions (53% B) and fractions containing the compound are pooled. In the second step, the pooled fractions are diluted with H$_2$O and eluted using buffer A: TEAP (pH 6.0) and B: 60% CH$_3$CN in A, with a gradient from 30 to 55% B in 60 minutes. Fractions are again screened under isocratic conditions (53% B), and the pooled fractions are diluted with H$_2$O and eluted using buffer A: 0.1% TFA/H$_2$O and B: 0.1% TFA in CH$_3$CN/H$_2$O (60:40), with a gradient from 30 to 60% B in 20 minutes. The fractions containing the product are pooled and lyophilized to yield the product peptide.

Administration of the peptide inhibits the secretion of ACTH and β-END-LI.

EXAMPLE IV

The synthesis of Example I is repeated, substituting D-His for His$^{32}$, to produce the following peptide: (cyclo 30-33) [D-Phe$^{12}$, Nle$^{21,38}$, Glu$^{30}$, D-His$^{32}$, Lys$^{33}$]-r/hCRF(12-41), having the amino acid sequence: (cyclo 30-33)H-D-Phe-His-Leu-Leu-Arg-Glu-Val-Leu-Glu-Nle-Ala-Arg-Ala-Glu-Gln-Leu-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{22}=$ −47.0°±1.0 (c=1 in 10% acetic acid, without correction for the presence of H$_2$O and TFA). It has a purity of about 98%, confirmed by capillary zone electrophoresis. The peptide's biopotency, determined as previously described, is about 80.3 times (41.58–173.2) that of the Standard, [D-Phe$^{12}$, Nle$^{21,38}$]rCRF(12-41). It is sometimes hereinafter referred to as Destressin. In vivo testing shows it to exhibit a capability to suppress the secretion of ACTH in adrenalectomized rats at least about as good as that of Peptide No. 1 and continues to have a measurable effect at 2 hours, at a dosage of about 100 µg/kg.

EXAMPLE IV A

The synthesis of Example I is repeated, substituting D-Tyr for D-Phe and substituting D-His for His$^{32}$, to produce the following peptide: (cyclo 30-33) [D-Tyr$^{12}$, Nle$^{21,38}$, Glu$^{30}$, D-His$^{32}$, Lys$^{33}$]-r/hCRF(12-41), having the amino acid sequence: (cyclo 30-33)H-D-Tyr-His-Leu-Leu-Arg-Glu-Val-Leu-Glu-Nle-Ala-Arg-Ala-Glu-Gln-Leu-Ala-Gln-Glu-Ala-D-His-Lys-Asn-Arg-Lys-Leu-Nle-Glu-Ile-Ile-NH$_2$.

Administration of the peptide inhibits the secretion of ACTH and β-END-LI. A portion of the peptide is iodinated with $^{125}$I to provide a ligand for use in competitive drug screening assays and shows high binding affinity to CRF receptors.

EXAMPLE IV B

The synthesis of Example IV is repeated, but acetylating the N-terminus, to produce the following peptide: (cyclo 30-33) [Ac-D-Phe$^{12}$, Nle$^{21,38}$, Glu$^{30}$, D-His$^{32}$, Lys$^{33}$]-r/hCRF(12-41), having the amino acid sequence: (cyclo 30-33)Ac-D-Phe-His-Leu-Leu-Arg-Glu-Val-Leu-Glu-Nle-Ala-Arg-Ala-Glu-Gln-Leu-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=$ 30.1°±1.0 (c=1 in 10% acetic acid, without correction for the presence of H$_2$O and TFA). It has a purity of about 98%, as determined by HPLC and confirmed by capillary zone electrophoresis. The peptide's biopotency, determined as previously described, is about 1.24 times (0.41–3.34) that of the Peptide IV (Destressin). In vivo testing shows that it is slightly more biopotent in the suppression of secretion of ACTH than Destressin at 1, 1½ and 2 hours.

EXAMPLE IV C

The synthesis of Example IV is repeated, but elongating the N-terminus by the addition of Thr, to produce the following peptide: (cyclo 30-33) [D-Phe$^{12}$, Nle$^{21,38}$, Glu$^{30}$, D-His$^{32}$, Lys$^{33}$]-r/hCRF(11-41), having the amino acid sequence: (cyclo 30-33)H-Thr-D-Phe-His-Leu-Leu-Arg-Glu-Val-Leu-Glu-Nle-Ala-Arg-Ala-Glu-Gln-Leu-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=-$39.1°±1.0 (c=1 in 10% acetic acid, without correction for the presence of H$_2$O and TFA). It has a purity of about 98%, confirmed by capillary zone electrophoresis. The peptide's biopotency, determined as previously described, is about 0.78 times (0.41–1.46) that of the Peptide IV.

EXAMPLE IV D

The synthesis of Example IV is repeated, but elongating the N-terminus by adding Thr and then acetylating it, to produce the following peptide: (cyclo 30-33) [Ac-Thr$^{11}$, D-Phe$^{12}$, Nle$^{21,38}$, Glu$^{30}$, D-His$^{32}$, Lys$^{33}$]-r/hCRF(11-41), having the amino acid sequence: (cyclo 30-33)Ac-Thr-D-Phe-His-Leu-Leu-Arg-Glu-Val-Leu-Glu-Nle-Ala-Arg-Ala-Glu-Gln-Leu-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=-$23.0°±1.0 (c=1 in 10% acetic acid, without correction for the presence of H$_2$O and TFA). It has a purity of about 98%, confirmed by capillary zone electrophoresis. The peptide's biopotency, determined as previously described, is about 3.08 times (1.06–7.84) that of the Peptide IV.

EXAMPLE V

The synthesis of (cyclo 30-33) [D-Phe$^{12}$, Nle$^{21,38}$, Glu$^{30}$, D-His$^{32}$, Orn$^{33}$]-r/hCRF(12-41) having the amino acid sequence: (cyclo 30-33)H-D-Phe-His-Leu-Leu-Arg-Glu-Val-Leu-Glu-Nle-Ala-Arg-Ala-Glu-Gln-Leu-Ala-Gln-Glu-Ala-D-His-Orn-Asn-Arg-Lys-Leu-Nle-Glu-Ile-Ile-NH$_2$ is conducted as described in Example I above, except that residue 33 is Orn instead of Lys. Administration of the peptide inhibits the secretion of ACTH and β-END-LI.

EXAMPLE V A

The synthesis of Example I is repeated, substituting D-Arg for His$^{32}$, to produce the following peptide: (cyclo 30-33) [D-Phe$^{12}$, Nle$^{21,38}$, Glu$^{30}$, D-Arg$^{32}$, Lys$^{33}$]-r/hCRF (12-41), having the amino acid sequence: (cyclo 30-33)H-D-Phe-His-Leu-Leu-Arg-Glu-Val-Leu-Glu-Nle-Ala-Arg-Ala-Glu-Gln-Leu-Ala-Gln-Glu-Ala-D-Arg-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=-$53.7°±1.0 (c=1 in 10% acetic acid, without correction for the presence of H$_2$O and TFA). It has a purity of about 98%, further confirmed by capillary zone electrophoresis. The peptide's biopotency, determined as previously described, is about 60 times that of the Standard.

EXAMPLE V B

The synthesis of Example I is repeated, substituting D-2Nal for His$^{32}$, to produce the following peptide: (cyclo 30-33) [D-Phe$^{12}$, Nle$^{21,38}$, Glu$^{30}$, D-2Nal$^{32}$, Lys$^{33}$]-r/hCRF (12-41), having the amino acid sequence: (cyclo 30-33)H-D-Phe-His-Leu-Leu-Arg-Glu-Val-Leu-Glu-Nle-Ala-Arg-Ala-Glu-Gln-Leu-Ala-Gln-Glu-Ala-D-2Nal-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=-$40.9°1.0 (c=1 in 10% acetic acid, without correction for the presence of H$_2$O and TFA). It has a purity of about 98%, confirmed by capillary zone electrophoresis. The peptide's biopotency, determined as previously described, is about 18 times that of the Standard.

EXAMPLE V C

The synthesis of Example I is repeated, substituting imBzlD-His for His$^{32}$ and C$^\alpha$MeLeu for Leu$^{15}$, to produce the following peptide: (cyclo 30-33) [D-Phe$^{12}$, CML$^{15}$, Nle$^{21,38}$, Glu$^{30}$, imBzlD-His$^{32}$, Lys$^{33}$]-r/hCRF (12-41), having the amino acid sequence: (cyclo 30-33)H-D-Phe-His-Leu-CML-Arg-Glu-Val-Leu-Glu-Nle-Ala-Arg-Ala-Glu-Gln-Leu-Ala-Gln-Glu-Ala-imBzlD-His-Lys-Asn-Arg-Lys-Leu-Nle-Glu-Ile-Ile-NH$_2$.

Specific optical rotation at the Sodium D line of the peptide is measured, as previously described, as $[\alpha]_D^{20}-$34.2°±1.0 (c=1 in 10% acetic acid, without correction for the presence of H$_2$O and TFA). It has a purity of about 98%, confirmed by capillary zone electrophoresis. The peptide's biopotency, determined as previously described, is about 23.5 times (14.4–39.3) that of the Standard.

EXAMPLE V D

The synthesis of Example I is repeated, substituting D-Glu for His$^{32}$, to produce the following peptide: (cyclo 30-33) [D-Phe$^{12}$, Nle$^{21,38}$, Glu$^{30}$, D-Glu$^{32}$, Lys$^{33}$]-r/hCRF (12-41), having the amino acid sequence: (cyclo 30-33)H-D-Phe-His-Leu-Leu-Arg-Glu-Val-Leu-Glu-Nle-Ala-Arg-Ala-Glu-Gln-Leu-Ala-Gln-Glu-Ala-D-Glu-Lys-Asn-Arg-Lys-Leu-Nle-Glu-Ile-Ile-NH$_2$.

Specific optical rotation at the Sodium D line of the peptide is measured, as previously described, as $[\alpha]_D^{20}-$48.6°±1.0 (c=1 in 10% acetic acid, without correction for the presence of H$_2$O and TFA). It has a purity of about 98%, confirmed by capillary zone electrophoresis. The peptide's biopotency, determined as previously described, is about 10 times that of the Standard.

EXAMPLE VI

The synthesis of (bicyclo 20-23, 30-33) [D-Phe$^{12}$, Nle$^{21,38}$, Lys$^{23,33}$, Glu$^{30}$]-r/hCRF(12-41) having the amino acid sequence: (bicyclo 20-23, 30-33)H-D-Phe-His-Leu-Leu-Arg-Glu-Val-Leu-Glu-Nle-Ala-Lys-Ala-Glu-Gln-Leu-Ala-Gln-Glu-Ala-His-Lys-Asn-Arg-Lys-Leu-Nle-Glu-Ile-Ile-NH$_2$ is conducted as generally described in Example I above, except that the lactam bridge between residues 30 and 33 is completed before residue 23 is added to the peptide-resin.

The optical rotation is measured using the procedure and conditions set forth and is found to be: $[\alpha]_D^{20}=-42.0°\pm1.0$ (c=0.5 in 10% acetic acid, without correction for the presence of H$_2$O and TFA). MS is measured as 3515.95 which is in agreement with the calculated value of 3516.03.

In vitro testing as described in Example I shows a potency about 8.3 times (3.65–18.32) that of the Standard. Administration of the peptide inhibits the secretion of ACTH and β-END-LI.

EXAMPLE VI A

The synthesis of (bicyclo 20-23, 30-33) [D-Phe$^{12}$, Nle$^{21,38}$, D-Ala$^{22}$, LyS$^{23,33}$, Glu$^{30}$, D-His$^{32}$]-r/hCRF(12-41) having the amino acid sequence: (bicyclo 20-23, 30-33)H-D-Phe-His-Leu-Leu-Arg-Glu-Val-Leu-Glu-Nle-D-Ala-Lys-Ala-Glu-Gln-Leu-Ala-Gln-Glu-Ala-D-His-Lys-Asn-Arg-Lys-Leu-Nle-Glu-Ile-Ile-NH$_2$ is conducted as generally described in Example VI above, except that D-His is substituted for His$^{32}$ and D-Ala is substituted for Ala$^{22}$.

The specific mass of the peptide is measured by LSIMS as 3516.02 which is in agreement with the calculated value of 3516.03. It has a purity of about 98% and the peptide's biopotency, determined as previously described, is about 8.61 times (4.61–15.70) that of the Standard with respect to inhibition of the secretion of ACTH.

EXAMPLE VII

The peptide (cyclo 30-33) [D-Phe$^{12}$, Nle$^{21,38}$, Cys$^{30,33}$, D-His$^{32}$]r/hCRF(12-41) having the amino acid sequence: H-D-Phe-His-Leu-Leu-Arg-Glu-Val-Leu-Glu-Nle-Ala-Arg-Ala-Glu-Gln-Leu-Ala-Gln-Cys-Ala-D-His-Cys-Asn-Arg-Lys-Leu-Nle-Glu-Ile-Ile-NH$_2$ is synthesized.

The synthesis protocol previously described in Example III is employed to produce the fully protected peptide-resin which is cleaved by HF, cyclized, purified, and then lyophilized to yield the product peptide.

The synthesis is repeated to yield the peptide: (cyclo 30-33) (D-Phe$^{12}$, Nle$^{21,38}$, Cys$^{30,33}$, D-2Nal$^{32}$]r/hCRF(12-41)

Administration of each of the peptide antagonists inhibits the secretion of ACTH and β-END-LI.

EXAMPLE VII A

The peptide (cyclo 30-33) [D-Phe$^{12}$, Nle$^{18,21}$, Glu$^{30}$, D-His$^{32}$, Lys$^{33}$]-Carp Urotensin I(12-41) having the formula: H-D-Phe-His-Leu-Leu-Arg-Asn-Nle-Ile-Glu-Nle-Ala-Arg-Asn-Glu-Asn-Gln-Arg-Glu-Glu-Ala-D-His-Lys-Asn-Arg-Lys-Tyr-Leu-Asp-Glu-Val-NH$_2$ is synthesized. Testing in accordance with the general procedure set forth in Example I shows that the cyclic compound inhibits the secretion of ACTH and β-END-LI.

The synthesis is repeated to yield the peptide: (cyclo 30-33) [D-Phe$^{12}$, Nle$^{18,21}$, Glu$^{30}$, D-Ala$^{32}$, Lys$^{33}$]-Carp Urotensin I (12-41). LSIMS shows a value of 3663.09 which corresponds to the calculated value of 3662.96. The peptide's biopotency measures about 0.831 times (0.334–1.978) that of Peptide No. IV.

EXAMPLE VII B

The peptide (cyclo 29-32) [D-Leu$^{11}$, Nle$^{17}$, Glu$^{29}$, D-His$^{31}$, Lys$^{32}$]-sauvagine(11-40) having the formula: H-D-Leu-Glu-Leu-Leu-Arg-Lys-Nle-Ile-Glu-Ile-Glu-Lys-Gln-Glu-Lys-Glu-Lys-Gln-Glu-Ala-D-His-Lys-Asn-Arg-Leu-Leu-Leu-Asp-Thr-Ile-NH$_2$ is synthesized. Testing in accordance with the general procedure set forth in Example I shows that the cyclic compound inhibits the secretion of ACTH and β-END-LI.

The synthesis is repeated to yield the peptide: (cyclo 29-32) [D-Leu$^{11}$, Nle$^{17}$, Glu$^{29}$, D-Ala$^{31}$, Lys$^{32}$]-Sauvagine (11-40). LSIMS shows a value of 3586.15 which corresponds to the calculated value of 3586.11. The peptide's biopotency measures about 15 times that of the Standard.

EXAMPLE VII C

The peptide (cyclo 30-33) [D-Phe$^{12}$, Glu$^{30}$, D-His$^{32}$, Lys$^{33}$]-α-helical CRF(12-41) having the formula: H-D-Phe-His-Leu-Leu-Arg-Glu-Met-Leu-Glu-Met-Ala-Lys-Ala-Glu-Gln-Glu-Ala-Glu-Glu-Ala-D-His-Lys-Asn-Arg-Leu-Leu-Leu-Glu-Glu-Ala-NH$_2$ is synthesized.

Testing in accordance with the general procedure set forth in Example I shows that the cyclic compound inhibits the secretion of ACTH and β-END-LI.

EXAMPLE VII D

The peptide (cyclo 30-33) [D-Phe$^{12}$, Nle$^{18,21}$, Glu$^{30}$, Lys$^{33}$]-Sucker Urotensin I(12-41) having the formula: H-D-Phe-His-Leu-Leu-Arg-Asn-Nle-Ile-Glu-Nle-Ala-Arg-Ile-Glu-Asn-Glu-Arg-Glu-Glu-Ala-Gly-Lys-Asn-Arg-Lys-Tyr-Leu-Asp-Glu-Val-NH$_2$ is synthesized.

LSIMS shows a value of 3648.98 which corresponds to the calculated value of 3648.97. The peptide's biopotency to inhibit the secretion of ACTH and β-END-LI measures about 1.32 times (0.697–2.334) that of Peptide No. IV.

EXAMPLE VII E

The peptide (cyclo 29-32) [D-Leu$^{11}$, Nle$^{17}$, Glu$^{29}$, Lys$^{32}$]-sauvagine(11-40) having the formula: H-D-Leu-Glu-Leu-Leu-Arg-Lys-Nle-Ile-Glu-Ile-Glu-Lys-Gln-Glu-Lys-Glu-Lys-Gln-Glu-Ala-Ala-Lys-Asn-Arg-Leu-Leu-Leu-Asp-Thr-Ile-NH$_2$ is synthesized. LSIMS shows a value of 3586.11 which corresponds exactly to the calculated value of 3586.11. The peptide's biopotency to inhibit the secretion of ACTH and β-END-LI measures about 22 times that of the Standard.

EXAMPLE VIII

The synthesis of Example IV is repeated, substituting C$^\alpha$MeLeu for Leu$^{15}$, to produce the following peptide: (cyclo 30-33) [D-Phe$^{12}$, CML$^{15}$, Nle$^{21,38}$, Glu$^{30}$, D-His$^{32}$, Lys$^{33}$]-r/hCRF(12-41), having the formula: (cyclo 30-33)H-D-Phe-His-Leu-CML-Arg-Glu-Val-Leu-Glu-Nle-Ala-Arg-Ala-Glu-Gln-Leu-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{22}=-39.4°\pm1.0$ (c=0.5 in 10% acetic acid, without correction for the presence of H$_2$O and TFA). It has a purity of about 98%, confirmed by capillary zone electrophoresis. The peptide's biopotency, determined as previously described, is about 20.3 times (11.5–37.0) that of the Standard.

EXAMPLE VIII A

The synthesis of Example IV is repeated, substituting C$^\alpha$MeLeu for Leu$^{14}$, to produce the following peptide: (cyclo 30-33) [D-Phe$^{12}$, CML$^{14}$, Nle$^{21,38}$, Glu$^{30}$, D-His$^{32}$, Lys$^{33}$]-r/hCRF(12-41), having the formula: (cyclo 30-33)H-D-Phe-His-CML-Leu-Arg-Glu-Val-Leu-Glu-Nle-Ala-Arg-Ala-Glu-Gln-Leu-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{22}=-31.6°\pm1.0$ (c=1 in 1% acetic acid, without correction for the presence of H$_2$O and TFA). It has a purity of about 98%, confirmed by capillary zone electrophoresis. The peptide's biopotency, determined as previously described, is about 15 times (7.47–29.33) that of the Standard.

EXAMPLE VIII B

The synthesis of Example IV is repeated, substituting C$^\alpha$MeLeu for Leu$^{19}$, to produce the following peptide: (cyclo 30-33) [D-Phe$^{12}$, CML$^{19}$, Nle$^{21,38}$, Glu$^{30}$, D-His$^{32}$, Lys$^{33}$]-r/hCRF(12-41), having the formula: (cyclo 30-33)H-D-Phe-His-Leu-Leu-Arg-Glu-Val-CML-Glu-Nle-Ala-Arg-Ala-Glu-Gln-Leu-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{22}=-35.3°\pm1.0$ (c=1 in 1% acetic acid, without correction for the presence of H$_2$O and TFA). It has a purity of about 98%, confirmed by capillary zone electrophoresis. The peptide's biopotency, determined as previously described, is about 4.5 times that of the Standard.

EXAMPLE VIII C

The synthesis of Example IV is repeated, substituting C$^\alpha$MeLeu for Leu$^{27}$, to produce the following peptide: (cyclo 30-33) [D-Phe$^{12}$, Nle$^{21,38}$, CML$^{27}$, Glu$^{30}$, D-His$^{32}$, Lys$^{33}$]-r/hCRF(12-41), having the formula: (cyclo 30-33)H-D-Phe-His-Leu-Leu-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{22}=-39.1°\pm1.0$ (c=1 in 1% acetic acid, without correction for the presence of H$_2$O and TFA). It has a purity of about 98%, confirmed by capillary zone electrophoresis. The peptide's biopotency, determined as previously described, is about 53.6 (26.4–112.3) times that of the Standard. It is sometimes referred to as Mestressin. When tested in vivo, it is found to be significantly better than Destressin after 1 and 1½ hours and slightly better after 2 hours in the suppression of ACTH secretion in adrenalectomized rats at a dosage of about 100 µg/kg.

EXAMPLE VIII D

The synthesis of Example IV is repeated, substituting C$^\alpha$MeLeu for Leu$^{37}$, to produce the following peptide: (cyclo 30-33) [D-Phe$^{12}$, Nle$^{21,38}$, Glu$^{30}$, D-His$^{32}$, Lys$^{33}$, CML$^{37}$]-r/hCRF(12-41), having the formula: (cyclo 30-33) H-D-Phe-His-Leu-Leu-Arg-Glu-Val-Leu-Glu-Nle-Ala-Arg-Ala-Glu-Gln-Leu-Ala-Gln-Glu-Ala-D-His-Lys-Asn-Arg-Lys-CML-Nle-Glu-Ile-Ile-NH$_2$.

Specific optical rotation at the Sodium D line of the peptide is measured, as previously described, as $[\alpha]_D^{22}=-31.8°\pm1.0$ (c=1 in 1% acetic acid, without correction for the presence of H$_2$O and TFA). It has a purity of about 98%, confirmed by CZE. The peptide's biopotency, determined as previously described, is about 16 times that of the Standard.

EXAMPLE IX

The synthesis of Example IV is repeated, substituting C$^\alpha$MeLeu for Leu$^{27}$ and acetylating the N-terminus, to produce the following peptide: (cyclo 30-33) [Ac-D-Phe$^{12}$, Nle$^{21,38}$, CML$^{27}$, Glu$^{30}$, D-His$^{32}$, Lys$^{33}$]-r/hCRF(12-41), having the formula: (cyclo 30-33)Ac-D-Phe-His-Leu-Leu-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=-33.7°\pm1.0$ (c=1 in 10% acetic acid, without correction for the presence of H$_2$O and TFA). It has a purity of about 98%, confirmed by CZE. MS is measured as 3618.00 which is in agreement with the calculated value of 3618.08. The peptide's biopotency, determined as previously described, is about 43 times that of the Standard.

EXAMPLE IX A

The synthesis of Example IV is repeated, substituting C$^\alpha$MeLeu for Leu$^{27}$ and elongating the N-terminus by the addition of Thr, to produce the following peptide: (cyclo 30-33) [D-Phe$^{12}$, Nle$^{21,38}$, CML$^{27}$, Glu$^{30}$, D-His$^{32}$, Lys$^{33}$]-r/hCRF(11-41), having the formula: (cyclo 30-33)H-Thr-D-Phe-His-Leu-Leu-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=-41.0°\pm1.0$ (c=1 in 10% acetic acid, without correction for the presence of H$_2$O and TFA). It has a purity of about 98%, confirmed by CZE, and its identity is confirmed by MS. The peptide's biopotency, determined as previously described, is about 1.26 times (0.74–2.15) that of Peptide IV.

EXAMPLE IX B

The synthesis of Example IV is repeated, substituting C$^\alpha$MeLeu for Leu$^{27}$, elongating the N-terminus by the addition of Thr and then acetylating it, to produce the following peptide: (cyclo 30-33) [Ac-Thr$^{11}$, D-Phe$^{12}$, Nle$^{21,38}$, CML$^{27}$, Glu$^{30}$, D-His$^{32}$, Lys$^{33}$]-r/hCRF(11-41), having the formula: (cyclo 30-33)Ac-Thr-D-Phe-His-Leu-Leu-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=23.7°\pm1.0$ (c=1 in 10% acetic acid, without correction for the presence of H$_2$O and TFA). It has a purity of about 98%, confirmed by CZE, and its identity is confirmed by Ms. The peptide's biopotency, determined as previously described, is about 1.40 times (0.74–2.73) that of Peptide IV (Destressin). In vivo testing in adrenalectomized rats shows that it is more effective in suppressing secretion of ACTH than Destressin at 90 and 120 minutes when administered at a dosage of about 100 µg per kg.

EXAMPLE IX C

The synthesis of Example I is repeated, substituting C$^\alpha$MeLeu for Leu$^{27}$ and acetylating the N-terminus, to produce the following peptide: (cyclo 30-33) [Ac-D-Phe$^{12}$, Nle$^{21,38}$, CML$^{27}$, Glu$^{30}$, Lys$^{33}$]-r/hCRF(12-41), having the formula: (cyclo 30-33)Ac-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

Specific optical rotation at the Sodium D line of the peptide is measured, as previously described, as $[\alpha]_D^{20}=-43.8°\pm1.0$ (c=1 in 10% acetic acid, without correction for the presence of H$_2$O and TFA). It has a purity of about 98%, confirmed by CZE, and its identity is confirmed by MS. The peptide's biopotency, determined as previously described, is about 1.65 times (0.59–4.12) that of Peptide IV (Destressin).

EXAMPLE X

Using the procedure as generally set forth in Example I, the following CRF antagonist peptides are also prepared:

(c 30-33) [D-Phe$^{12}$, Nle$^{21,38}$, Glu$^{30}$, Lys$^{33}$]-AHC(9-41)
(c 30-33) [Glu$^{30}$, Lys$^{33}$, Aib$^{34}$]-AHC(12-41)
(c 30-33) [D-Phe$^{12}$, Glu$^{30}$, Lys$^{33}$]-oCRF(10-41)
(c 30-33) [Glu$^{30}$, Lys$^{33}$, Nle$^{21,38}$]-r/hCRF(12-41)
(c 30-33) [D-Phe$^{12}$, Glu$^{30}$, Lys$^{33}$]-oCRF(12-41)
(c 30-33) [Nle$^{18,21}$, Glu$^{30}$, Lys$^{33}$]-AHC(10-41)
(c 30-33) [D-Phe$^{12}$, Glu$^{30}$, Lys$^{33}$]-r/hCRF(12-41)
(c 30-33) [D-Phe$^{12}$, Nle$^{21}$, Glu$^{30}$, Lys$^{33}$, Aib$^{34}$]-oCRF(12-41)
(c 30-33) [D-Phe$^{12}$, Glu$^{30}$, Lys$^{33}$]-AHC(12-41)
(c 30-33) [D-Phe$^{12}$, Nle$^{21,38}$, Aib$^{22}$, Glu$^{30}$, Lys$^{33}$]-r/hCRF(12-41)
(c 30-33) [D-Phe$^{12}$, Nle$^{21,38}$, Aib$^{24}$, Glu$^{30}$, Lys$^{33}$]-rCRF(12-41)
(c 30-33) [D-Phe$^{12}$, Nle$^{21,38}$, Aib$^{28}$, Glu$^{30}$, Lys$^{33}$]-r/hCRF(12-41)
(c 30-33) [D-Phe$^{12}$, Nle$^{21,38}$, Aib$^{29}$, Glu$^{30}$, Lys$^{33}$]-r/hCRF(12-41)
(c 30-33) [D-Phe$^{12}$, Nle$^{21,38}$, Glu$^{30}$, Aib$^{31}$, Lys$^{33}$]-r/hCRF(12-41)
(c 30-33) [D-Phe$^{12}$, Nle$^{21,38}$, Glu$^{30}$, Aib$^{32}$, Lys$^{33}$]-r/hCRF(12-41)
(c 30-33) [D-Phe$^{12}$, Nle$^{21,38}$, Glu$^{30}$, Lys$^{33}$, Aib$^{34}$]-r/hCRF(12-41)
(c 30-33) [D-Phe$^{12}$, Nle$^{21,38}$, Glu$^{30}$, Lys$^{33}$, Aib$^{39}$]-r/hCRF(12-41)
(c 30-33) [D-Phe$^{12}$, Nle$^{21,38}$, Glu$^{30}$, Lys$^{33}$, Aib$^{40}$]-r/hCRF(12-41)
(c 30-33) [Nle$^{18,21}$, Glu$^{30}$, D-His$^{32}$, Lys$^{33}$]-AHC(11-41)
(c 30-33) [D-Phe$^{12}$, Glu$^{30}$, Lys$^{33}$, Aib$^{34}$]-r/hCRF(12-41)
(c 30-33) [Nle$^{21,38}$, Glu$^{30}$, Lys$^{33}$]-r/hCRF(10-41)
(c 30-33) [D-Tyr$^{12}$, Nle$^{21,38}$, Glu$^{30}$, Lys$^{33}$, Aib$^{39}$]-oCRF(9-41)
(c 30-33) [Nle$^{21,38}$, Glu$^{30}$, D-His$^{32}$, Lys$^{33}$]-r/hCRF(9-41)
(c 30-33) [D-4ClPhe$^{12}$, Nle$^{18,21}$, Aib$^{22}$, Glu$^{30}$, Lys$^{33}$]-AHC(12-41)
(c 30-33) [Tyr$^{13}$, Nle$^{21}$, Glu$^{30}$, Lys$^{33}$, CML$^{37}$]-oCRF(11-41)
(c 30-33) [CML$^{17}$, Nle$^{21,38}$, Glu$^{30}$, Lys$^{33}$, CML$^{37}$]-oCRF(10-41)
(c 30-[D-3Pal$^{12}$, Nle$^{21,38}$, Aib$^{24}$, Glu$^{30}$, Lys$^{33}$, CML$^{37}$]-oCRF(12-41)

These peptides are biopotent in inhibiting the secretion of ACTH and β-END-LI in response to various stimuli.

EXAMPLE XI

Using the procedure as generally set forth in Example I, the following CRF antagonist peptides are also prepared:

(c 30-33) [CML$^{17}$, Glu$^{30}$, Lys$^{33}$]-AHC(12-41)
(c 30-33) [CML$^{17}$, Glu$^{30}$, Lys$^{33}$]-oCRF(10-41)
(c 30-33) [D-Phe$^{12}$, CML$^{14}$, Nle$^{21,38}$, Glu$^{30}$, Lys$^{33}$]-r/hCRF(12-41)
(c 30-33) [D-2Nal$^{12}$, CML$^{14}$, Glu$^{30}$, Lys$^{33}$]-oCRF(12-41)
(c 30-33) [CML$^{17}$, Nle$^{18,21}$, Glu$^{30}$, Lys$^{33}$]-AHC(10-41)
(c 30-33) [D-Leu$^{12}$, CML$^{17}$, Glu$^{30}$, Lys$^{33}$]-r/hCRF(12-41)
(c 30-33) [D-Phe$^{12}$, CML$^{17,37}$, Nle$^{21}$, Glu$^{30}$, Lys$^{33}$]-oCRF(12-41)
(c 30-33) [D-4ClPhe$^{12}$, CML$^{15}$, Glu$^{30}$, Lys$^{33}$]-AHC(12-41)
(c 30-33) [D-Phe$^{12}$, CML$^{15}$, Nle$^{21,38}$, Glu$^{30}$, Lys$^{33}$]-r/hCRF(12-41)
(c 30-33) [D-Phe$^{12}$, CML$^{17}$, Nle$^{21,38}$, Glu$^{30}$, Lys$^{33}$]-r/hCRF(11-41)
(c 30-33) [D-Phe$^{12}$, CML$^{17,37}$, Nle$^{21,38}$, Glu$^{30}$, Lys$^{33}$]-r/hCRF(12-41)
(c 30-33) [Nle$^{18,21}$, CML$^{17,37}$, Glu$^{30}$, D-His$^{32}$, Lys$^{33}$]-AHC(11-41)
(c 30-33) [D-Phe$^{12}$, CML$^{17,37}$, Glu$^{30}$, Lys$^{33}$, Aib$^{34}$]-r/hCRF(12-41)
(c 30-33) [CML$^{17,37}$, Nle$^{21,38}$, Glu$^{30}$, Lys$^{33}$]-r/hCRF(10-41)
(c 30-33) [D-Phe$^{12}$, CML$^{19}$, Glu$^{30}$, Lys$^{33}$]-r/hCRF(12-41)
(c 30-33) [D-Pal$^{12}$, Nle$^{21}$, CML$^{27,37}$, Glu$^{30}$, Lys$^{33}$]-oCRF(12-41)
(c 30-33) [D-Tyr$^{12}$, CML$^{27}$, Glu$^{30}$, Lys$^{33}$]-AHC(12-41)
(c 30-33) [D-Phe$^{12}$, CML$^{19}$, Nle$^{21,38}$, Glu$^{30}$, Lys$^{33}$]-r/hCRF(12-41)
(c 30-33) [D-Phe$^{12}$, Nle$^{21,38}$, CML$^{27}$, Glu$^{30}$, Lys$^{33}$]-r/hCRF(12-41)
(c 30-33)[D-Phe$^{12}$, CML$^{19,37}$, Nle$^{21,38}$, Lys$^{23}$, Glu$^{30}$, Lys$^{33}$]-r/hCRF(12-41)

These peptides are biopotent in inhibiting the secretion of ACTH and β-END-LI in response to various stimuli.

EXAMPLE XII

Using the procedure as generally set forth in Example I, the following CRF antagonist peptides are also prepared:

(c 30-33) [Glu$^{30}$, D-His$^{32}$, Lys$^{33}$]-AHC(12-41)
(c 30-33) [CML$^{17}$, Glu$^{30}$, D-Ala$^{32}$, Lys$^{33}$]-oCRF(10-41)
(c 30-33) [D-Tyr$^{12}$, CML$^{14}$, Nle$^{21,38}$, Glu$^{30}$, D-Tyr$^{32}$, Lys$^{33}$]-r/hCRF(12-41)
(c 30-33) [D-2Nal$^{12}$, CML$^{14}$, Glu$^{30}$, D-2Nal$^{32}$, Lys$^{33}$]-oCRF(12-41)
(c 30-33) [CML$^{17}$, Nle$^{18,21}$, Glu$^{30}$, D-Arg$^{32}$, Lys$^{33}$]-AHC(10-41)
(c 30-33) [D-Tyr$^{12}$, Glu$^{30}$, D-Leu$^{32}$, Lys$^{33}$]-r/hCRF(12-41)
(c 30-33) [D-Phe$^{12}$, CML$^{17,37}$, Nle$^{21}$, Glu$^{30}$, Tyr$^{32}$, Lys$^{33}$]-oCRF(12-41)
(c 30-33) [D-4Cpa$^{12}$, Glu$^{30}$, Arg$^{32}$, Lys$^{33}$]-AHC(11-41)
(c 30-33) [D-Tyr$^{12}$, CML$^{15}$, Nle$^{21,38}$, Glu$^{30}$, D-Val$^{32}$, Lys$^{33}$]-r/hCRF(12-41)
(c 30-33) [D-Tyr$^{12}$, Nle$^{21,38}$, Glu$^{30}$, D-Ser$^{32}$, Lys$^{33}$]-r/hCRF(12-41)
(c 30-33) [Ac-Thr$^{11}$, D-Leu$^{12}$, CML$^{17,37}$, Nle$^{21,38}$, Glu$^{30}$, D-Asn$^{32}$, Lys$^{33}$]-r/hCRF(11-41)
(c 30-33) [Nle$^{18,21}$, Glu$^{30}$, D-4Cpa$^{32}$, Lys$^{33}$]-AHC(11-41)
(c 30-33) [(D-Tyr$^{12}$, CML$^{17}$, Glu$^{30}$, D-3Pal$^{32}$, Lys$^{33}$, Aib$^{34}$]-r/hCRF(12-41)
(c 30-33) [CML$^{17,37}$, Nle$^{21,38}$, Glu$^{30}$, Aib$^{32}$, Lys$^{33}$]-r/hCRF(10-41)
(c 30-33) [D-Phe$^{12}$, CML$^{19}$, Glu$^{30}$, D-Lys$^{32}$, Lys$^{33}$]-r/hCRF(12-41)
(c 30-33) [Ac-Ser$^{11}$, D-Pal$^{12}$, Nle$^{21}$, CML$^{27,37}$, Glu$^{30}$, D-Phe$^{32}$, Lys$^{33}$]-oCRF(11-41)
(c 30-33) [D-Tyr$^{12}$, CML$^{27}$, Glu$^{30}$, D-Gln$^{32}$, Lys$^{33}$]-AHC(12-41)
(c 30-33)[Ac-Thr$^{11}$, D-Phe$^{12}$, Nle$^{21,38}$, Glu$^{30}$, Ala$^{32}$, Lys$^{33}$]-r/hCRF(11-41)
(c 30-33) [D-Phe$^{12}$, Nle$^{21,38}$, Glu$^{30}$, D-Orn$^{32}$, Lys$^{33}$]-r/hCRF(11-41)
(c 30-33) [Ac-D-Phe$^{12}$, Nle$^{21,38}$, Glu$^{30}$, D-Dbu$^{32}$, Lys$^{33}$]-r/hCRF(12-41)
(c 30-33) [Ac-Ser$^{11}$, D-Phe$^{12}$, Nle$^{21,38}$, Glu$^{30}$, D-Lys$^{32}$, Lys$^{33}$]-r/hCRF(11-41)
(c 30-33) [Ac-Thr$^{11}$, D-Phe$^{12}$, Nle$^{21,38}$, Glu$^{30}$, D-Aph$^{32}$, Lys$^{33}$]-r/hCRF(11-41)
(c 30-33) [Ac-Ser$^{11}$, D-Phe$^{12}$, Nle$^{21,38}$, Glu$^{30}$, D-Dpr$^{32}$, Lys$^{33}$]-r/hCRF(11-41)
(c 30-33) [Ac-Thr$^{11}$, D-Phe$^{12}$, Nle$^{21,38}$, Glu$^{30}$, D-Aph(methyl)$^{32}$, Lys$^{33}$]-r/hCRF(11-41)

(c 30-33) [Ac-D-Phe$^{12}$, Nle$^{21,38}$, CML$^{27}$, Glu$^{30}$, D-Thr$^{32}$, Lys$^{33}$]-r/hCRF(12-41)

(bc 20-23, 30-33) [Ac-Thr$^{11}$, D-Phe$^{12}$, Nle$^{21,38}$, Lys$^{23,33}$, Glu$^{30}$, Gly$^{32}$]-r/hCRF(11-41)

These peptides are biopotent in inhibiting the secretion of ACTH and β-END-LI in response to various stimuli.

EXAMPLE XIII

The synthesis of Example I B is repeated to synthesize a very similar 33-residue CRF(9-41) peptide, substituting C$^\alpha$MeLeu for Leu$^{27}$, to produce the following peptide: (cyclo 30-33) [Ac-Asp$^9$, D-Phe$^{12}$, Nle$^{21,38}$, CML$^{27}$, Glu$^{30}$, Lys$^{33}$]-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. The measured value of 3947.87 obtained using liquid secondary ion mass spectrometry (LSIMS) is in agreement with the calculated value of 3947.23. The peptide's biopotency, determined by in vitro testing as previously described, is about 1.20 (0.41–4.21) times that of Peptide IV. In vivo testing shows that it is very significantly more effective than Peptide IV (Destressin) at 90, 120, 150 and 180 minutes at a dosage of about 100 μg/kg; it is considered to be long-acting.

EXAMPLE XIII A

The synthesis of Example XIII is repeated, substituting D-His for His$^{32}$, to produce the following peptide: (cyclo 30-33) [Ac-Asp$^9$, D-Phe$^2$, Nle$^{21,38}$, CML$^{27}$, Glu$^{30}$, D-His$^{32}$, Lys$^{33}$]-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

It has a purity of about 98% as a result of HPLC, which is confirmed by CZE. The measured value of 3947.2 obtained using LSIMS is in agreement with the calculated value of 3947.23. The peptide's biopotency, determined by in vitro testing as previously described, is about 2.22 (0.30–7.47) times that of Peptide IV. In vivo testing shows that it is very significantly more effective than Peptide IV at 90, 120 and 150 minutes at a dosage of about 100 μg/kg in adrenalectomized rats; it is considered to be fairly long-acting.

EXAMPLE XIII B

The synthesis of Example XIII A is generally repeated, substituting C$^\alpha$MeLeu for Val$^{18}$ and also shortening the N-terminus by 2 residues to produce the following peptide: (cyclo 30-33) [Ac-Thr$^{11}$, D-Phe$^{12}$, CML$^{18,27}$, Nle$^{21,38}$, Glu$^{30}$, D-His$^{32}$, Lys$^{33}$]-r/hCRF(11-41), having formula: (cyclo 30-33)Ac-Thr-D-Phe-His-Leu-Leu-Arg-Glu-CML-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

It has a purity of about 98% which is confirmed by CZE. The measured value of 3746.9 obtained using LSIMS is in agreement with the calculated value of 3747.15. The peptide's biopotency, determined by in vitro testing as previously described, is about 1.94 (0.97–4.12) times that of Peptide IV. In vivo testing shows that it is more effective than Peptide IV at 60, 90, 120 and 150 minutes at a dosage of about 100 μg/kg; it is considered to be long-acting.

EXAMPLE XIII C

The synthesis of Example XIII B is generally repeated, substituting C$^\alpha$MeLeu for Leu$^{15}$ instead of for Val$^{18}$, to produce the following peptide: (cyclo 30-33) [Ac-Thr$^{11}$, D-Phe$^{12}$, CML$^{15,27}$, Nle$^{21,38}$, Glu$^{30}$, D-His$^{32}$, Lys$^{33}$]-r/hCRF(11-41), having the formula: (cyclo 30-33)Ac-Thr-D-Phe-His-Leu-CML-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

It has a purity of about 98% which is confirmed by CZE. The measured value of 3733.1 obtained using LSIMS is in agreement with the calculated value of 3733.14. The peptide's biopotency, determined by in vitro testing as previously described, is about 1.11 times (0.62–2.02) that of Peptide IV. In vivo testing shows that it is about as effective as Peptide IV at 90, 120 and 150 minutes.

EXAMPLE XIII D

The synthesis of Example XIII is generally repeated, substituting C$^\alpha$MeLeu for Leu$^{14}$, to produce the following peptide: (cyclo 30-33) [Ac-Asp$^9$, D-Phe$^{12}$, CML$^{14,27}$, Nle$^{21,38}$, Glu$^{30}$, Lys$^{33}$]-r/hCRF(9-41), having the formula: (cyclo 30-33)Ac-Asp-Leu-Thr-D-Phe-His-CML-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. A measured value of 3961.28 is obtained using LSIMS and is in agreement with the calculated value of 3961.2. The peptide's biopotency, determined by in vivo testing as previously described, is greater than that of Peptide IV at 90 and 150 minutes. It remains significantly effective at 210 minutes, continues to show bioactivity at 270 minutes, and is considered to be very long-acting in vivo.

EXAMPLE XIII E

The synthesis of Example XIII is repeated, substituting C$^\alpha$MeLeu for Val$^{18}$, to produce the following peptide: (cyclo 30-33) [Ac-Asp$^9$, D-Phe$^{12}$, CML$^{18,27}$, Nle$^{21,38}$, Glu$^{30}$, Lys$^{33}$]-r/hCRF(9-41), having the formula: (cyclo 30-33)Ac-Asp-Leu-Thr-D-Phe-His-Leu-Leu-Arg-Glu-CML-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. The measured value of 3975.8 obtained using LSIMS is in agreement with the calculated value of 3975.3. The peptide's biopotency, determined by in vitro testing as previously described, is about 13 times that of the Standard. It is found to be very long-acting in vivo, being substantially better than Peptide IV at 120 minutes and remaining effective for longer than 180 minutes.

EXAMPLE XIII F

The synthesis of Example XIII B is repeated, substituting C$^{60}$ MeLeu for Nle$^{21}$ instead of for Val$^{18}$, to produce the following peptide: (cyclo 30-33) [Ac-Thr$^{11}$, D-Phe$^{12}$, CML$^{21,27}$, Glu$^{30}$, D-His$^{32}$, Lys$^{33}$, Nle$^{38}$]-r/hCRF(11-41), having the formula: (cyclo 30-33)Ac-Thr-D-Phe-His-Leu-Leu-Arg-Glu-Val-Leu-Glu-CML-Ala-Arg-Ala-Glu-Gln-CML-Ala-Gln-Glu-Ala-D-His-Lys-Asn-Arg-Lys-Leu-Nle-Glu-Ile-Ile-NH$_2$.

The measured value of 3961.0 obtained using LSIMS is in agreement with the calculated value of 3961.25. In vivo testing at a dosage of about 100 μg/kg shows that it is about as effective as Peptide IV at 90 minutes, but is short-acting as it loses its effectiveness at 135 minutes. It is considered to be equivalent to Peptide IX B.

EXAMPLE XIII G

The synthesis of Example XIII is repeated, substituting C$^\alpha$MeLeu for Lys$^{36}$, to produce the following peptide:

(cyclo 30-33) [Ac-Asp$^9$, D-Phe$^{12}$, Nle$^{21,38}$, CML$^{27,36}$, Glu$^{30}$, Lys$^{33}$-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-CML-Leu-Nle-Glu-Ile-Ile-NH$_2$.

It has a purity of about 98% which is confirmed by CZE. The measured value of 3946.26 obtained using LSIMS is in agreement with the calculated value of 3946.24. In vivo testing at a dosage of about 100 µg/kg shows that it is more effective than Peptide IV at 90 minutes, and retains substantial effectiveness at 135 minutes. It is considered to be of medium duration.

EXAMPLE XIII H

The synthesis of Example XIII is repeated, substituting C$^\alpha$MeLeu for Leu$^{37}$, to produce the following peptide: (cyclo 30-33) [Ac-Asp$^9$, D-Phe$^{12}$, Nle$^{21,38}$, CML$^{27,37}$, Glu$^{30}$, Lys$^{33}$-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-Ile-Ile-NH$_2$.

It has a purity of about 98% which is confirmed by CZE. A measured value of 3961.20 obtained using LSIMS is in agreement with the calculated value of 3961.2. In vivo testing at a dosage of about 100 µg/kg shows that it is substantially more effective than Peptide IV at 90, 15 120, 135, 180 and 210 minutes, and that it retain s significant effectiveness at 270 minutes. It is considered to be very long-acting.

EXAMPLE XIII I

The synthesis of Example XIII is repeated, substituting C$^\alpha$MeLeu for Nle$^{38}$, to produce the following peptide: (cyclo 30-33) [Ac-Asp$^9$, D-Phe$^{12}$, Nle$^{21}$, CML$^{27,37}$, Glu$^{30}$, Lys$^{33}$-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-CML-Glu-Ile-Ile-NH$_2$.

It has a purity of about 98% which is confirmed by CZE. A measured value of 3961.28 obtained using LSIMS is in agreement with the calculated value of 3961.2. The peptide's biopotency, determined by in vitro testing as previously described, is about 1.4 times the Standard, and it is considered effective to inhibit the secretion of ACTH in vivo.

EXAMPLE XIII J

The synthesis of Example XIII is repeated, substituting C$^\alpha$MeLeu for Ile$^{40}$, to produce the following peptide: (cyclo 30-33) [Ac-Asp$^9$, D-Phe$^{12}$, Nle$^{21,38}$, CML$^{27,40}$, Glu$^{30}$, Lys$^{33}$-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-CML-Ile-NH$_2$.

It has a purity of about 98% which is confirmed by CZE. A measured value of 3961.30 obtained using LSIMS is in agreement with the calculated value of 3961.2. In vivo testing by i.v. injection at a dosage of 100 µg/kg shows that it is substantially more effective than Peptide IV at 90 and 150 minutes. When administered i.v. at a dosage of 100 µg per rat (4 times the previous dosage), it exhibits such high effectiveness for 6 hours, while still exhibiting some effectiveness at 12 hours. It is considered to be very long-acting. The peptide is also formulated in corn oil and in an aqueous 3–6% mannitol solution and is injected s.c. At a dosage of about 30 µg in corn oil and an aqueous solution dosage of 100 µg, both formulations show significant inhibition of secretion of ACTH for over 24 hours.

EXAMPLE XIII K

The synthesis of Example XIII is repeated, substituting C$^{60}$ MeLeu for Ile$^{41}$, to produce the following peptide: (cyclo 30-33) [Ac-Asp$^9$, D-Phe$^{12}$, Nle$^{21,38}$, CML$^{27,41}$, Glu$^{30}$, Lys$^{33}$-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-CML-NH$_2$.

It has a purity of about 98% which is confirmed by CZE. A measured value of 3961.30 obtained using LSIMS is in agreement with the calculated value of 3961.2. In vivo testing at a dosage of about 100 µg/kg shows that it is more effective than Peptide IV at 90 and 120 minutes, but that it is no longer effective after 270 minutes.

EXAMPLE XIII L

The synthesis of Example XIII B is generally repeated, substituting C$^\alpha$MeLeu for Leu$^{19}$ instead of for Val$^{18}$, to produce the following peptide: (cyclo 30-33) [Ac-Thr$^{11}$, D-Phe$^{12}$, CML$^{19,27}$, Nle$^{21,38}$, Glu$^{30}$, D-His$^{32}$, Lys$^{33}$-r/hCRF (11-41), having the formula: (cyclo 30-33)Ac-Thr-D-Phe-His-Leu-Leu-Arg-Glu-Val-CML-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

It has a purity of about 98% which is confirmed by CZE. The measured value of 3733.2 obtained using LSIMS is in agreement with the calculated value of 3733.14. In vivo testing shows that it is about as effective as Peptide IV at 45 minutes and at 90 minutes. It is short-acting being no longer effective at 180 minutes at a dosage of about 100 µg/kg and is considered to be generally equivalent to Peptide IX B.

EXAMPLE XIII M

The synthesis of Example XIII is repeated, substituting C$^\alpha$MeLeu for Leu$^{10}$, to produce the following peptide: (cyclo 30-33) [Ac-Asp$^9$, CML$^{10,27}$, D-Phe$^{12}$, Nle$^{21,38}$, Glu$^{30}$, Lys$^{33}$]-r/hCRF(9-41), having the formula: (cyclo 30-33)Ac-Asp-CML-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. The measured value of 3961.3 Da obtained using LSIMS is in agreement with the calculated value of 3961.2 Da. It is found to be of medium duration in vivo, being substantially better than Peptide IV at 90 and 150 minutes, but remaining barely active at 210 minutes at a dosage of about 100 µg/kg.

EXAMPLE XIII N

The synthesis of Example XIII is repeated, substituting C$^\alpha$MeLeu for Leu$^{15}$, to produce the following peptide: (cyclo 30-33) [Ac-Asp$^9$, D-Phe$^{12}$, CML$^{15,27}$, Nle$^{21,38}$, Glu$^{30}$, Lys$^{33}$]-r/hCRF(9-41), having the formula: (cyclo 30-33)Ac-Asp-Leu-Thr-D-Phe-His-Leu-CML-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. The measured value of 3961.3 Da obtained using LSIMS is in agreement with the calculated value of 3961.2 Da. It is found to be short-acting in vivo, being somewhat better than Peptide IV at 90 minutes, but then losing effectiveness fairly rapidly so as to be only slightly effective at 150 minutes at a dosage of about 100 µg/kg.

EXAMPLE XIII P

The synthesis of Example XIII L is generally repeated, again substituting C$^\alpha$MeLeu for Leu$^{19}$ but using His$^{32}$ instead of D-His and extending the N-terminus by 2 residues to produce the following peptide: (cyclo 30-33) [Ac-Asp$^9$, D-Phe$^{12}$, CML$^{19,27}$, Nle$^{21,38}$, Glu$^{30}$, Lys$^{33}$]-r/hCRF(9-41), having the formula: (cyclo 30-33)Ac-Asp-Leu-Thr-D-Phe-His-Leu-Leu-Arg-Glu-Val-CML-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

It has a purity of about 98% which is confirmed by CZE. The measured value of 3961.3 Da obtained using LSIMS is in agreement with the calculated value of 3961.2 Da. In vivo testing shows that it is more effective than Peptide IV at 90 minutes. It still exhibits effectiveness at 150 minutes but not at 210 minutes at a dosage of about 100 µg/kg. It is considered to be generally equivalent to Peptide XIII.

EXAMPLE XIII Q

The synthesis of Example XIII is repeated, substituting C$^\alpha$MeLeu for Ala$^{24}$, to produce the following peptide: (cyclo 30-33) [Ac-Asp$^9$, D-Phe$^{12}$, Nle$^{21,38}$, CML$^{24,27}$, Glu$^{30}$, Lys$^{33}$]-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-CML-Glu-Gln-CML-Ala-Gln-Glu-Ala-His-Lys-Asn-Arg-Lys-Leu-Nle-Glu-Ile-Ile-NH$_2$.

It has a purity of about 98% which is confirmed by CZE. The measured value of 4003.3 Da obtained using LSIMS is in agreement with the calculated value of 4003.3 Da. It is found to have medium duration of in vivo activity, being substantially better than Peptide IV at 90 and 150 minutes, but losing effectiveness at about 210 minutes at a dosage of about 100 µg/kg.

EXAMPLE XIII R

The synthesis of Example XIII is generally repeated, substituting C$^\alpha$MeLeu for Leu$^{14}$, Leu$^{37}$ and Ile$^{40}$ to produce the following peptide: (cyclo 30-33) [Ac-Asp$^9$, D-Phe$^{12}$, CML$^{14,27,37,40}$, Nle$^{21,38}$, Glu$^{30}$, Lys$^{33}$]-r/hCRF(9-41), having the formula: (cyclo 30-33)Ac-Asp-Leu-Thr-D-Phe-His-CML-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-CML-Ile-NH$_2$.

It has a purity of about 98% which is confirmed by CZE. Using LSIMS, a measured value is obtained that is in agreement with the calculated value. The peptide is effective to inhibit the secretion of ACTH.

EXAMPLE XIII S

The synthesis of Example XIII R is repeated, substituting D-2Nal for D-Phe$^{12}$, to produce the following peptide: (cyclo 30-33) [Ac-Asp$^9$, D-2Nal$^{12}$, CML$^{14,27,37,40}$, Nle$^{21,38}$, Glu$^{30}$, Lys$^{33}$]-r/hCRF(9-41), having the formula: (cyclo 30-33)Ac-Asp-Leu-Thr-D-2Nal-His-CML-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-CML-Ile-NH$_2$.

It has a purity of about 98% which is confirmed by CZE. Using LSIMS, a measured value is obtained that is in agreement with the calculated value. The peptide is effective to inhibit the secretion of ACTH.

EXAMPLE XIII T

The synthesis of Example XIII is repeated, substituting C$^\alpha$MeLeu for Leu$^{37}$ and Ile$^{40}$, to produce the following peptide: (cyclo 30-33) [Ac-Asp$^9$, D-Phe$^{12}$, Nle$^{21,38}$, CML$^{27,37,40}$, Glu$^{30}$, Lys$^{33}$]-r/hCRF(9-41), having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-CML-Ile-NH$_2$.

It has a purity of about 98% which is confirmed by CZE. Using LSIMS, a measured value is obtained that is in agreement with the calculated value. The peptide is effective to inhibit the secretion of ACTH.

EXAMPLE XIII U

The synthesis of Example XIII is repeated, substituting C$^\alpha$MeLeu for Glu$^{17}$, to produce the following peptide: (cyclo 30-33) [Ac-Asp$^9$, D-Phe$^{12}$, CML$^{17,27}$, Nle$^{21,38}$, Glu$^{30}$, Lys$^{33}$]-r/hCRF(9-41), having the formula: (cyclo 30-33)Ac-Asp-Leu-Thr-D-Phe-His-Leu-Leu-Arg-CML-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$. It has a purity of about 98% which is confirmed by CZE. The synthesis is repeated substituting BOC-D-2Nal for BOC-D-Phe to produce the peptide (cyclo 30-33) [Ac-Asp$^9$, D-2Nal$^{12}$, CML$^{17,27}$, Nle$^{21,38}$, Glu$^{30}$, Lys$^{33}$]r/hCRF(9-41). HPLC show a purity of about 98% which is confirmed by CZE.

Both peptides have measured MS values in agreement with the calculated values and are effective in vivo to inhibit the secretion of ACTH.

EXAMPLE XIII V

The synthesis of Example XIII is repeated a number of times, each time also making at least one additional substitution of CML for a different residue. As a result, the following (cyclo 30-33) cyclic peptides are produced:

[Ac-Asp$^9$, D-Phe$^{12}$, CML$^{18,27}$, Nle$^{21,38}$, Glu$^{30}$, D-His$^{32}$, Lys$^{33}$]-r/hCRF(9-41)

[Ac-Asp$^9$, D-Phe$^{12}$, Nle$^{21,38}$, CML$^{27,36,40}$, Glu$^{30}$, Lys$^{33}$]-r/hCRF(9-41)

[Ac-Asp$^9$, D-Phe$^{12}$, Nle$^{21,38}$, CML$^{27,40}$, Glu$^{30}$, D-His$^{32}$, Lys$^{33}$]-r/hCRF(9-41)

[Ac-Asp$^9$, D-Phe$^{12}$, Nle$^{21,38}$, CML$^{27,36,37}$, Glu$^{30}$, Lys$^{33}$]-r/hCRF(9-41)

[Ac-Asp$^9$, D-Phe$^{12}$, Nle$^{21,38}$, CML$^{27,37,41}$, Glu$^{30}$, Lys$^{33}$]-r/hCRF(9-41)

[Ac-Asp$^9$, D-Phe$^{12}$, Nle$^{21,38}$, CML$^{27,37,41}$, Glu$^{30}$, D-His$^{32}$, Lys$^{33}$]-r/hCRF(9-41)

[Ac-Asp$^9$, D-Phe$^{12}$, Nle$^{21,38}$, CML$^{27,36,40}$, Glu$^{30}$, D-His$^{32}$, Lys$^{33}$]-r/hCRF(9-41)

[Ac-Asp$^9$, D-Phe$^{12}$, CML$^{14,27,40}$, Nle$^{21,38}$, Glu$^{30}$, Lys$^{33}$]-r/hCRF(9-41) Administration of these peptides stimulates the secretion of ACTH and β-END-LI, and iv injection lowers blood pressure.

EXAMPLE XIV

The synthesis of Example IV is repeated, substituting Glu for Gln$^{29}$ and Gln for Glu$^{30}$, to produce the following peptide: (cyclo 29-33) [D-Phe$^{12}$, Nle$^{21,38}$, Glu$^{29}$, D-His$^{32}$, Lys$^{33}$-r/hCRF(12-41), having the formula: (cyclo 29-33)H-D-Phe-His-Leu-Leu-Arg-Glu-Val-Leu-Glu-Nle-Ala-Arg-Ala-Glu-Gln-Leu-Ala-Glu-Gln-Ala-D-His-Lys-Asn-Arg-Lys-Leu-Nle-Glu-Ile-Ile-NH$_2$.

It has a purity of about 98% which is confirmed by CZE. The measured value of 3562.06 obtained using LSIMS is in agreement with the calculated value of 3562.05. The peptide's biopotency, determined by in vitro testing as previously described, is about 26.0 times (10.1–68.0) that of the Standard.

EXAMPLE XIV A

The synthesis of Example XIV is repeated, substituting His for D-His$^{32}$, to produce the following peptide: (cyclo 29-33) [D-Phe$^{12}$, Nle$^{21,38}$, Glu$^{29}$, Lys$^{33}$-r/hCRF(12-41), having the formula: (cyclo 29-33)H-D-Phe-His-Leu-Leu-Arg-Glu-Val-Leu-Glu-Nle-Ala-Arg-Ala-Glu-Gln-Leu-Ala-Glu-Gln-Ala-His-Lys-Asn-Arg-Lys-Leu-Nle-Glu-Ile-Ile-NH$_2$.

It has a purity of about 98% which is confirmed by CZE. The measured value of 3562.03 obtained using LSIMS is in agreement with the calculated value of 3562.05. The peptide's biopotency, determined by in vitro testing as previously described, is about 7.15 times (3.66–14.66) that of the Standard.

EXAMPLE XIV B

The synthesis of Example I is repeated, substituting Glu$^{28}$-Gln-Gln$^{30}$-Ala-Lys$^{32}$-Ser$^{33}$ for Ala$^{28}$-Gln-Glu$^{30}$-Ala-His$^{32}$-Lys$^{33}$, to produce the following peptide: (cyclo 28-32) [D-Phe$^{12}$, Nle$^{21,38}$, Glu$^{28}$, Lys$^{32}$]-r/hCRF(12-41), having the formula: (cyclo 28-32)H-D-Phe-His-Leu-Leu-Arg-Glu-Val-Leu-Glu-Nle-Ala-Arg-Ala-Glu-Gln-Leu-Glu-Gln-Gln-Ala-Lys-Ser-Asn-Arg-Lys-Leu-Nle-Glu-Ile-Ile-NH$_2$.

It has a purity of about 98% which is confirmed by CZE. The measured value of 3568.91 obtained using LSIMS is in agreement with the calculated value of 3569.04. The peptide's biopotency, determined by in vitro testing as previously described, is about 7.3 times (4.5–11.8) that of the Standard.

EXAMPLE XIV C

The synthesis of Example XV is repeated, substituting D-Gln for Gln$^{30}$, to produce the following peptide: (cyclo 28-32) [D-Phe$^{12}$, Nle$^{21,38}$, Glu$^{28}$, D-Gln$^{30}$, Lys$^{32}$]-r/hCRF (12-41), having the formula: (cyclo 28-32)H-D-Phe-His-Leu-Leu-Arg-Glu-Val-Leu-Glu-Nle-Ala-Arg-Ala-Glu-Gln-Leu-Glu-Gln-D-Gln-Ala-Lys-Ser-Asn-Arg-Lys-Leu-Nle-Glu-Ile-Ile-NH$_2$.

It has a purity of about 98% which is confirmed by CZE. The measured value obtained using laser desorption mass spectrometry (LDMS) is in agreement with the calculated value of 3569.04. The peptide's biopotency, determined by in vitro testing as previously described, is about 3.69 times (1.55–9.47) that of the Standard.

EXAMPLE XIV D

The synthesis of Example XV is repeated, substituting D-Ala for Ala$^{31}$, to produce the following peptide: (cyclo 28-32) [D-Phe$^{12}$, Nle$^{21,38}$, Glu$^{28}$, D-Ala$^{31}$, Lys$^{32}$]-r/hCRF (12-41), having the formula: (cyclo 28-32)H-D-Phe-His-Leu-Leu-Arg-Glu-Val-Leu-Glu-Nle-Ala-Arg-Ala-Glu-Gln-Leu-Glu-Gln-Gln-D-Ala-Lys-Ser-Asn-Arg-Lys-Leu-Nle-Glu-Ile-Ile-NH$_2$.

It has a purity of about 98% which is confirmed by CZE. The measured value obtained using LDMS is in agreement with the calculated value of 3569.04. The peptide's biopotency, determined by in vitro testing as previously described, is about 4.91 times (1.98–13.53) that of the Standard.

EXAMPLE XIV E

The synthesis of Example I is generally used to produce the following peptide: (cyclo 28-31) [D-Phe$^{12}$, Nle$^{21,38}$, Glu$^{28}$, Lys$^{31}$]-r/hCRF(12-41), having the formula: (cyclo 28-31)H-D-Phe-His-Leu-Leu-Arg-Glu-Val-Leu-Glu-Nle-Ala-Arg-Ala-Glu-Gln-Leu-Glu-Gln-Gln-Lys-His-Ser-Asn-Arg-Lys-Leu-Nle-Glu-Ile-Ile-NH$_2$.

It has a purity of about 98% which is confirmed by CZE. The measured value of 3635.30 obtained using LSIMS is in agreement with the calculated value of 3635.07. The peptide's biopotency, determined by in vitro testing as previously described, is about 3.12 times (1.12–10.07) that of the Standard.

EXAMPLE XIV F

The synthesis of Example I is generally used to produce the following peptide: (cyclo 29-32) [D-Phe$^{12}$, Nle$^{21,38}$, Glu$^{29}$, Lys$^{32}$-r/hCRF(12-41), having the formula: (cyclo 29-33)H-D-Phe-His-Leu-Leu-Arg-Glu-Val-Leu-Glu-Nle-Ala-Arg-Ala-Glu-Gln-Leu-Ala-Glu-Gln-Ala-Lys-Ser-Asn-Arg-Lys-Leu-Nle-Glu-Ile-Ile-NH$_2$.

It has a purity of about 98% which is confirmed by CZE. The measured value of 3512.26 obtained using LSIMS is in agreement with the calculated value of 3512.02. The peptide's biopotency, determined by in vitro testing as previously described, is about 3.38 times (1.15–12.10) that of the Standard.

EXAMPLE XV

The synthesis of Example XIII is repeated a number of times, each time also making one or more substitutions of Aib and/or CML for residues in that CRF antagonist peptide. As a result, the following (cyclo 30-33) cyclic peptides are produced:

[Ac-Asp$^9$, D-Phe$^{12}$, Nle$^{21,38}$, Aib$^{22}$, CML$^{27}$, Glu$^{30}$, Lys$^{33}$]-r/hCRF(9-41)

[Ac-Asp$^9$, D-Phe$^{12}$, Nle$^{21,38}$, Aib$^{24}$, CML$^{27}$, Glu$^{30}$, Lys$^{33}$]-r/hCRF(9-41)

[Ac-Asp$^9$, D-Phe$^{12}$, Nle$^{21,38}$, CML$^{27}$, Aib$^{28}$, Glu$^{30}$, Lys$^{33}$]-r/hCRF(9-41)

[Ac-Asp$^9$, D-Phe$^{12}$, Nle$^{21,38}$, CML$^{27}$, Aib$^{29}$, Glu$^{30}$, Lys$^{33}$]-r/hCRF(9-41)

[Ac-Asp$^9$, D-Phe$^{12}$, Nle$^{21,38}$, CML$^{27}$, Glu$^{30}$, Aib$^{31}$, Lys$^{33}$]-r/hCRF(9-41)

[Ac-Asp$^9$, D-Phe$^{12}$, Nle$^{21,38}$, CML$^{27}$, Glu$^{30}$, Lys$^{33}$, Aib$^{34}$]-r/hCRF(9-41)

[Ac-Asp$^9$, D-Phe$^{12}$, Nle$^{21,38}$, CML$^{27}$, Glu$^{30}$, Lys$^{33}$, Aib$^{39}$]-r/hCRF(9-41)

[Ac-Asp$^9$, D-Phe$^{12}$, Nle$^{21,38}$, CML$^{27}$, Glu$^{30}$, Lys$^{33}$, Aib$^{40}$]-r/hCRF(9-41)

[Ac-Asp$^9$, D-Phe$^{12}$, Nle$^{21,38}$, CML$^{27}$, Glu$^{30}$, Lys$^{33}$, Aib$^{41}$]-r/hCRF(9-41)

[Ac-Asp$^9$, D-Phe$^{12}$, Nle$^{21,38}$, CML$^{27,40}$, Glu$^{30}$, Lys$^{33}$, Aib$^{41}$]-r/hCRF(9-41)

[Ac-Asp$^9$, D-Phe$^{12}$, Nle$^{21,38}$, Aib$^{22}$, CML$^{27,40}$, Glu$^{30}$, Lys$^{33}$]-r/hCRF(9-41)

[Ac-Asp$^9$, D-Phe$^{12}$, Nle$^{21,38}$, Aib$^{24}$, CML$^{27,40}$, Glu$^{30}$, Lys$^{33}$]-r/hCRF(9-41)

[Ac-Asp$^9$, D-Phe$^{12}$, Nle$^{21,38}$, Aib$^{22,24}$, CML$^{27}$, Glu$^{30}$, Lys$^{33}$]-r/hCRF(9-41)

[Ac-Asp$^9$, D-Phe$^{12}$, Nle$^{21,38}$, CML$^{27,40}$, Aib$^{28}$, Glu$^{30}$, Lys$^{33}$]-r/hCRF(9-41)

[Ac-Asp$^9$, D-Phe$^{12}$, Nle$^{21,38}$, CML$^{27}$, Glu$^{30}$, Aib$^{31,41}$, Lys$^{33}$]-r/hCRF(9-41)

[Ac-Asp$^9$, D-Phe$^{12}$, CML$^{14,27}$, Nle$^{21,38}$, Glu$^{30}$, Aib$^{31}$, Lys$^{33}$]-r/hCRF(9-41)

[Ac-Asp$^9$, D-Phe$^{12}$, Nle$^{21,38}$, CML$^{27,37}$, Aib$^{28,31}$, Glu$^{30}$, Lys$^{33}$]-r/hCRF(9-41)

[Ac-Asp$^9$, D-Phe$^{12}$, CML$^{14,27}$, Nle$^{21,38}$, Aib$^{24,41}$, Glu$^{30}$, Lys$^{33}$]-r/hCRF(9-41)

Administration of these peptides stimulates the secretion of ACTH and β-END-LI, and iv injection lowers blood pressure.

EXAMPLE XVI

Using the procedure as generally set forth in Example I, the following CRF antagonist peptides are also prepared:

(c 30-33) [Ac-Asp$^9$, CML$^{17,27}$, Glu$^{30}$, Lys$^{33}$]-AHC(9-41)

(c 30-33) [Ac-Asp$^9$, CML$^{14,27}$, Lys$^{28,33}$, Glu$^{30}$]-oCRF(9-41)

(c 30-33) [Acr-Asp$^9$, Ser$^{11}$, D-Phe$^{12}$, CML$^{14,27}$, Nle$^{21,38}$, Glu$^{30}$, Lys$^{33}$]-r/hCRF(9-41)

(c 30-33) [Bz-Asp$^9$, D-2Nal$^{12}$, CML$^{14,27}$, Glu$^{30}$, Lys$^{33}$]-oCRF(9-41)

(c 30-33) [Pn-Asp$^9$, CML$^{17,27}$, Nle$^{18,21}$, Glu$^{30}$, Lys$^{33}$]-AHC(9-41)

(c 30-33) [Acr-Asp$^9$, D-Leu$^{12}$, CML$^{17,27}$, Glu$^{30}$, Lys$^{33}$]-r/hCRF(9-41)

(c 30-33) [Bt-Asp$^9$, D-Phe$^{12}$, CML$^{27,37}$, Nle$^{21}$, Glu$^{30}$, Lys$^{33}$]-oCRF(9-41)

(c 30-33) [Acr-Asp$^9$, D-4ClPhe$^{12}$, CML$^{15,27}$, Glu$^{30}$, Lys$^{33}$]-AHC(9-41)

(c 30-33) [Nph-Asp$^9$, D-Phe$^{12}$, CML$^{15,27}$, Nle$^{21,38}$, Arg$^{28}$, Glu$^{30}$, Lys$^{33}$]-r/hCRF(9-41)

(c 30-33) [Bz-Asp$^9$, D-Phe$^{12}$, CML$^{14,27}$, Nle$^{21,38}$, Glu$^{30}$, D-Trp$^{32}$, Lys$^{33}$]-r/hCRF(9-41)

(c 30-33) [Vac-Asp$^9$, D-Phe$^{12}$, CML$^{27,37}$, Nle$^{21,38}$, Glu$^{30}$, Lys$^{33}$]-r/hCRF(9-41)

(c 30-33) [iPn-Asp$^9$, Nle$^{18,21}$, CML$^{27,37}$, Glu$^{30}$, D-His$^{32}$, Lys$^{33}$]-AHC(9-41)

(c 30-33) [Nph-Asp$^9$, D-Phe$^{12}$, CML$^{27,37}$, Glu$^{30}$, D-Trp$^{32}$, Lys$^{33}$, Aib$^{28}$]-r/hCRF(9-41)

(c 30-33) [Bz-Asp$^9$, CML$^{27,37}$, Nle$^{21,38}$, Glu$^{30}$, Lys$^{33}$]-r/hCRF(9-41)

(c 30-33) [For-Asp$^9$, D-Phe$^{12}$, CML$^{14,27}$, Glu$^{30}$, Lys$^{33}$]-r/hCRF(9-41)

(c 30-33) [For-Asp$^9$, D-Pal$^{12}$, Nle$^{21}$, CML$^{27,38}$, Glu$^{30}$, Lys$^{33}$]-oCRF(9-41)

(c 30-33) [Bt-Asp$^9$, D-Tyr-Asp$^9$, D-Phe$^{12}$, CML$^{27}$, Glu$^{30}$, Lys$^{33}$]-AHC(9-41)

(c 30-33) [Vl-Asp$^9$, D-Phe$^{12}$, CML$^{14,27}$, Nle$^{21,38}$, Lys$^{28,33}$, Glu$^{30}$]-r/hCRF(9-41)

(c 30-33) [Flu-Asp$^9$, Ser$^{11}$, D-Phe$^{12}$, Nle$^{21,38}$, CML$^{27,40}$, Glu$^{30}$, Lys$^{33}$]-r/hCRF(9-41)

(c 30-33) [Ac-Asp$^9$, D-Phe$^{12}$, Nle$^{21,38}$, Lys$^{23}$, CML$^{27,41}$, Glu$^{30}$, Lys$^{33}$]-r/hCRF(9-41)

(c 30-33) [Ac-Asp$^9$, D-2Nal$^{12}$, CML$^{14,27}$, Glu$^{30}$, D-2Nal$^{32}$, Lys$^{33}$]-oCRF(9-41)

(c 30-33) [Acr-Asp$^9$, CML$^{17,27}$, Nle$^{18,21}$, Glu$^{30}$, D-Arg$^{32}$, Lys$^{33}$]-AHC(9-41)

(c 30-33) [Bz-Asp$^9$, D-Phe$^{12}$, CML$^{27}$, Glu$^{30}$, D-Leu$^{32}$, Lys$^{33}$]-r/hCRF(9-41)

(c 30-33) [Ac-Asp$^9$, D-Phe$^{12}$, CML$^{27,37}$, Nle$^{21}$, Glu$^{30}$, Tyr$^{32}$, Lys$^{33}$]-oCRF(9-41)

(c 30-33) [Nph-Asp$^9$, D-4Cpa$^{12}$, CML$^{27}$, Glu$^{30}$, Arg$^{32}$, Lys$^{33}$]-AHC(9-41)

These peptides are biopotent in inhibiting the secretion of ACTH and β-END-LI in response to various stimuli.

Preferably the cyclic CRF antagonist does not inherently activate the CRF receptor. For example, Peptide I of Example I has only about 3% or less intrinsic CRF activity when administered at the highest dosage. Generally a peptide is considered not to significantly activate the CRF receptor when its intrinsic activity measures about 20% or less of the native compound. Preferred antagonists have an intrinsic activity of about 15% or less; however, intrinsic activity is simply one factor to be balanced against a peptide's potency as an antagonist.

CRF profoundly stimulates the pituitary-adrenalcortical axis, and CRF antagonists are useful to inhibit the functions of this axis in certain types of patients experiencing high ACTH and endogenous glucocorticoid production. For example, CRF antagonists may be useful in regulating pituitary-adrenal function in patients having pituitary Cushings disease or any CRF-sensitive tumor. Preferred members of the improved CRF antagonists provided by the invention bind with high affinity to CRF receptors without significantly activating the receptors, i.e. they exhibit an intrinsic activity or agonism less than 15% of that of ovine CRF. Moreover, they are considered to have a neuronal effect when administered peripherally, e.g. i.v., s.c., intranasally, intrapulmonarily, etc., and may be used to combat stress-induced stomach disorders which result from acid secretion.

Most other regulatory peptides have been found to have effects upon the endocrine system, the central nervous system and upon the gastrointestinal tract. Because ACTH and β-END-LI secretion is the "sine qua non" of mammal's response to stress, it is not surprising that CRF has significant effects on the brain as a mediator of many of the body's stress responses. Accordingly, CRF antagonists delivered to the brain should also find application in modifying the mood, learning and behavior, e.g. drug addition and drug and alcohol withdrawal, of normal and mentally disordered individuals. Furthermore, CRF antagonists in the brain should ameliorate stress-induced conditions to which endogenous CRF might contribute, including some types of hypertension, anorexia nervosa, hemorrhagic stress, infertility, decreased libido, impotency and hyperglycemia. Because peripherally administered CRF antagonists reduce the levels of ACTH, β-END, β-lipotropin, other pro-opiomelanocortin gene products and corticosterone, administration of the antagonists may be used to reduce the effects of all of these substances on the brain to thereby influence memory, mood, pain appreciation, etc., and more specifically, alertness, depression and/or anxiety, as well as to modulate the immune system, gastrointestinal tract and adrenalcortical growth and function. They may also be used to treat HIV infections and Alzheimer's disease.

Because CRF antagonists will block the hypothalamic pituitary axis (HPA) and therefore block ACTH and corticosterone secretion in instances when the desired effects of administration may be on other functions (e.g. immune, neuronal, etc.), hormonal replacement therapy (i.e. administration of ACTH and/or corticosterone) may be advisable as an adjunct to CRF antagonist therapy, as necessary to maintain homeostasis. As a parallel example, testosterone replacement is often used when treating normal humans with GnRH antagonists for male contraception in order to retain libido. Such hormonal replacement is not indicated in the case of treatment of prostate cancer.

All CRF-related peptides have been shown to dilate the mesenteric vascular bed. CRF antagonists should also be of use for decreasing blood flow to the gastrointestinal tract of mammals, particularly humans. Also, because CRF influences gastric acid production, CRF antagonists should also be effective to modulate gastrointestinal functions, including abdominal bowel syndrome and inflammatory diseases.

CRF antagonists or the nontoxic addition salts thereof, combined with a pharmaceutically acceptable carrier to form a pharmaceutical composition, may be administered to mammals, including humans, either intravenously, subcutaneously, intramuscularly, intrapulmonarily, percutaneously, e.g. intranasally, intracerebroventricularly or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to inhibit endogenous glucocorticoid production or for possible uses outlined above. Administration may be in a variety of dosage forms such as tablets, lozenges, powders, syrups, injectable solutions, injectable depot formulations and the like. The required dosage will vary with the particular condition being treated, with the severity of the condition and with the duration of desired treatment, and multiple dosages may be used for a single day. In order to block the stress-related effects of endogenous CRF within the central nervous system, it may be necessary to deliver the CRF antagonists into the cerebral ventricle or spinal fluid. Alternatively, a means of modifying the antagonists so that they could penetrate the blood-brain barrier should be found. For parental administration, solutions in peanut oil, in aqueous propylene glycol, or in sterile aqueous solution may be employed; sterile aqueous media are readily available. Such aqueous solutions, which are suitably buffered, are especially suitable for intravenous (i.v.), intramuscular, subcutaneous (s.c.) and intraperitoneal administration. For s.c. administration, corn oil or a 3–6% mannitol solution may be preferred.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, hydriodide, cinnamate, sulphate, sulfamate, sulfonate, phosphate, tannate, oxalate, fumarate, gluconate, alginate, maleate, acetate, trifluoroacetate, citrate, benzoate, succinate, pamoate, malate, ascorbate, tartrate and the like which can be prepared in a conventional manner. The salts of trifluoroacetic acid and pamoic acid may be preferred. If the active ingredient is to be administered in tablet form, the tablet may contain a binder or excipient, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver the CRF antagonist peptide over prolonged periods of time, for example, for periods of one week or considerably longer, from a single administration, and slow release, depot or implant dosage forms may be utilized. For example, a suitable, slow-release depot formulation for injection may contain the CRF antagonist or a salt thereof dispersed or encapsulated in a slow degrading, non-toxic or non-antigenic polymer such as a polylactic acid/polyglycolic acid polymer, for example, as described in U.S. Pat. No. 3,773,919.

The peptides should be administered under the guidance of a physician in single or multiple doses, and pharmaceutical compositions will usually contain the peptide in conjunction with a known, pharmaceutically-acceptable carrier that may extend its duration of action. The effective dosage generally depends on the intended route of administration and other factors such as age and weight of the patient, as generally known to a physician, and also upon the illness being treated. Usually, the dosage will be from about 0.01 to about 10 milligrams of the peptide per kilogram of the body weight of the host animal. For the treatment of inflammatory diseases about 0.1 to about 100 mg/kg is generally employed; for gastrointestinal diseases about 0.1 to about 50 mg/kg, as well as for anorexia nervosa, hemorrhagic stress, treatment of drug and alcohol withdrawal symptoms and treatment of fertility problems. The daily dosage may be given in a single dose or up to three divided doses.

As mentioned hereinbefore, CRF receptors have now been cloned and are disclosed in the aforementioned Chen et al. article, in Perrin, M., et al., P.N.A.S. 92, 2969–2973 (March 1995), and in Lovenberg, T., et al., P.N.A.S., 92, 836–840 (January 1995). Binding affinity is a term used to refer to the strength of interaction between ligand and receptor. To demonstrate binding affinity for a CRF receptor, the peptides of the invention are easily evaluated using a tracer ligand of known affinity, such as $^{125}$I-radiolabelled oCRF or [D-Tyr$^{12}$, Nle$^{21,38}$]-r/hCRF(12-41), in binding assay experiments which are well known in this art. The results of such assays indicate the affinity at which each ligand binds to a CRF receptor, expressed in terms of $K_i$, an inhibitory binding affinity constant relative to such a known standard. $K_i$ (inhibitory binding affinity constant) is determined using a "standard" or "tracer" radioactive ligand and thus measures the displacement of the tracer from the receptor or binding protein; it is most properly expressed with reference to such tracer. However, so long as these assays are carefully performed under specific conditions with relatively low concentrations of receptor or the like, the calculated $K_i$ will be substantially the same as its dissociation constant $K_D$. Dissociation constant $K_D$ is representative of the concentration of ligand necessary to occupy one-half (50%) of the binding sites of a receptor or the like. It is particularly efficient to test for $K_i$ because only a single tracer need be labelled, e.g. radioiodinated. A given ligand having a high binding affinity for a CRF receptor will require the presence of very little ligand to bind at least 50% of the available binding sites so that the $K_D$ value for that ligand and receptor will be a small number. On the other hand, a given ligand having a low binding affinity for a particular CRF receptor will require the presence of a relatively high level of the ligand to bind 50% of the sites, so that the $K_D$ value for that ligand and receptor will be a large number.

With respect to a particular receptor protein, a CRF analog peptide having a $K_D$ of about 10 nM or less means that a concentration of the ligand (i.e., the CRF analog peptide) of no greater than about 10 nM will be required to occupy at least 50% of the active binding sites of the receptor protein. Such values may be fairly determined from the results obtained using a radioiodinated standard and no more than approximately 0.8 nM of the receptor (approximately 10–20 pmol receptor/mg membrane protein). Preferred peptides provided by this invention have a binding affinity ($K_D$) such that a ligand concentration of about 10 nanomolar or less is required in order to occupy (or bind to) at least 50% of the receptor binding sites, and these are considered to have high affinity. Some of these CRF analog peptides have a binding affinity of about 2 nM or less. Generally, for purposes of this application, a dissociation constant of about 5 nanomolar or lower is considered to be an indication of strong affinity, and a $K_D$ of about 2 nanomolar or less is an indication of very strong affinity. For example, the cyclic peptide of Example I C binds CRF-RA with very strong affinity, having a $K_D$=about 2.0 nanomolar. It is also considered to be particularly advantageous that some of the CRF analog peptides have a substantially higher affinity for one of the two families of CRF-RA and CRF-RB receptors so that they are thus selective in their biological effect.

These binding assays employing CRF receptors are straightforward to perform and can be readily carried out with initially identified or synthesized peptides to determine whether such peptides will likely be effective CRF antagonists. Generally, effective CRF antagonist peptides will exhibit not more than about 25% intrinsic activity in in vitro testing, and usually not more than about 5%, e.g. will not stimulate the secretion of ACTH at a level more than about 25% of a similar molar concentration of ovine CRF(1-41). However, such a criterion is not considered critical, as experience has shown that such intrinsic agonist activity very often does not translate into in vivo effects and thus may be acceptable. Such binding assays can be carried out in a variety of ways as well known to one of skill in the art. A detailed example of such an assay is set forth in the Perrin, M., et al., *Endocrinology* article. Competitive binding assays employing the peptide of Example I C or IV A are particularly contemplated to evaluate whether candidate peptides and nonpeptides have high affinity for each of the various CRF receptors, e.g. CRF-RA, CRF-RB$_L$ and CRF-RB$_S$ as a first step in determining whether a candidate is an effective antagonist. In such assays, an appropriate cyclic CRF antagonist is appropriately labeled with a substance that is readily detected, such as a radioactive isotope, e.g. $^{125}$I, or an enzyme or some other suitable tag, such as one that fluoresces.

The use of competitive binding assays is considered particularly valuable for screening candidates for new drugs. e.g. to identify new CRF-like peptides or other compounds having even greater or more selective binding affinity for CRF receptors, which candidates would therefore be potentially useful as drugs. In the assay, one determines the ability of the candidate antagonist to displace the labelled peptide. Such screening assays as described hereinbefore may be used with a radiolabelled cyclic CRF antagonist, e.g., (cyclo 30-33) [I$^{125}$-D-Tyr$^{12}$, Nle$^{21,38}$, Glu$^{30}$, D-His$^{32}$, Lys$^{33}$]r/hCRF(12-41) to screen for potential CRF agonists. Assays employing a labelled CRF antagonist with high affinity may be used to screen for more potent antagonists of CRF. They may also be labelled with an enzyme or some other suitable tag.

As used herein all temperatures are °C. and all ratios are by volume. Percentages of liquid materials are also by volume. By lower alkyl is meant $C_1$ to $C_6$.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. For example, pharmaceutically acceptable salts and other comparable formulations, although not specifically recited, are clearly equivalents of the claimed subject matter. Moreover, substitutions and modifications at other positions throughout the CRF peptide chain as indicated in the first general formula in the detailed description may be made without detracting from the potency of the antagonists. Developments in the field have shown that peptides having the various specified residues at positions 13-15, 17-19, 24-29, 34, 36, 37 and 39-41 in the molecule exhibit CRF activity. As a result, it is well-accepted in this art that an r/hCRF antagonist having a particular amino acid sequence which exhibits improved biopotency as a result of substitutions elsewhere in the sequence (such as a cyclic peptide having the 30-33 lactam bond described herein) will retain its improved biopotency even if a number of specified substitutions are incorporated in other locations in the molecule. Instead of D-Phe at the 12-position, L-Phe or Tyr or another appropriate D-isomer generally similar to those hereinbefore mentioned, e.g., D-Cpa, may be present and is considered to be equivalent, although a D-isomer is preferred. The N-terminus of CRF (10-41), CRF(11-41) or CRF(12-41) analogs can be extended by Tyr or D-Tyr and is preferably acylated by an acyl group having 15 or less carbon atoms, preferably by one having 7 or less, e.g. acetyl. When D-Tyr is included, for purposes of radioiodination, for example at the N-terminus, instead of His$^{32}$ or D-His$^{32}$ or Lys$^{36}$ it may be preferable to substitute Asn$^{32}$ or D-Asn$^{32}$ or D-Ala$^{32}$ or Arg$^{36}$ which are considered equivalents.

D-Ala$^{31}$ can be substituted for Ala$^{31}$ with retention of biopotency well above that of the native sequence, thus, it is considered an equivalent at the 31-position. Instead of the simple amide at the C-terminus, a lower alkyl-substituted amide, i.e., 1–4 carbon atoms, e.g., methylamide or ethylamide, may be incorporated. As an alternative to a disulfide cyclizing bond, a carba or dicarba bond can be used (see U.S. Pat. No. 4,115,554) which is considered an equivalent bond. An equivalent lactam bond can also be created by linking the sidechains of Lys$^{30}$ and Glu$^{33}$; however, the bonds illustrated hereinbefore are preferred. The amino group which is reacted to form the 30-33 lactam cyclizing bond or the α-amino group of one of the residues in positions 30 through 33 may be alkylated, as by adding a methyl group; such changes are considered to create equivalent cyclic peptides. Likewise when a D- or L-isomer of Aph, Lys, Orn, Dbu, Dpr, Arg, or Agl is present in the 32-position, its side chain amino group which forms the lactam bond may also be optionally alkylated by a lower alkyl group, e.g., methyl or ethyl. All such aforementioned peptides are considered as being within the scope of the invention.

Various features of the invention are emphasized in the claims which follow.

What is claimed is:

1. A cyclic CRF antagonist peptide which binds to CRF receptors but has an intrinsic activity with respect to such receptors equal to 20% or less than that of native CRF, which peptide has the formula Y-A-D-Xaa-B-$Xaa_c$-$Xaa_a$-$Xaa_b$-$Xaa_c$-C-$NH_2$ wherein: Y is an acyl group having up to 15 carbon atoms; A is des-A, Thr, Ser, Leu-Thr, Leu-Ser, Asp-Leu-Thr or Asp-Leu-Ser; D-Xaa is D-Phe, D-2Nal or D-Leu; B is a sequence of 17 amino acid residues of a peptide of the CRF family selected from the group of sequences consisting of residues 13-29 of mammalian and fish CRFs or fish urotensins or residues 12-28 of sauvagine; $Xaa_c$ represent a pair of amino acid residues, the side chains of which are linked in a cyclizing bond; $Xaa_a$ is a natural α-amino acid residue other than Cys; $Xaa_b$ is a residue of either (a) a D-isomer amino acid from the group consisting of D-isomers of natural α-amino acids other than Cys and unnatural aromatic α-amino acids, or (b) a natural L-isomer α-amino acid other than Cys; and C is a sequence of the last 8 amino acid residues of the C-terminal portion of a peptide of the CRF family selected from the group of sequences consisting of residues 13-29 of mammalian and fish CRFs or fish urotensins or residues 12-28 of sauvagine and wherein Nle may be substituted for Met in said peptide sequences provided that CML may be present as residue-27, or as residue-26 in the sauvagine sequence.

2. A cyclic peptide which is an antagonist of CRF, said peptide having the formula: (cyclo 30-33)Y-$R_9$-$R_{10}$-$R_{11}$-D-Phe-$R_{13}$-$R_{14}$-$R_{15}$-Arg-$R_{17}$-$R_{18}$-$R_{19}$-$R_{20}$-$R_{21}$-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$-$R_{38}$-$R_{39}$-$R_{40}$-$R_{41}$-$NH_2$ wherein Y is an acyl group having up to 15 carbon atoms; $R_9$ is Asp, Tyr or D-Tyr; $R_{10}$ is Leu or CML; $R_{11}$ is Thr or Ser; $R_{13}$ is His, Tyr or Glu; $R_{14}$ is CML or Leu; $R_{15}$ is Leu or CML; $R_{17}$ is Glu, CML, Asn or Lys; $R_{18}$ is Val, Nle, CML or Met; $R_{19}$ is Leu or Ile; $R_{20}$ is Glu, D-Glu, Cys or His; $R_{21}$ is Nle or Met; $R_{22}$ is Ala, D-Ala, Aib, Asp, Thr, D-Thr, Glu or D-Glu; $R_{23}$ is Arg, Cys, Orn or Lys; $R_{24}$ is Ala, Aib or CML; $R_{25}$ is Glu or Asp; $R_{26}$ is Gln, Asn or Lys; $R_{27}$ is Leu or CML; $R_{28}$ is Ala, Lys, Aib or Arg; $R_{29}$ is Gln, Aib or Glu; $R_{30}$ is Glu; $R_{31}$ is Aib or an L-isomer of an α-amino acid other than Cys; $R_{32}$ is Aib or a D- or L-isomer of an α-amino acid other than Cys; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{38}$ is Nle, Met or CML; $R_{39}$ is Glu, Aib or Asp; $R_{40}$ is CML, Ile, Aib, Thr, Asn, Glu, Ala, Val, Leu, Nle, Phe, Nva, Gly or Gln; and $R_{41}$ is Ala, Aib, Ile, Gly, Val, Leu, CML, Nle, Phe, Nva or Gln; wherein D-Phe$^{12}$ may be substituted by another D-amino acid, such as D-Leu, D-Tyr, D-Trp, D-Cpa, D-Trp, D-Nal or D-Pal, or by Phe or Tyr; provided that the N-terminus may be shortened by the elimination of $R_9$ or $R_9$–$R_{10}$ or $R_9$–$R_{10}$–$R_{11}$; and provided further that a second cyclizing bond may exist between $R_{20}$ and $R_{23}$.

3. A cyclic CRF antagonist peptide according to claim 2 having the formula: (cyclo 30-33)Y-Asp-Leu-Thr-$R_{12}$-$R_{13}$-$R_{14}$-$R_{15}$-Arg-$R_{17}$-$R_{18}$-Leu-$R_{20}$-Nle-$R_{22}$-$R_{23}$-$R_{24}$-$R_{25}$-$R_{26}$-$R_{27}$-$R_{28}$-$R_{29}$-$R_{30}$-$R_{31}$-$R_{32}$-$R_{33}$-$R_{34}$-Arg-$R_{36}$-$R_{37}$-Nle-$R_{39}$-$R_{40}$-$R_{41}$-NH$_2$ wherein Y is an acyl group having not more than 7 carbon atoms; $R_{12}$ is D-Phe, D-Leu, D-2Nal or D-Tyr; $R_{13}$ is His, Tyr or Glu; $R_{14}$ is Leu or CML; $R_{15}$ is Leu or CML; $R_{17}$ is Glu or CML; $R_{18}$ is Val, CML, Nle or Met; $R_{20}$ is Glu or D-Glu; $R_{22}$ is Ala, D-Ala, Aib, Thr, Asp or Glu; $R_{23}$ is Arg or Lys; $R_{24}$ is Ala, Aib or CML; $R_{25}$ is Asp or Glu; $R_{26}$ is Gln, Asn or Lys; $R_{27}$ is Leu or CML; $R_{28}$ is Ala or Aib; $R_{29}$ is Gln, Aib or Glu; $R_{30}$ is Glu; $R_{31}$ is Ala or Aib; $R_{32}$ is His, D-His, Aib, D-Arg, D-2Nal, D-3Pal, D-Trp, imBzlD-His, Gly, Tyr, D-Tyr, Leu, D-Leu, Ala or D-Ala; $R_{33}$ is Lys or Orn; $R_{34}$ is Asn or Aib; $R_{36}$ is Lys, Orn, Arg, Har, CML or Leu; $R_{37}$ is CML, Leu or Tyr; $R_{39}$ is Glu, Aib or Asp; $R_{40}$ is Ile, CML, Aib, Thr, Glu, Asn or Gln; and $R_{41}$ is Ala, Aib, Ile, CML, Val or Phe.

4. A cyclic CRF antagonist peptide according to claim 2 having the formula: (cyclo 30-33)Y-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-CML-Ile-NH$_2$, wherein Y is an acyl group having not more than 12 carbon atoms.

5. A cyclic CRF antagonist peptide according to claim 3 having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-Ile-Ile-NH$_2$; (cyclo 30-33)Ac-Asp-Leu-Thr-D-Phe-His-CML-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$; (cyclo 30-33)Ac-Asp-Leu-Thr-D-Phe-His-Leu-Leu-Arg-Glu-Leu-CML-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$; or (cyclo 30-33)Ac-Asp-Leu-Thr-D-Phe-His-Leu-Leu-Arg-Glu-CML-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$.

6. A cyclic CRF antagonist peptide according to claim 3 having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-His-Lys-Asn-Arg-Lys-CML-Nle-Glu-Ile-Ile-NH$_2$; or (cyclo 30-33)Ac-Asp-Leu-Thr-D-Phe-His-CML-Leu-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$.

7. A cyclic CRF antagonist peptide according to claim 2 wherein $R_{32}$ is His, D-His, D-Arg, D-Nal, imBzlD-His, D-Tyr, D-Asn, D-Cpa, D-Phe, D-Pal, D-Lys, D-Dpr, D-Aph, D-Dbu, D-Dpr(Nic), D-Agl(Nic) or D-Orn(Nic).

8. A cyclic CRF antagonist peptide according to claim 2 having the formula: (cyclo 30-33)Ac-Leu-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$; or (cyclo 30-33)Ac-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-Leu-Nle-Glu-Ile-Ile-NH$_2$; or (cyclo 30-33)Ac-Leu-Thr-D-Phe-His-Leu-Leu-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$; or (cyclo 30-33)Ac-Leu-Thr-D-Phe-His-Leu-Leu-Arg-Glu-CML-Leu-Glu-Nle-Ala-Arg-Ala-Glu-Gln-CML-Ala-Gln-Glu-Ala-D-His-Lys-Asn-Arg-Lys-Leu-Nle-Glu-Ile-Ile-NH$_2$; or (cyclo 30-33)Ac-Asp-Leu-Thr-D-Phe-His-Leu-Leu-Arg-Glu-Val-Leu-Glu-Nle-Ala-Arg-CML-Glu-Gln-CML-Ala-Gln-Glu-Ala-His-Lys-Asn-Arg-Lys-Leu-Nle-Glu-Ile-Ile-NH$_2$; or (cyclo 30-33)Ac-Thr-D-Phe-His-Leu-Leu-Arg-Glu-Val-Leu-Glu-Nle-Ala-Arg-Ala-Glu-Gln-CML-Ala-Gln-Glu-Ala-His-Lys-Asn-Arg-Lys-CML-Nle-Glu-Ile-Ile-NH$_2$.

9. A cyclic CRF antagonist peptide according to claim 2 having the formula: (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-Ala-Lys-Asn-Arg-Lys-Leu-Nle-Glu-Ile-Ile-NH$_2$ or (cyclo 30-33)Ac-Asp-Leu-Thr-D-Phe-His-Leu-Leu-Arg-Glu-Val-Leu-Glu-Nle-D-Ala-Arg-Ala-Glu-Gln-CML-Ala-Gln-Glu-Ala-D-2Nal-Lys-Asn-Arg-Lys-Leu-Nle-Glu-Ile-Ile-NH$_2$.

10. A cyclic CRF antagonist peptide according to claim 2 having the formula: (cyclo 30-33)Ac-Asp-Leu-Thr-D-Phe-His-CML-Leu-Arg-Glu-Val-Leu-Glu-Nle-Ala-Arg-Ala-Glu-Gln-CML-Ala-Gln-Glu-Ala-imBzlD-His-Lys-Asn-Arg-Lys-Leu-Nle-Glu-Ile-Ile-NH$_2$ or (cyclo 30-33)Ac-Asp-Leu-Thr-D-Phe-His-Leu-Leu-Arg-Glu-Val-Leu-Glu-Nle-Ala-Arg-Ala-Glu-Gln-CML-Ala-Gln-Glu-Ala-D-His-Lys-Asn-Arg-Lys-Leu-Nle-Glu-CML-Ile-NH$_2$.

11. A cyclic CRF antagonist peptide according to claim 2 having the formula: (cyclo 30-33)Y-Asp-Leu-Thr-$R_{12}$-His-$R_{14}$-Leu-Arg-Glu-$R_{18}$-$R_{19}$-$R_{20}$-$R_{21}$-$R_{22}$-$R_{23}$-$R_{24}$-$R_{25}$-Gln-$R_{27}$-$R_{28}$-Gln-$R_{30}$-$R_{31}$-$R_{32}$-$R_{33}$-$R_{34}$-Arg-$R_{36}$-$R_{37}$-Nle-$R_{39}$-$R_{40}$-$R_{41}$-NH$_2$ wherein Y is an acyl group having not more than 7 carbon atoms; $R_{12}$ is D-Phe or D-2Nal; $R_{14}$ is Leu or CML; $R_{18}$ is Val, CML or Nle; $R_{19}$ is Leu or Ile; $R_{20}$ is Glu or D-Glu; $R_{21}$ is Nle or Met; $R_{22}$ is Ala, D-Ala, Aib or Thr; $R_{23}$ is Arg or Lys; $R_{24}$ is Ala or Aib; $R_{25}$ is Asp or Glu; $R_{27}$ is Leu or CML; $R_{28}$ is Ala or Aib; $R_{30}$ is Glu; $R_{31}$ is Ala or Aib; $R_{32}$ is D-His, imBzlD-His, D-Arg, D-2Nal, or a D-isomer of another basic and/or aromatic α-amino acid; $R_{33}$ is Lys or Orn; $R_{34}$ is Aib or Asn; $R_{36}$ is Lys or CML; $R_{37}$ is Leu or CML; $R_{39}$ is Glu or Asp; $R_{40}$ is Ile, CML or Aib; and $R_{41}$ is Ala, Aib, CML or Ile.

12. A cyclic CRF antagonist peptide according to claim 2 having the formula: (cyclo 30-33)Y-Asp-Leu-Thr-D-Phe-His-$R_{14}$-Leu-Arg-Glu-$R_{18}$-Leu-$R_{20}$-Nle-$R_{22}$-$R_{23}$-$R_{24}$-$R_{25}$-Gln-$R_{27}$-$R_{28}$-$R_{29}$-$R_{30}$-$R_{31}$-$R_{32}$-$R_{33}$-$R_{34}$-Arg-$R_{36}$-$R_{37}$-Nle-$R_{39}$-$R_{40}$-$R_{41}$-NH$_2$ wherein Y is Ac, Acr or For; $R_{14}$ is Leu or CML; $R_{18}$ is Val, CML or Nle; $R_{20}$ is Glu or D-Glu; $R_{22}$ is Ala, Aib, D-Ala or Thr; $R_{23}$ is Arg or Lys; $R_{24}$ is Ala or Aib; $R_{25}$ is Asp or Glu; $R_{27}$ is Leu or CML; $R_{28}$ is Ala or Aib; $R_{29}$ is Gln or Glu; $R_{30}$ is Glu; $R_{31}$ is Ala or Aib; $R_{32}$ is His, D-His, D-Arg, imBzlD-His, D-Nal, D-Glu, D-Ala, D-Pal, D-Trp, D-Dpr(Nic), D-Aph, D-Agl(Nic), D-Orn, D-Dbu, D-Dpr or D-Orn(Nic); $R_{33}$ is Lys or Orn; $R_{34}$ is Asn or Aib; $R_{36}$ is Lys, CML or Leu; $R_{37}$ is Leu or CML; $R_{39}$ is Glu or Asp; $R_{40}$ is Ile, CML, Aib or Glu; and $R_{41}$ is Ile, Aib, CML or Ala; provided that D-2Nal or D-Leu or Phe may be substituted for D-Phe.

13. A cyclic CRF antagonist peptide according to claim 12 wherein $R_{18}$ is Val, $R_{22}$ is Ala, $R_{23}$ is Arg, $R_{24}$ is Ala, $R_{25}$ is Glu, $R_{28}$ is Ala, $R_{39}$ is Glu, and $R_{41}$ is Ile.

14. A cyclic CRF antagonist peptide according to claim 2 having the formula: (cyclo 30-33)Y-$R_9$-Leu-Thr-$R_{12}$-His-Leu-Leu-Arg-Glu-Val-Leu-Glu-Nle-Ala-$R_{23}$-Ala-Glu-Gln-$R_{27}$-Ala-Gln-$R_{30}$-Ala-His-$R_{33}$-Asn-Arg-Lys-Leu-Nle-Glu-Ile-Ile-NH$_2$ wherein Y is Ac or Acr; $R_9$ is Asp, Tyr or D-Tyr;

$R_{12}$ is D-Phe or D-2Nal; $R_{23}$ is Arg or Lys; $R_{27}$ is Leu or CML; $R_{30}$ is Glu; $R_{33}$ is Lys or Orn; and wherein His$^{32}$ may optionally be substituted by D-His, imBzlD-His, D-Arg, D-Tyr, D-Nal, D-Pal, D-Trp, D-Asn, D-Lys, D-Dpr(Nic), D-Aph, D-Phe, D-Cpa, D-Agl(Nic), D-Orn, D-Dbu, D-Dpr or D-Orn(Nic).

15. A cyclic CRF antagonist peptide according to claim 3 having the formula: (cyclo 30-33)Y-Asp-$R_{10}$-Thr-$R_{12}$-His-$R_{14}$-$R_{15}$-Arg-$R_{17}$-$R_{18}$-Leu-Glu-$R_{21}$-Ala-$R_{23}$-$R_{24}$-Glu-Gln-$R_{27}$-Ala-Gln-$R_{30}$-Ala-$R_{32}$-$R_{33}$-Asn-Arg-$R_{36}$-$R_{37}$-$R_{38}$-Glu-$R_{40}$-$R_{41}$-$NH_2$ wherein Y is Ac, For or Acr; $R_{10}$ is Leu or CML; $R_{12}$ is D-Phe or D-2Nal; $R_{14}$, $R_{15}$, $R_{27}$ and $R_{37}$ are independently Leu or CML; $R_{17}$ is Glu or CML; $R_{18}$ is Val or CML; $R_{21}$ is Met or Nle; $R_{23}$ is Arg or Lys; $R_{24}$ is Ala or CML; $R_{30}$ is Glu; $R_{32}$ is His, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{36}$ is Lys or CML; $R_{38}$ is Met, Nle or CML; and $R_{40}$ and $R_{41}$ are independently Ile or CML; and wherein at least one of $R_{14}$, $R_{18}$, $R_{27}$, $R_{36}$, $R_{37}$, $R_{40}$ and $R_{41}$ is CML; provided that a second cyclizing bond may exist between Glu$^{20}$ and $R_{23}$.

16. A cyclic CRF antagonist peptide according to claim 2 having the formula: (cyclo 30-33)Y-Asp-$R_{10}$-Thr-$R_{12}$-His-$R_{14}$-$R_{15}$-Arg-$R_{17}$-$R_{18}$-Leu-Glu-$R_{21}$-Ala-Arg-$R_{24}$-Glu-Gln-CML-Ala-Gln-Glu-Ala-$R_{32}$-$R_{33}$-Asn-Arg-$R_{36}$-$R_{37}$-$R_{38}$-Glu-$R_{40}$-$R_{41}$-$NH_2$ wherein Y is Ac, For or Acr; $R_{10}$ is Leu or CML; $R_{12}$ is D-Phe or D-2Nal; $R_{14}$, $R_{15}$, and $R_{37}$ are independently Leu or CML; $R_{17}$ is Glu or CML; $R_{18}$ is Val or CML; $R_{21}$ is Met or Nle; $R_{24}$ is Ala or CML; $R_{32}$ is His, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{36}$ is Lys or CML; $R_{38}$ is Met, Nle or CML; and $R_{40}$ and $R_{41}$ are independently Ile or CML; and wherein at least one of $R_{14}$, $R_{18}$, $R_{37}$ and $R_{40}$ is CML.

17. A method for screening for antagonists for CRF receptors which bind with high affinity to such receptors but do not substantially activate such receptors, which method comprises carrying out a competitive binding assay with a CRF receptor, a peptide according to claim 2 which contains a suitable label, and a candidate antagonist and determining the ability of said candidate antagonist to displace said labelled peptide.

18. A cyclic peptide which is an antagonist of CRF, which peptide has the formula: (cyclo 30-33)Y-Asp-$R_{10}$-Thr-$R_{12}$-His-$R_{14}$-$R_{15}$-Arg-$R_{17}$-$R_{18}$-Leu-Glu-$R_{21}$-$R_{22}$-$R_{23}$-$R_{24}$-Glu-Gln-CML-$R_{28}$-$R_{29}$-Glu-$R_{31}$ -$R_{32}$-$R_{33}$-$R_{34}$-Arg-$R_{36}$-$R_{37}$-$R_{38}$-$R_{39}$-$R_{40}$-$R_{41}$-$NH_2$ wherein Y is an acyl group having up to 15 carbon atoms; $R_{10}$, $R_{14}$, $R_{15}$, and $R_{37}$ are independently Leu or CML; $R_{12}$ is D-Phe or D-2Nal; $R_{17}$ is Glu or CML; $R_{18}$ is Val or CML; $R_{21}$ is Met or Nle; $R_{22}$, $R_{28}$ and $R_{31}$ are independently either Ala or Aib; $R_{23}$ is Arg or Lys; $R_{24}$ is Ala, Aib or CML; $R_{29}$ is Gln or Aib; $R_{32}$ is His, Aib, D-His, imBzlD-His, D-Arg, D-Asn, D-Tyr, D-Pal, D-Nal, D-Trp or another basic and/or aromatic D-isomer α-amino acid; $R_{33}$ is Lys or Orn; $R_{34}$ is Asn or Aib; $R_{36}$ is Lys or CML; $R_{38}$ is Met, Nle or CML; $R_{39}$ is Glu or Aib; and $R_{40}$ is Ile, CML or Aib; $R_{41}$ is Leu, CML or Aib; and wherein at least one of $R_{22}$, $R_{24}$, $R_{28}$, and $R_{31}$ is Aib; provided that a second cyclizing bond may exist between Glu$^{20}$ and $R_{23}$.

19. A cyclic peptide according to claim 18 wherein at least one of $R_{14}$, $R_{18}$, $R_{37}$, and $R_{40}$ is CML.

20. A cyclic peptide according to claim 18 having one of the following formulas:

[Ac-Asp$^9$, D-Phe$^{12}$, Nle$^{21,38}$, Aib$^{22}$, CML$^{27}$, Glu$^{30}$, Lys$^{33}$]-r/hCRF(9-41)

[Ac-Asp$^9$, D-Phe$^{12}$, Nle$^{21,38}$, Aib$^{24}$, CML$^{27}$, Glu$^{30}$, Lys$^{33}$]-r/hCRF(9-41)

[Ac-Asp$^9$, D-Phe$^{12}$, Nle$^{21,38}$, CML$^{27}$, Aib$^{28}$, Glu$^{30}$, Lys$^{33}$]-r/hCRF(9-41)

[Ac-Asp$^9$, D-Phe$^{12}$, Nle$^{21,38}$, CML$^{27}$, Aib$^{29}$, Glu$^{30}$, Lys$^{33}$]-r/hCRF(9-41)

[Ac-Asp$^9$, D-Phe$^{12}$, Nle$^{21,38}$, CML$^{27}$, Glu$^{30}$, Aib$^{31}$, Lys$^{33}$]-r/hCRF(9-41)

[Ac-Asp$^9$, D-Phe$^{12}$, Nle$^{21,38}$, CML$^{27}$, Glu$^{30}$, Lys$^{33}$, Aib$^{34}$]-r/hCRF(9-41)

[Ac-Asp$^9$, D-Phe$^{12}$, Nle$^{21,38}$, CML$^{27}$, Glu$^{30}$, Lys$^{33}$, Aib$^{39}$]-r/hCRF(9-41)

[Ac-Asp$^9$, D-Phe$^{12}$, Nle$^{21,38}$, CML$^{27}$, Glu$^{30}$, Lys$^{33}$, Aib$^{40}$]-r/hCRF(9-41)

[Ac-Asp$^9$, D-Phe$^{12}$, Nle$^{21,38}$, CML$^{27}$, Glu$^{30}$, Lys$^{33}$, Aib$^{41}$]-r/hCRF(9-41)

[Ac-Asp$^9$, D-Phe$^{12}$, Nle$^{21,38}$, CML$^{27,40}$, Glu$^{30}$, Lys$^{33}$, Aib$^{41}$]-r/hCRF(9-41)

[Ac-Asp$^9$, D-Phe$^{12}$, Nle$^{21,38}$, Aib$^{22}$, CML$^{27,40}$, Glu$^{30}$, Lys$^{33}$]-r/hCRF(9-41)

[Ac-Asp$^9$, D-Phe$^{12}$, Nle$^{21,38}$, Aib$^{24}$, CML$^{27,40}$, Glu$^{30}$, Lys$^{33}$]-r/hCRF(9-41)

[Ac-Asp$^9$, D-Phe$^{12}$, Nle$^{21,38}$, Aib$^{22,24}$, CML$^{27}$, Glu$^{30}$, Lys$^{33}$]-r/hCRF(9-41)

[Ac-Asp$^9$, D-Phe$^{12}$, Nle$^{21,38}$, CML$^{27,40}$, Aib$^{28}$, Glu$^{30}$, Lys$^{33}$]-r/hCRF(9-41)

[Ac-Asp$^9$, D-Phe$^{12}$, CML$^{18,27}$, Nle$^{21,38}$, Glu$^{30}$, Aib$^{31,41}$, Lys$^{33}$]-r/hCRF(9-41)

[Ac-Asp$^9$, D-Phe$^{12}$, CML$^{14,27}$, Nle$^{21,38}$, Glu$^{30}$, Aib$^{31}$, Lys$^{33}$]-r/hCRF(9-41)

[Ac-Asp$^9$, D-Phe$^{12}$, Nle$^{21,38}$, CML$^{27,37}$, Aib$^{28,31}$, Glu$^{30}$, Lys$^{33}$]-r/hCRF(9-41)

[Ac-Asp$^9$, D-Phe$^{12}$, CML$^{14,27}$, Nle$^{21,38}$, Aib$^{24,41}$, Glu$^{30}$, Lys$^{33}$]-r/hCRF(9-41).

* * * * *

UNITED STATES PATENT AND TRADEMARK OFFICE
CERTIFICATE OF CORRECTION

PATENT NO. : 5,777,073
DATED : July 7, 1998
INVENTOR(S) : Rivier

It is certified that error appears in the above-identified patent and that said Letters Patent is hereby corrected as shown below:

Column 44, line 37, delete "amino group which forms the";

line 38, delete "lactam bond".

IN THE CLAIMS:

Column 49, line 67, "13-29" should be --34-41--;
        Column 49, line 67, "or" should be --and--.
        Column 50, line 46, "12-28" should be --33-40--.

Signed and Sealed this

Sixteenth Day of May, 2000

Attest:

Q. TODD DICKINSON

Attesting Officer        Director of Patents and Trademarks